United States Patent

Wilhelm et al.

Patent Number: 5,264,437
Date of Patent: Nov. 23, 1993

[54] OPTIONALLY SUBSTITUTED PYRIDO[2,3-D]PYRIDINE-2,4(1H,3H)-DIONES AND PYRIDO[2,3-D]PYRIMIDINE-2(1H,3H)-ONES

[75] Inventors: Robert S. Wilhelm; Ronnie L. Chin, both of Mountain View; Bruce H. Devens, Palo Alto; Robert Alvarez, Menlo Park, all of Calif.

[73] Assignee: Syntex (U.S.A.) Inc., Palo Alto, Calif.

[21] Appl. No.: 855,179

[22] Filed: Mar. 20, 1992

[51] Int. Cl.$^5$ .................. A61K 31/505; C07D 471/04
[52] U.S. Cl. .................... 514/258; 514/253; 544/238; 544/279
[58] Field of Search ............ 544/279, 238; 514/253, 514/258

[56] References Cited

U.S. PATENT DOCUMENTS

| 3,984,415 | 10/1976 | Noda et al. | 260/256.5 |
| 4,009,166 | 2/1977 | Noda et al. | 260/256.4 F |
| 4,880,810 | 11/1989 | Lowe, III | 514/258 |

FOREIGN PATENT DOCUMENTS 1401549 7/1973 Japan.

OTHER PUBLICATIONS

Levin, et al., "An Alternative Procedure for the Aluminum-Mediated Conversion of Esters to Amides", Synth. Com. 12:989–993 (1982).

Primary Examiner—Thurman K. Page
Assistant Examiner—Jyothsna Venkat
Attorney, Agent, or Firm—James J. Wong; David A. Lowin; Alan M. Krubiner

[57] ABSTRACT

The present invention relates to optionally substituted pyrido[2,3-d]pyrimidine-2,4(1H,3H)-diones or optionally substituted pyrido[2,3-d]pyrimidine-2(1H,3H)-ones, i.e., compounds of Formula I:

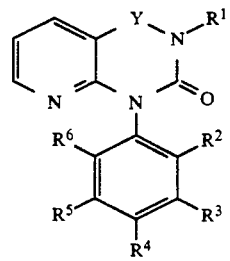

Formula I wherein:
Y is —CH$_2$— or —C(O)—;
R$^1$ is hydrogen or —(CH$_2$)$_n$—R$^7$, wherein:
  R$^7$ is aryl or heteroaryl, and
  n is 1 or 2,
  provided that when Y is —C(O)—, R$^7$ is heteroaryl; and
R$^2$, R$^3$, R$^4$, R$^5$ and R$^6$ are hydrogen, or one is selected from lower alkyl, halo, carboxy, methoxycarbonyl, carbamoyl, methylcarbamoyl, di-methylcarbamoyl, methylcarbonyl, methylthio, methylsulfinyl, methylsulfonyl, hydroxymethyl, amino, trifluoromethyl, cyano or nitro; or
R$^2$, R$^3$, R$^4$ and R$^5$ are independently selected from hydrogen, lower alkyl, nitro, chloro, fluoro, methoxycarbonyl or methylcarbonyl, provided at least one is hydrogen, and R$^6$ is hydrogen;

or a pharmaceutically acceptable ester, ether or salt thereof.

53 Claims, No Drawings

OPTIONALLY SUBSTITUTED PYRIDO[2,3-D]PYRIDINE-2,4(1H,3H)-DIONES AND PYRIDO[2,3-D]PYRIMIDINE-2(1H,3H)-ONES

BACKGROUND OF THE INVENTION

1. Field of the Invention

This invention relates to optionally substituted pyrido[2,3-d]pyrimidine-2,4(1H,3H)-diones and pyrido[2,3-d]pyrimidine-2(1H,3H)-ones particularly to 1-(optionally substituted)phenyl-3-(optionally substituted heteroarylalkyl or arylalkyl)-pyrido[2,3-d]pyrimidine-2,4(1H,3H)-diones and pyrido[2,3-d]pyrimidine-2(1H,3H)-ones, useful as anti-inflammatory agents, immunosuppressive agents, anti-allograft rejection agents, anti-graft-vs-host disease agents, anti-allergic agents (e.g., asthma, rhinitis and atopic dermatitis), anti-autoimmune agents or analgetic agents, to their precursors, to their preparation and to pharmaceutical compositions using the compounds of the invention.

2. Background of the Invention

Cyclic 3',5'-adenosine monophosphate (cAMP) modulates a variety of cellular and physiologic functions in mammals, such as, cell division, endocrine function, and the immune response. The level of cAMP is controlled by a class of enzymes called phosphodiesterases, which enzymatically deactivate cAMP. There are five general types of phosphodiesterases, which are categorized according to the their function and the type of cell from which they are isolated. For instance, high-affinity phosphodiesterase (PDE III) is isolated from human platelet cells and modulates platelet aggregation. Another type of phosphodiesterase (PDE IV) is found in various tissues but is the predominant form in human leukocytes; this enzyme modulates leukocyte activation and function associated with the immune response and inflammation. Both of these phosphodiesterases implement their control by modulating the cellular level of cAMP in their respective cells. Thus, inhibition of phosphodiesterases provides a method of modulating any cellular and bodily function that is controlled by cAMP.

Compounds that are nonspecific phosphodiesterase inhibitors are known, i.e., these compounds inhibit all or multiple types of phosphodiesterases. [See, Beavo, J. A. and D. H. Reifsyder, Trends in Pharm. Science, 11:150–155 (1990); and Nicholson, C. D., R. A. J. Challiss and M. Shahid, Trends in Pharm. Science, 12:19–27 (1991).] Since cAMP is involved in so many functions throughout the body, a nonspecific phosphodiesterase inhibitor has the potential to alter all of the functions modulated by cAMP, thus nonspecific phosphodiesterase inhibitors are of limited value because of numerous side-effects.

It has been surprisingly discovered that certain optionally substituted pyrido[2,3-d]pyrimidine-2,4(1H,3H)-diones and pyrido[2,3-d]pyrimidine-2(1H,3H)-ones are potent selective inhibitors of Phosphodiesterase Type IV (PDE IV). These compounds are well suited for use as a treatment for any disorder in which PDE IV function plays a role, such as where leukocyte activation or function is involved. In particular, these compounds are especially well suited for use as anti-inflammatory agents, immunosuppressive agents, anti-allograft rejection agents, anti-graft-vs-host disease agents, anti-allergic agents (e.g., asthma, rhinitis and atopic dermatitis), anti-autoimmune disease agents or analgetic agents.

SUMMARY OF THE INVENTION

One aspect of the present invention relates to optionally substituted pyrido[2,3-d]pyrimidine-2,4(1H,3H)-diones, and optionally substituted pyrido[2,3-d]pyrimidine-H,3H)-ones, and precursors thereto, i.e., compounds of Formula I:

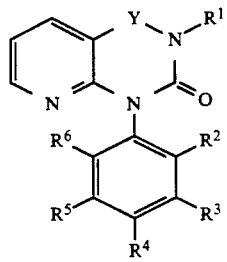

Formula I wherein:
Y is —CH$_2$— or —C(O)—;
R$^1$ is hydrogen, or —(CH$_2$)$_n$—R$^7$, wherein:
  R$^7$ is aryl or heteroaryl, and
  n is 1 or 2,
  provided that when Y is —C(O)—, R$^7$ is heteroaryl; and
R$^2$, R$^3$, R$^4$, R$^5$ and R$^6$ are hydrogen, or one is selected from lower alkyl, halo, carboxy, methoxycarbonyl, carbamoyl, methylcarbamoyl, di-methylcarbamoyl, methylcarbonyl, methylthio, methylsulfinyl, methylsulfonyl, hydroxymethyl, amino, trifluoromethyl, cyano or nitro; or
R$^2$, R$^3$, R$^4$ and R$^5$ are independently selected from hydrogen, lower alkyl, nitro, chloro, fluoro, methoxycarbonyl or methylcarbonyl, provided that at least one is hydrogen, and R$^6$ is hydrogen;
and the pharmaceutically acceptable esters, ethers, salts and N-oxides (where R$^7$ is nitrogen-containing heteroaryl) thereof, and precursors thereto.

In another aspect, the invention relates to a pharmaceutical composition containing a therapeutically effective amount of a compound of Formula I or a pharmaceutically acceptable ester, ether, salt or N-oxide thereof admixed with at least one pharmaceutically acceptable excipient.

In still another aspect, the invention relates to a method of use as an anti-inflammatory agent, immunosuppressive agent, anti-allograft rejection agent, anti-graft-vs-host disease agent, anti-allergic agent (e.g., asthma, rhinitis and atopic dermatitis), anti-autoimmune disease agent or analgetic agent, by administering to a mammal in need of such treatment a therapeutically effective amount of a compound of Formula I or a pharmaceutically acceptable ester, ether, salt or N-oxide thereof.

Yet another aspect of the invention relates to the treatment of the above conditions or diseases by the selective inhibition of PDE IV.

Still another aspect of the invention relates to precursor compounds corresponding to Formula I where Y is —CH$_2$— and R$^1$ is replaced by hydrogen.

Another aspect of the invention relates to processes for making the compounds of Formula I and pharmaceutically acceptable salts, esters and ethers thereof. For example, a compound of Formula I is made by contacting a precursor compound with a corresponding compound of the formula, X—(CH$_2$)$_n$—R$^7$ wherein: X is halo or —OH.

In another aspect, this invention provides compositions useful in the treatment of inflammatory, allograft rejection, graft-vs-host disease, allergy, autoimmune or analgetic conditions or diseases in mammals comprising a therapeutically effective amount of a compound of Formula I or a pharmaceutically acceptable ester, ether, salt or N-oxide as described above and a pharmaceutically acceptable excipient.

DETAILED DESCRIPTION

Definition and General Parameters

The following definitions are set forth to illustrate and define the meaning and scope of the various terms used to describe the invention herein.

The term "alkyl" refers to a cyclic, branched or straight chain monovalent saturated aliphatic hydrocarbon radical of one to twenty carbon atoms.

The term "lower alkyl" refers to a cyclic, substituted cyclic, branched or straight chain monovalent alkyl radical of one to four carbon atoms. This term is further exemplified by such radicals as methyl, ethyl, n-propyl, isopropyl, i-butyl, n-butyl and t-butyl.

The term "lower alkoxy" refers to the group —O—R' where R' is lower alkyl.

The term "carbonyl" refers to the group —C(O)—.

The term "methylene" refers to the group —CH$_2$—.

The term "carboxy" refers to the group —C(O)OH.

The term "lower-alkoxycarbonyl" refers to the group —C(O)OR' where R' is lower-alkyl.

The term "acyl" refers to the group —C(O)—R, where R is lower alkyl, such as, methylcarbonyl and ethylcarbonyl.

The term "carbamoyl" refers to the group —C(O)NR$^8$R$^9$ where R$^8$ and R$^9$ are independently hydrogen or methyl.

The term "halo" refers to fluoro, bromo, chloro and iodo.

The term "methylthio" refers to the group CH$_3$—S—.

The term "methylsulfinyl" refers to the group CH$_3$—S(O)—.

The term "methylsulfonyl" refers to the group CH$_3$—S(O$_2$)—.

The term "aryl" refers to an aromatic monovalent mono or poly- carbocyclic radical, which can optionally be mono-, di-, tri- or tetra-substituted, independently, with lower alkyl, halo, carboxy, lower-alkoxycarbonyl, carbamoyl, mono- and dimethylcarbamoyl, acyl (such as, methylcarbonyl and ethylcarbonyl), methylthio, methylsulfinyl, methylsulfonyl, hydroxymethyl, amino, trifluoromethyl, cyano or nitro.

The term "heteroaryl" or "heterocyclic rings" refers to aromatic monovalent mono- or poly- carbocyclic radical having at least one heteroatom, i.e., nitrogen, oxygen or sulfur, which can optionally be mono- or di-substituted adjacent to the heteroatom, independently, with lower alkyl, halo, cyano, amino or trifluoromethyl. For example, typical heteroaryl groups with one or more nitrogen atoms are tetrazoyl, pyridyl (e.g., 4-pyridyl, 3-pyridyl, 2-pyridyl), pyridazinyl, quinolinyl, 2-quinolinyl, 3-quinolinyl, imidazolyl, isoquinolinyl, pyrazolyl, pyrazinyl, pyrimidinyl, pyridonyl or pyridazinonyl; typical oxygen heteroaryl radicals with oxygen atom are furanyl, or benzofuranyl; typical sulfur heteroaryl radicals are thienyl, and benzothiophenyl.

The term "heteroarylalkyl" refers to the group -(lower alkyl)-(heteroaryl). For example, typical heteroarylalkyl groups are e.g., pyridyl-lower alkyl, such as, pyridylmethyl (e.g., 4-pyridylmethyl, 3-pyridylmethyl and 2-pyridylmethyl), pyridylethyl, pyridylpropyl, pyridylbutyl, quinolinyl-lower alkyl, furanyl-lower alkyl, and pyridonyl-lower alkyl.

The term "electron withdrawing group" refers to a radical group that will draw electrons to itself more than a hydrogen atom would if it occupied the same position in the molecule. For example, typical electron withdrawing groups are halo (e.g., chloro, bromo, iodo and fluoro), nitro, trifluoromethyl, cyano, carboxy, methoxycarbonyl and methylcarbonyl.

The term "pharmaceutically acceptable esters" refers to those compounds formed from compounds of Formula I containing a carboxy group when contacted with an alcohol, such as, methanol, ethanol or propanol under suitable conditions.

The term "pharmaceutically acceptable ethers" refers to those compounds formed from compounds of Formula I containing a hydroxy group when contacted with a suitable reagents (e.g., alkyl halide) under suitable conditions.

The term refers to a

nitrogen heteroaryl radical.

The term "esterification reagent" refers to a reagent (e.g., diazomethane, methanol, methyl iodide, ethyl iodide or ethanol) that when contacted with a carboxy group under suitable circumstances results in the formation of the corresponding alkoxycarbonyl group.

The term "compound", as used in the detailed description and in the claims (particularly the dependent claims) in reference to a compound of Formula I, is intended to refer to the pharmaceutically acceptable salts, esters or N-oxides of the compound, unless expressly stated otherwise, such as "the compound of Formula I as a free base".

The term "pharmaceutically acceptable salt" refers to any salt derived from an inorganic or organic acid or base.

The term "pharmaceutically acceptable anion" refers to the anion of such acid addition salts. The term "pharmaceutically acceptable cation" refers to the cation of such base addition salts. The salt, anion and/or the action are chosen not to be biologically or otherwise undesirable.

The anions are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid and the like.

The cations are derived from bases, such as alkaline earth hydroxides, including calcium hydroxide, potassium hydroxide, sodium hydroxide, lithium hydroxide and the like.

The terms "inert organic solvent" or "inert solvent" refer to a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, pyridine and the like]. Unless specified to the contrary, the solvents used in the reactions of the present invention are inert organic solvents.

As used herein, the term "allograft rejection" refers to the humoral or cellular immune response mounted by the immune system of a mammal after it has received a histo-incompatible tissue graft from another mammal of the same species, thereby producing tissue injury to the graft in such a recipient.

As used herein, the term "graft-vs-host disease" refers to the immune response that originates from transplanted graft tissue, in particular, transplanted bone-marrow tissue, and that is directed towards the host tissue, thereby producing tissue injury in the host.

As used herein, the term "autoimmune disease" refers to disorders wherein the immune system of a mammal mounts a humoral or cellular immune response to the mammal's own tissue or to antigenic agents that are not intrinsically harmful to the mammal, thereby producing tissue injury in such a mammal. Examples of such disorders include, but are not limited to, systemic lupus erythematosus, rheumatoid arthritis and type I diabetes As used herein, the terms "treatment" or "treating" of a condition and/or a disease in a mammal, means:

(i) preventing the condition or disease, that is, avoiding any clinical symptoms of the disease;

(ii) inhibiting the condition or disease, that is, arresting the development or progression of clinical symptoms; and/or (iii) relieving the condition or disease, that is, causing the regression of clinical symptoms. The conditions and diseases treated in the present invention include, inflammation, pain, pyrexia, autoimmune disease, allograft rejection, graft-vs-host, disease, allergies and uveitis.

As used herein, the term "therapeutically effective amount" refers to that amount of a compound of Formula I which, when administered to a mammal in need thereof, is sufficient to effect treatment (as defined above) as an anti-inflammatory agent, immunosuppressive agent, anti-allograft rejection agent, anti-graft-vs-host disease agent, anti-allergy agent, autoimmune disease agent or analgetic agent. The amount that constitutes a "therapeutically effective amount" will vary depending on the compound, the condition or disease and its severity, and the mammal to be treated, but may be determined routinely by one of ordinary skill in the art with regard to contemporary knowledge and to this disclosure.

As used herein, the term "q.s." means adding a quantity sufficient to achieve a stated function, e.g., to bring a solution to a desired volume (e.g., 100 mL).

As used herein, the term "mp" refers to melting point. All temperatures are given in degrees Celsius (i.e., °C.).

Unless specified to the contrary, the reactions described herein take place at atmospheric pressure over a temperature range from about $-20°$ C. to about 150° C., more preferably from about 10° C. to about 50° C., and most preferably at about room (or "ambient") temperature, e.g., about 20° C. Unless specified to the contrary, the ranges of time and temperature described herein are approximate, e.g., "from 8 to 24 hours at from 10° C. to 100° C." means from about 8 to about 24 hours at about 10° C. to about 100° C.

Isolation and purification of the compounds and intermediates described herein can be effected, if desired, by any suitable separation or purification procedure such as, for example, filtration, extraction, crystallization, column chromatography, preparative high pressure liquid chromatography (preparative HPLC), thin-layer chromatography or thick-layer chromatography, or a combination of these procedures. Specific illustrations of suitable separation and isolation procedures can be had by reference to the examples hereinbelow. However, other equivalent separation or isolation procedures can also be used.

The following numbering and nomenclature system will be used for naming the compounds of the invention.

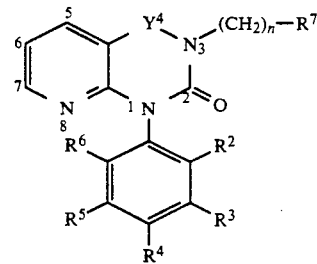

Some representative compounds are named in the following examples.

The compound of Formula I where Y is $-C(O)-$, n is one, $R^7$ is 4-pyridyl, $R^3$ is nitro and $R^2$, $R^4$, $R^5$ and $R^6$ are hydrogen can be named 1-(3-nitrophenyl)-3-(4-pyridylmethyl)pyrido[2,3-d]pyrimidine-2,4(1H,3H)-dione.

The compound of Formula I where Y is $-C(O)-$, n is one, $R^7$ is 2-quinolinyl, $R^3$ is nitro and $R^2$, $R^4$, $R^5$ and $R^6$ are hydrogen can be named 1-(3-nitrophenyl)-3-(2-quinolinylmethyl)pyrido[2,3-d]pyrimidine-2,4(1H,3H)-dione.

The compound of Formula I where Y is $-C(O)-$, n is one, $R^7$ is 3-pyridyl, $R^3$ is chloro and $R^2$, $R^4$, $R^5$ and $R^6$ are hydrogen can be named 1-(3-chlorophenyl)-3-(3-pyridylmethyl)pyrido[2,3-d]pyrimidine-2,4(1H,3H)-dione.

The compound of Formula I where Y is $-C(O)-$, n is two, $R^7$ is 2-pyridyl, $R^3$ and $R^4$ are chloro and $R^2$, $R^5$ and $R^6$ are hydrogen can be named 1-(3,4-dichlorophenyl)-3-(2-pyridyl-2-ethyl)pyrido[2,3-d]pyrimidine-2,4(1H,3H)-dione.

The compound of Formula I where Y is $-C(O)-$, n is two, $R^7$ is 4-pyridyl, $R^2$ is methyl, $R^3$ is chloro and $R^4$, $R^5$ and $R^6$ are hydrogen can be named 1-(2-methyl-3-chlorophenyl)-3-(4-pyridyl-2-ethyl)pyrido[2,3-d]pyrimidine-2,4(1H,3H)-dione.

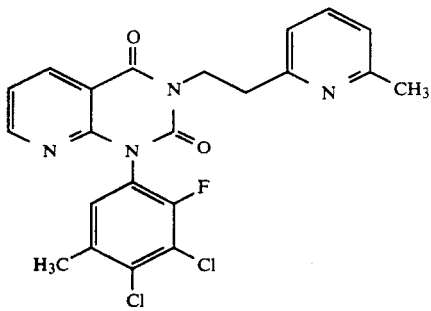

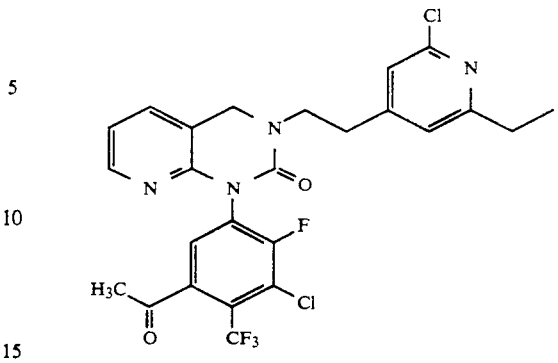

The compound of Formula I (as illustrated above) where Y is —C(O)—, n is two, $R^7$ is 2-pyridyl-6-methyl, $R^2$ is fluoro, $R^3$ and $R^4$ are chloro, $R^5$ is methyl and $R^6$ are hydrogen can be named 1-(2-fluoro-3,4-dichloro-6-methylphenyl)-3-[2-pyridyl-5-methyl)-2-ethyl]-pyrido[2,3-d]pyrimidine-2,4(1H,3H)-dione.

The compound of Formula I where Y is —CH$_2$—, n is one, $R^7$ is 4-pyridyl, $R^3$ is nitro and $R^2$, $R^4$, $R^5$ and $R^6$ are hydrogen can be named 1-(3-nitrophenyl)-3-(4-pyridylmethyl)pyrido[2,3-d]pyrimidine-2(1H,3H)-one.

The compound of Formula I where Y is —CH$_2$—, n is one, $R^7$ is 2-quinolinyl, $R^3$ is nitro and $R^2$, $R^4$, $R^5$ and $R^6$ are hydrogen can be named 1-(3-nitrophenyl)-3-(2-quinolinylmethyl)pyrido[2,3-d]pyrimidine-2(1H,3H)-one.

The compound of Formula I where Y is —CH$_2$—, n is one, $R^7$ is 3-pyridyl, $R^3$ is chloro and $R^2$, $R^4$, $R^5$ and $R^6$ are hydrogen can be named 1-(3-chlorophenyl)-3-(3-pyridylmethyl)pyrido[2,3-d]pyrimidine-2(1H,3H)-one.

The compound of Formula I where Y is —CH$_2$—, n is one, $R^7$ is 2-pyridyl, $R^3$ and $R^4$ are chloro and $R^2$, $R^5$ and $R^6$ are hydrogen can be named 1-(3,4-dichlorophenyl)-3-(2-pyridylmethyl)pyrido[2,3-d]pyrimidine-2(1H,3H)-one.

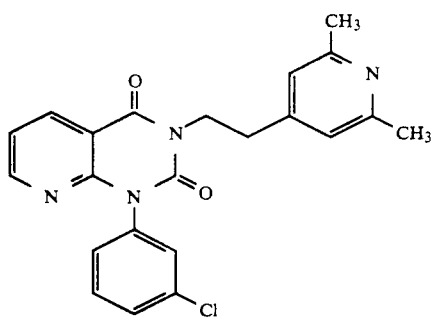

The compound of Formula I (as illustrated above) where Y is —CH$_2$—, n is two, $R^7$ is 4-pyridyl(2,6-dimethyl), $R^3$ is chloro and $R^2$, $R^4$, $R^5$ and $R^6$ are hydrogen can be named 1-(3-chlorophenyl)-3-[4-pyridyl-2,6-dimethyl)-2-ethyl]pyrido[2,3-d]-pyrimidine-2(1H,3H)-one.

The compound of Formula I where Y is —CH$_2$—, n is two, $R^7$ is 2-pyridyl, $R^3$ is methylthio and $R^2$, $R^4$, $R^5$ and $R^6$ are hydrogen can be named 1-(3-methylthiophenyl)-3-(2-pyridyl-2-ethyl)pyrido[2,3-d]pyrimidine-2(1H,3H)-one.

The compound of Formula I (as illustrated above) where Y is —CH$_2$—, n is 2, $R^7$ is 4-(2-chloro-6-ethyl)-pyridyl, $R^2$ is fluoro, $R^3$ is chloro, $R^4$ is trifluoromethyl, $R^5$ is methylcarbonyl and $R^6$ is hydrogen can be named 1-(2-fluoro-3-chloro-4-trifluoromethyl-5-methylcarbonylphenyl)-3-[4-(2-chloro-6-ethyl)pyridyl-2-ethyl]-pyrido[2,3-d]pyrimidine-2(1H,3H)-one.

SYNTHESIS OF THE COMPOUNDS OF FORMULA I

As used in the Reaction Schemes, Y, n, $R^1$, $R^2$, $R^3$, $R^4$, $R^5$, $R^6$ and $R^7$ are the same as described in the Summary of the Invention.

Reaction Scheme A illustrates the preparation of novel optionally substituted pyrido[2,3-d]pyrimidine-2,4(1H,3H)-diones, i.e., the compounds of Formula I where Y is —C(O)—.

Reaction Scheme B illustrates the preparation of novel optionally substituted pyrido[2,3-d]pyrimidine-2(1H,3H)-ones, i.e., the compounds of Formula I where Y is —CH$_2$—.

Reaction Scheme C illustrates the preparation of novel optionally substituted 3-[3-(6-methyl)pyridyl-(lower alkyl)]pyrido[2,3-d]pyrimidine-2,4(1H,3H)-diones and 3-[3-(6-methyl)pyridyl-(lower alkyl)]-pyrido[2,3-d]pyrimidine-2(1H,3H)-ones, i.e., the compounds of Formula I where $R^1$ is 3-(6-lower-alkyl)pyridyl-(lower alkyl).

Reaction Scheme D illustrates the preparation of novel optionally substituted pyrido[2,3-d]pyrimidine-2,4(1H,3H)-diones and pyrido[2,3-d]pyrimidine-2(1H,3H)-ones, i.e., the compounds of Formula I where $R^2$, $R^3$, $R^4$, $R^5$, or $R^6$ is carbamoyl.

Reaction Scheme E illustrates the preparation of novel optionally substituted pyrido[2,3-d]pyrimidine-2,4(1H,3H)-diones and pyrido[2,3-d]pyrimidine-2(1H,3H)-ones, i.e., the compounds of Formula I where $R^2$, $R^3$, $R^4$, $R^5$, or $R^6$ is —C(O)NR$^8$R$^9$, wherein $R^8$ and $R^9$ are independently selected from hydrogen and methyl.

Reaction Scheme F illustrates the preparation of novel optionally substituted pyrido[2,3-d]pyrimidine-2,4(1H,3H)-diones and pyrido[2,3-d]pyrimidine-2(1H,3H)-ones, i.e., the compounds of Formula I where $R^2$, $R^3$, $R^4$, $R^5$, or $R^6$ is —S(O)—CH$_3$.

Reaction Scheme G illustrates the preparation of novel optionally substituted pyrido[2,3-d]pyrimidine-2,4(1H,3H)-diones and pyrido[2,3-d]pyrimidine-2(1H,3H)-ones, i.e., the compounds of Formula I where $R^2$, $R^3$, $R^4$, $R^5$, or $R^6$ is —S(O$_2$)—CH$_3$.

Reaction Scheme H illustrates the preparation of novel optionally substituted pyrido[2,3-d]pyrimidine- 2,4(1H,3H)-diones and pyrido[2,3-d]pyrimidine-2(1H,3H)-ones, i.e., the compounds of Formula I where $R^2$, $R^3$, $R^4$, $R^5$, or $R^6$ is $-CH_2-CH-OH$.

Reaction Scheme I illustrates the preparation of novel optionally substituted pyrido[2,3-d]pyrimidine-2,4(1H,3H)-diones diones and pyrido[2,3-d]pyrimidine-2(1H,3H)-ones, i.e., the compounds of Formula I where $R^2$, $R^3$, $R^4$, $R^5$, or $R^6$ is $-NH_2$.

Reaction Scheme J illustrates the preparation of N-oxide derivatives of novel optionally substituted pyrido[2,3-d]pyrimidine-2,4(1H,3H)-diones and pyrido[2,3-d]pyrimidine-2(1H,3)-ones.

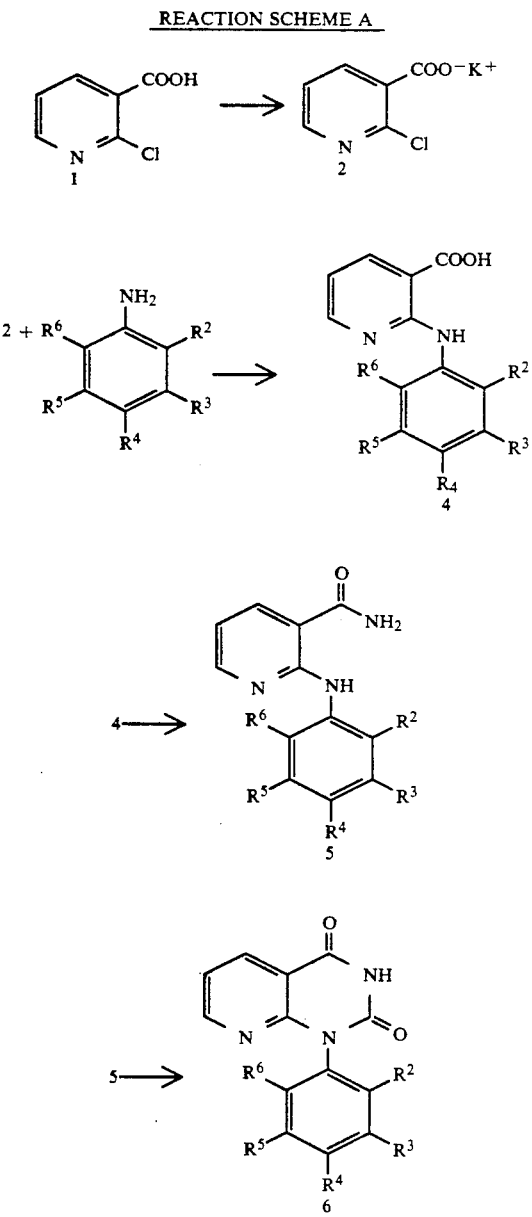

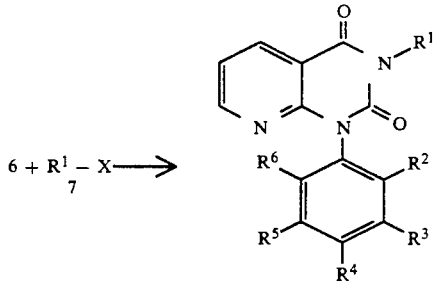

Formula I, where Y is $-C(O)-$

STARTING MATERIALS

Referring to Reaction Scheme A, Formula 1 (2-chloro nicotinic acid), most of the compounds of Formula 3 [anilines optionally substituted with lower alkyl (e.g., methyl, ethyl, propyl or butyl), halo (e.g., chloro, bromo, iodo or fluoro), carboxy, lower-alkoxy carbonyl (e.g., methoxycarbonyl, ethoxycarbonyl or propoxycarbonyl), lower-alkyl carbonyl (e.g., methylcarbonyl, ethylcarbonyl or propylcarbonyl), hydroxymethyl, cyano, nitro, methylthio and/or trifluoromethyl] and Formula 7 (optionally substituted heteroarylalkyl halides and arylalkyl halides) are commercially available from Aldrich Chemicals Co., Inc., Fluka Chemical Corporation, Lancaster Synthesis Ltd., Maybridge Chemical Co. Ltd. or Tokyo Kasai International. Those compounds that are not commercially available can be prepared by one of ordinary skill in art following procedures set forth in references such as, "Fieser and Fieser's Reagents for Organic Synthesis", Volumes 1-15, John Wiley and Sons, 1991; "Rodd's Chemistry of Carbon Compounds", Volumes 1-5 and Supplementals, Elsevier Science Publishers, 1989; and "Organic Reactions", Volumes 1-40, John Wiley and Sons, 1991. The compounds where $R^2$-$R^6$ are optionally substituted with carbamoyl, methyl and dimethylcarbamoyl, methylsulfinyl, methylsulfonyl, hydroxymethyl, and amino prepared from the other compounds of Formula I as described in Reaction Schemes A and B.

PREPARATION OF FORMULA 2

2-Chloro nicotinic acid (Formula 1) is suspended in a solvent (such as, methanol or ethanol, preferably ethanol) and stirred at about room temperature (i.e., about 20°-30° C.) while 1 molar equivalent of a strong base (such as, potassium hydroxide (solid), sodium hydroxide or the like) is added gradually. The suspension is stirred for about 4 hrs during which time a solution is formed, followed by the formation of a precipitate. Approximately three quarters of the solvent is removed and the precipitate is filtered out of the remaining solvent. The precipitate is washed with a solvent (e.g., ethyl ether) and dried, yielding potassium 2-chloro nicotinate, i.e., Formula 2.

PREPARATION OF FORMULA 4

Potassium 2-chloro-nicotinate (Formula 2) is suspended in an aprotic solvent (such as, dimethylformamide or dimethylsulfoxide preferably dimethylformamide). To this suspension is added about 1.0 molar equivalent of an optionally substituted aniline (Formula 3)

followed by about 0.06 molar equivalent of a copper II salt (such as, cupric acetate) and about 1 molar equivalent of N-ethyl morpholine. The resulting suspension is refluxed with stirring under an inert atmosphere for a period of about 10 to 26 hours, preferably about 18 hours. The reaction mixture is cooled to about room temperature and 6M HCl is added in a dropwise manner until the pH is between 4 and 5. The desired product may form a precipitate, in which case it is filtered off and washed with $H_2O$, then air dried. Otherwise, most of the solvent is removed in vacuo, the resulting residue is poured into $H_2O$ and extracted with ethyl acetate. The organic layers are combined, dried over $MgSO_4$, and concentrated. The desired product may precipitate out of the residue, in which case the product is triturated with $Et_2O$ then filtered and air dried. The remaining residue is chromatographed on a column of silica gel [using an appropriate solvent to elute (e.g., 9: $CH_2Cl_2$:MeOH)], and then is combined with the previously collected precipitate yielding an optionally substituted 2-anilino-3-carboxypyridine (Formula 4).

PREPARATION OF FORMULA 5

An optionally substituted 2-anilino-3-carboxypyridine (Formula 4) is suspended in an inert solvent (such as, toluene or benzene, preferably, benzene). To the suspension is added about 2 molar equivalents of thionyl chloride in a gradual manner. The resulting mixture is refluxed for about 4 hrs. resulting in the formation of a solution. The solvent is removed in vacuo yielding an acid chloride, which is used in the next step without further purification. The acid chloride is dissolved in a solvent (such as, tetrahydrofuran, ethyl ether or ethyl acetate, preferably tetrahydrofuran) and about 2.5 molar equivalents of concentrated $NH_4OH$ is added in a gradual manner with stirring. A precipitate is formed and the reaction mixture is stirred for about 3 hours at about room temperature. The solvent is removed in vacuo. $H_2O$ is added to the resulting residue, followed by extraction with ethyl acetate. The resulting organic layers are combined, and dried over a drying agent (such as, $MgSO_4$). The solution is filtered and concentrated by the removal of the solvent, followed by trituration with $Et_2O$, isolation by filtration and drying yielding the desired optionally substituted 2-anilino-3-carbamoylpyridine (Formula 5).

PREPARATION OF FORMULA 6

An optionally substituted 2-anilino-3-carbamoylpyridine(Formula 5) is dissolved in a polar aprotic solvent (such as, dimethylformamide, or tetrahydrofuran, preferably tetrahydrofuran). To this solution is added about 3 molar equivalent of NaH. The solution is stirred at about room temperature under an inert atmosphere for about 3 minutes. About 1.5 molar equivalent of 1,1'-carbonyldiimidazole is added in a gradual manner. The resulting suspension is heated to reflux for about 18 hours. The mixture is cooled to about room temperature and the solvent removed in vacuo. $H_2O$ is added to the resulting solid mass to quench the unreacted NaH. The suspension is extracted into a suitable solvent (such as, ethyl acetate) and treated with a drying agent (e.g., $MgSO_4$). The solid material is filtered out and the solvent is removed yielding a 1-(optionally substituted phenyl)-pyrido[2,3-d]pyrimidine-2,4(1H,3H)-dione (Formula 6).

PREPARATION OF FORMULA I, WHERE Y IS —C(O)—

A 1-(optionally substituted phenyl)-pyrido[2,3-d]pyrimidine-2,4(1H,3H)-dione (Formula 6) is suspended in an aprotic solvent (e.g., tetrahydrofuran, acetone, dimethylformamide, preferably dimethylformamide) and about 2 molar equivalent of a strong base (e.g., $K_2CO_3$ or NaH, preferably $K_2CO_3$ is added followed by the gradual addition of a heteroarylalkyl halide (Formula 7). The resulting reaction mixture is stirred at reflux under an inert atmosphere for a period of about 18 hours. The solution is cooled to about room temperature and the solvent removed. Water is added to residue and the resulting solution is extracted into a suitable solvent (such as, ethyl acetate), which yields a 1-(optionally substituted phenyl)-3-(optionally substituted heteroaryl)alkyl-pyrido[2,3-d]pyrimidine-2,4(1H,3H)-dione [Formula I, where Y is —C(O)—]. The desired product is purified by chromatography or recrystallization.

REACTION SCHEME B

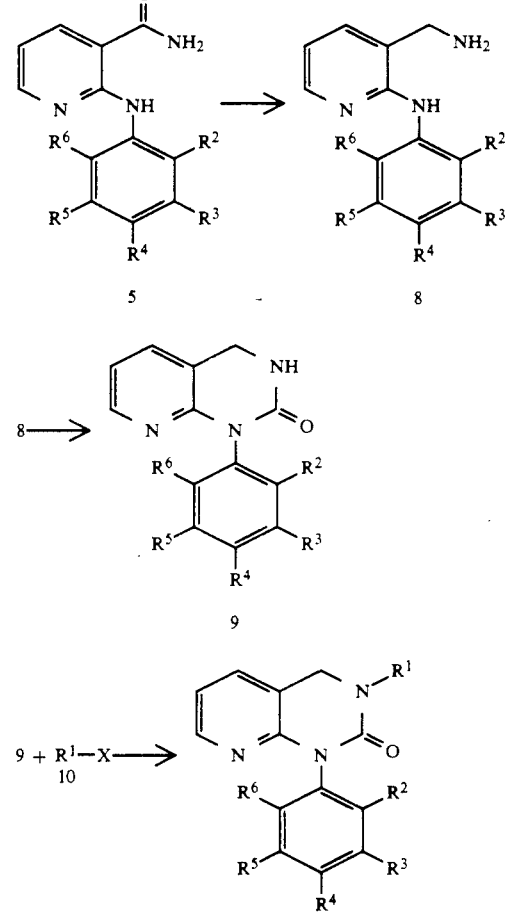

Formula I, where Y is —CH$_2$—

PREPARATION OF FORMULA 8

An optionally substituted 2-anilino-3-aminomethylpyridine (i.e., a compound of Formula 8) is prepared by dissolving a correspondingly optionally substituted 2-aryl-3-carbamoylpyridine (i.e., a compound of Formula 5, prepared, e.g., as described with reference to Reaction Scheme A) in an aprotic solvent (such as tetrahydrofuran or ethyl ether, preferably tetrahydrofuran) at a concentration of about 1 g/50 ml. The solution is cooled to about 0° C. The solution is added gradually to about 4.6 molar equivalent of a boron reducing agent (preferably a 1.0M solution of a $BH_3$-THF). The reaction mixture is cooled to about 0° C. under an inert atmosphere, stirred at about 0° C. for about 1 hour and refluxed for about 18 hours. 6M HCl is added to the reaction mixture until the pH is less than 7. The solvents are removed and a strong base [such as, sodium hydroxide (solid) or potassium hydroxide (solid)] is added to saturate the resulting residue. The base saturated residue is extracted into a suitable solvent, such as ethyl acetate. The organic phase is collected and upon removal of the solvents yields an optionally substituted 2-anilino-3-aminomethylpyridine (Formula 8). The product is used in the preparation of the corresponding compound of Formula 9 without further purification.

Alternatively, for substituents on the phenyl group less susceptible to reduction, a preparation using a stronger reducing agent (e.g., lithium aluminum hydride) is followed. An optionally substituted 2-anilino-3-aminomethylpyridine (i.e., a compound of Formula 8) is prepared by dissolving a correspondingly substituted 2-anilino-3-carbamoylpyridine (i.e., a compound of Formula 5, prepared, e.g., as described with reference to Reaction Scheme A) in an aprotic solvent (such as, tetrahydrofuran or ethyl ether, preferably tetrahydrofuran) at a concentration of about 1 g/50 ml and cooled to about 0° C. About 3.0 molar equivalent of a reducing agent, such as lithium aluminum hydride, is added to an aprotic solvent (such as, tetrahydrofuran or ethyl ether, preferably tetrahydrofuran) to form a suspension, which is heated to reflux. The solution of Formula 5 is added in a gradual manner to the refluxing suspension and stirred at reflux for about 18 hours. The reaction mixture is cooled to about room temperature and quenched. Residual solid material is removed and the mixture is concentrated by the removal of the solvents. The product is isolated by extraction into a suitable solvent (such as, ethyl acetate). The optionally substituted 2-anilino-3-aminomethylpyridine (Formula 8) is used in the preparation of the corresponding compound of Formula 9 without further purification. PREPARATION OF FORMULA 9

A 1-(optionally substituted phenyl)-pyrido[2,3-d]-pyrimidine-2(1H,3H)-one (Formula 9) is prepared from a compound of Formula 8 by following the procedures set forth in Reaction Scheme A for the preparation of compounds of Formula 6.

PREPARATION OF FORMULA I, WHERE Y IS -(CH₂)—

An optionally substituted 3-heteroarylalkyl-pyrido[2,3-d]pyrimidine-2(1H,3H)-one or 3-arylalkyl-pyrido[2,3-d]-pyrimidine-2(1H,3H)-one (Formula I, where Y is —CH₂—) is prepared by contacting a compound of Formula 9 and a correspondingly substituted heteroarylalkyl halide or arylalkyl halide (Formula 10), respectively according to the procedures set forth in Reaction Scheme A for the preparation of compounds of Formula I, where Y is —C(O) —.

STARTING MATERIALS FOR REACTION SCHEMES C, D, E, F, G, H, I

The starting materials for Reaction Schemes C, D, E, F, G, H, I and J are prepared following the procedures set forth in Reaction Scheme A (Formula I, where Y is —C(O) —) and Reaction Scheme B (Formula I, where Y is —CH₂—). 5-Methoxycarbonyl-2-methyl-pyridine (Formula 11) is obtained from the Aldrich Chemical Company.

REACTION SCHEME C

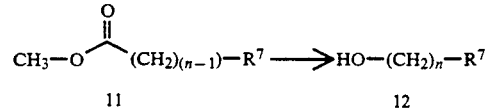

11        12

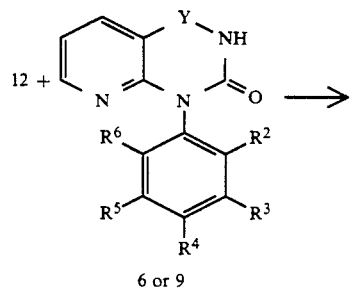

6 or 9

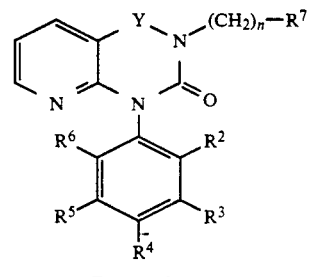

Formula I

PREPARATION OF COMPOUND 12

An optionally substituted methoxycarbonyl heteroaryl or optionally substituted methoxycarbonyl aryl compound (Formula 11, where $R^7$ is aryl or heteroaryl and n is 1 or 2) is dissolved in a solvent (e.g., toluene) and cooled to a temperature in the range of —50° C. to —100° C., preferably about —78° C. About 2 molar equivalent of a reducing agent, such as diisobutylaluminum hydride is added in a gradual manner to the solution. The reaction mixture is stirred for about 1 hour and then allowed to warm to about room temperature. The reaction mixture is then stirred for a period of about 10 to 26 hours, preferably about 18 hours. The reaction mixture is quenched by the addition of a solvent, such as methanol, in a gradual manner, followed by an acid (such as, 1M HCl). The desired product is isolated following extraction with a suitable organic solvent, yielding the corresponding optionally substituted hydroxymethyl hetero or optionally substituted hydroxymethyl aryl compound (Formula 2), which is used in the next step without further purification.

PREPARATION OF FORMULA I 1-(Optionally substituted phenyl)-3-(optionally substituted heteroaryl or aryl)alkyl-pyrido[2,3-d]pyrimidine-b 2,4(1H,3H)-dione and 1-(optionally substituted phenyl)-3-(optionally substituted heteroaryl or aryl)alkyl-pyrido[2,3-d]pyrimidine-2(1H,3H)-one can be prepared, for example, using methods described by Mitsunobu, O., et al., *Synthesis*, Jan. 1981, 1-28, or by the following procedures.

An optionally substituted pyrido[2,3-d]pyrimidine-2,4(1H,3H)-dione or pyrido[2,3-d]pyrimidine-2(1H,3H)-one [i.e., a compound of Formula 6 or Formula 9, prepared, e.g., as described in Reaction Scheme A and Reaction Scheme B, respectively] is dissolved in a solvent, such as, tetrahydrofuran or ethyl ether, preferably tetrahydrofuran. To this solution, about 1 molar equivalent of an optionally substituted hydroxymethyl hetero or optionally substituted hydroxymethyl aryl compound (i.e., Formula 12) and about 2 molar equivalent of triphenylphosphine is added under an inert atmosphere at about room temperature with stirring. About 2 molar equivalent of diisopropyl azodicarboxylate in a suitable solvent (e.g., tetrahydrofuran) is added to the stirring reaction mixture in a gradual manner. The reaction mixture is stirred at about room temperature under an inert atmosphere for a period of about 1.5 to 4.5 hours, preferably about 3 hours. The solvents are removed and the product is isolated and purified by chromatography yielding the corresponding 1-(optionally substituted phenyl)-3-(optionally substituted heteroaryl or aryl)alkyl-pyrido[2,3-d]pyrimidine-2,4(1H,3H)-dione and 1-(optionally substituted phenyl)-3-(optionally substituted heteroaryl or aryl)alkyl-pyrido-[2,3-d]pyrimidine-2(1H,3H)-one.

REACTION SCHEME D

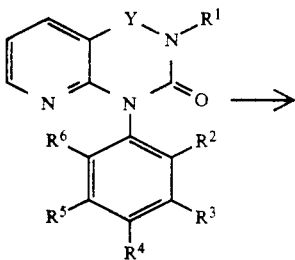

Formula I, where
$R^2$, $R^3$, $R^4$, $R^5$ and/or $R^6$
is —CN

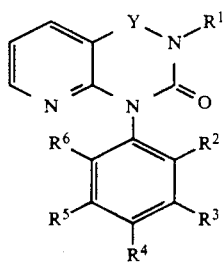

Formula I, where
$R^2$, $R^3$, $R^4$, $R^5$ and/or $R^6$
is —C(O)NH$_2$

PREPARATION OF FORMULA I, WHERE $R^3$ IS —C(O)NH$_2$

A 1-(optionally substituted cyanophenyl)-pyrido[2,3-d]-pyrimidine-2,4(1H,3H)-dione or pyrido[2,3-d]pyrimidine-2(1H,3H)-one [prepared according to Reaction Scheme A (where Y is —C(O)—), or Reaction Scheme B (where Y is —CH$_2$), —where the reactant of Formula 3 is a 2-, 3-, 4-, 5- or 6-cyanoaniline] is suspended in H$_2$O at a concentration of about 1.5 mmole/ml. To the suspension is added about 50 molar equivalents of acid of concentrated H$_2$SO$_4$. The suspension is heated to a temperature in the range of 60°-120° C., preferably about 90° C. for a period of about 1.5 to 4.5 hours, preferably about 3.0 hours. The reaction mixture is quenched with the addition of 10% Na$_2$CO$_3$, or the like, until the pH is neutral. The solvents are removed and the product is isolated and purified by chromatography yielding optionally substituted 1-(carbamoylphenyl)-pyrido[2,3-d]pyrimidine-2,4(1H, 3H)-dione or -pyrido[2,3-d]pyrimidine-2(1H,3H)-one (i.e., Formula I, where $R^2$, $R^3$, $R^4$, $R^5$ and/or $R^6$ is —C(O)NH$_2$).

REACTION SCHEME E

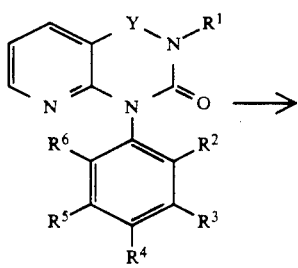

Formula I, where
$R^2$, $R^3$, $R^4$, $R^5$ and/or $R^6$
is —C(O)—OCH$_3$

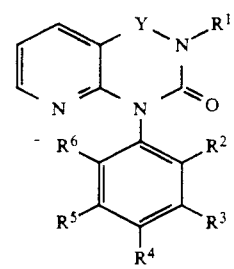

Formula I, where
$R^2$, $R^3$, $R^4$, $R^5$ and/or $R^6$
is —C(O)—NR$^8$R$^9$
where $R^8$ and $R^9$ are
independently hydrogen
or lower alkyl Aluminum amide, methylaluminum amide and dimethylaluminum amide reagents can be prepared, for example, using methods described by Weinreb. M., et al., *Synthetic Communications*, 12(13), 989-003 (1982), or by the following procedures.

PREPARATION OF ALUMINUM AMIDE REAGENT

Ammonium chloride is finely powdered and dissolved in a suitable solvent (e.g., toluene, at a concentration of about mmole/ml) and stirred under an inert atmosphere at about room temperature for about 30 minutes and then cooled to a temperature in the range of 0° to 5° C. About 1 molar equivalent of a solution of 2M trimethylaluminum (in toluene) is added, resulting in the formation of an aluminum amide reagent.

PREPARATION OF METHYLALUMINUM AMIDE AND DIMETHYLALUMINUM AMIDE REAGENT

Following the above procedures, methylaluminum amide reagent and a dimethylaluminum amide reagent is made by substituting ammonium chloride with methylammonium chloride, or dimethylammonium chloride, respectively.

PREPARATION OF FORMULA I, WHERE $R_2$, $R^3$, $R_4$, $R^5$ AND/OR $R^6$ IS $-C(O)NR^8R^9$, WHEREIN $R^8$ and $R^9$ ARE HYDROGEN A 1-(optionally substituted methoxycarbonylphenyl)-pyrido[2,3-d]pyrimidine-2,4(1H,3H)-dione or pyrido[-2,3-d]-pyrimidine-2(1H,3H)-one [i.e., Formula I, where $R^2$, $R^3$, $R_4$, $R^5$ and/or $R^6$ is $-C(O)-OCH_3$, prepared, e.g., as described with reference to Reaction Scheme A (where Y is $-C(O)-$) or Reaction Scheme B (where Y is $-CH_2-$)] is suspended in a suitable solvent (e.g., toluene at a concentration of about 1 mmole/10 ml). To the suspension is added about 3 molar equivalent of the aluminum amide reagent (as prepared above). The suspension is heated to a temperature in the range of 60° to 100° C., preferably about 80° C., and stirred for a period of about 3 to 7 hours, preferably about 5 hours. The reaction mixture is allowed to cool to about room temperature and quenched with an acid solution (e.g., 5% HCl) and then neutralized with a base. The solvents are removed and the product is isolated and purified by chromatography yielding an optionally substituted 1-(carbamoylphenyl)-pyrido[2,3-d] pyrimidine-2,4(1H, 3H)-dione or -pyrido[2,3-d]pyrimidine-2(1H,3H)-one (Formula I, where $R^2$, $R^3$, $R^4$, $R^5$ and/or $R^6$ is $-C(O)-NR^8R^9$, where $R^8$ and $R^9$ are hydrogen).

PREPARATION OF FORMULA I, WHERE $R^2$, $R^3$, $R^4$, $R^5$ AND/OR $R^6$ IS $-C(O)NR^8R^9$, WHEREIN $R^8$ IS HYDROGEN AND $R^9$ IS METHYL

Following the procedure set forth above, and substituting the methylaluminum amide reagent in place of the aluminum amide reagent, an optionally substituted 1-(methylcarbamoylphenyl)-pyrido[2,3-d]pyrimidine-2,4(1H,3H)-dione or -pyrido[2,3-d]pyrimidine-2(1H,3H)-one (Formula I, where $R^2$, $R^3$, $R^4$, $R^5$ and/or $R^6$ is $-C(O)-NR^8R^9$, where $R^8$ is hydrogen and $R^9$ is methyl) is obtained.

PREPARATION OF FORMULA I, WHEREIN $R_2$, $R^3$, $R^4$, $R_5$, or $R^6$ IS $C(O)NR^8R^9$, WHEREIN $R^8$ and $R^9$ ARE METHYL Following the procedure set forth above, and substituting the dimethylaluminum amide reagent in place of the aluminum amide reagent, an optionally substituted 1-(dimethylcarbamoylphenyl)-pyrido[2,3-d]pyrimidine-2,4(1H, 3H)-dione or -pyrido[2,3-d]pyrimidine-2(1H, 3H)-one (Formula I, where $R^2$, $R^3$, $R^4$, $R^5$ and/or $-C(O)-NR^8R^9$, where $R^8$ and $R^9$ are methyl) is obtained.

REACTION SCHEME F

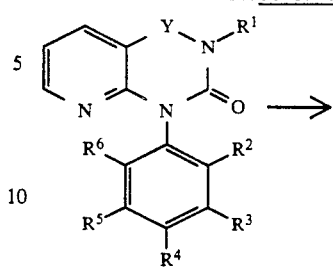

Formula I, where
$R^2$, $R^3$, $R^4$, $R^5$ and/or $R^6$
is $-S-CH_3$

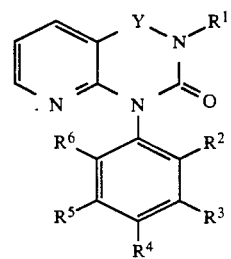

Formula I, where
$R^2$, $R^3$, $R^4$, $R^5$ and/or $R^6$
is $-S(O)-CH_3$

PREPARATION OF FORMULA I, WHERE $R^2$, $R^3$, $R^4$, $R^5$ AND/OR $R^6$ IS $-S(O)CH_3$

A 1-(Optionally substituted methylthiophenyl)-pyrido[2,3-d]pyrimidine-2,4(1H,3H)-dione or pyrido[2,3-d]-pyrimidine-2(1H, 3H)-one [i.e., Formula I, where $R^2$, $R^3$, $R^4$, $R^5$ and/or $R^6$ is $-SCH_3$, prepared according to Reaction Scheme A (where Y is $-C(O)-$) or Reaction Scheme B (where Y is $-CH_2-$)]is dissolved in a suitable solvent (e.g., methylene chloride) and cooled to about 0° C. To the solution is added about 1 molar equivalent of an oxidizing agent, such as, m-chloroperoxybenzoic acid. The reaction mixture is stirred at about 0° C. for about 2 hours. The reaction mixture is then washed (e.g., 10% solution of $Na_2SO_4$ followed by saturated $NaHCO_3$) and isolated, purified (by extraction into a suitable solvent) and dried yielding 1-(methylsulfinylphenyl)-pyrido[2,3-d]pyrimidine-2,4(1H,3H)-dione or -pyrido[2,3-d]-pyrimidine-2(1H,3H)-one (Formula I, where $R^2$, $R^3$, $R^4$, $R^5$ and/or $R^6$ is $-S(O)-CH_3$).

REACTION SCHEME G

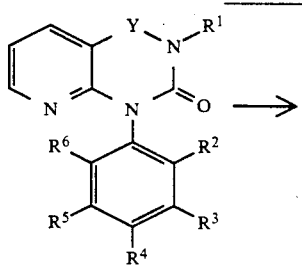

Formula I, where
$R^2$, $R^3$, $R^4$, $R^5$ and/or $R^6$
is $-S-CH_3$

-continued
REACTION SCHEME G

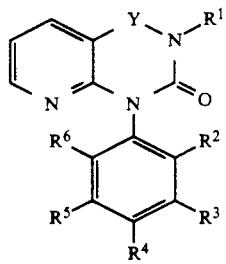

Formula I, where
$R^2$, $R^3$, $R^4$, $R^5$ and/or $R^6$
is —$S(O_2)$—$CH_3$

PREPARATION OF FORMULA I, WHERE $R^2$, $R^3$, $R^4$, $R^5$ AND/OR $R^6$ IS —$S(O_2)CH_3$

A 1-(optionally substituted methylthiophenyl)-pyrido[-2,3-d]pyrimidine-2,4(1H,3H)-dione or pyrido[2,3-d]-pyrimidine-2(1H,3H)-one [i.e., Formula I, where $R^2$, $R^3$, $R^4$, $R^5$ and/or $R^6$ is —$SCH_3$, prepared according to Reaction Scheme A (where Y is —C(O)—) or Reaction Scheme B (where Y is —$CH_2$—)] is dissolved in a suitable solvent (e.g., methanol) and cooled to about 0° C. To the solution is added about 3 molar equivalent of an oxidizing agent, such as, potassium peroxymonosulfate, i.e., $2KHSO_5$. $KHSO_4$. $K_2SO_4$, (this reagent is commercially available under the trademark of "OXONE®" from the Aldrich Chemical Company), preferably a 50% solution of $2KHSO_5$. $KHSO_4$. $K_2SO_4$ in $H_2O$. The reaction mixture was stirred at about room temperature for about 4 hours. The desired product was isolated and purified from the reaction mixture by extraction yielding the desired optionally substituted 1-(methylsulfonylphenyl)-pyrido[2,3-d]pyrimidine-2,4(1H, 3H)-dione dione or -pyrido[2,3-d]pyrimidine-2(1H, 3H)-one [Formula I, where $R^2$, $R^3$, $R^4$, $R^5$ and/or $R^6$ is —$S(O_2)$—$CH_3$].

REACTION SCHEME H

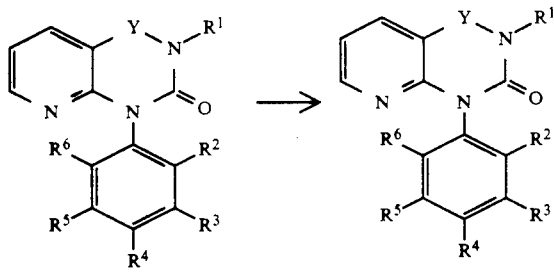

Formula I, where
$R^2$, $R^3$, $R^4$, $R^5$ and/or $R^6$
is —C(O)—$OCH_3$

Formula I, where
$R^2$, $R^3$, $R^4$, $R^5$ and/or $R^6$
is —$CH_2$—OH

PREPARATION OF FORMULA I, WHERE $R^2$, $R^3$, $R^4R^5$ AND/OR $R^6$ IS —$CH_2OH$

A 1-(optionally substituted methoxycarbonylphenyl)-pyrido[2,3-d]pyrimidine-2,4(1H,3H)-dione or pyrido[2,3-d]-pyrimidine-2(1H,3H)-one [i.e., Formula I, where $R^2$, $R^3$, $R^4$, $R^5$ and/or $R^6$ is —C(O)—$OCH_3$, repared according to Reaction Scheme A (where Y is —CO)— or Reaction Scheme B (where Y is —$CH_2$—)] is dissolved in a suitable solvent (e.g., toluene at a concentration of about 1 mmole/i10 ml) and cooled to a temperature in the range of —50° C. to —100° C., preferably about —78° C. under an inert atmosphere. To this solution is added about 2 molar equivalent of a reducing agent, such as, diisobutylaluminum hydride (i.e., DIBAL) in toluene, sodium borohydride complexes, preferably DIBAL in toluene at a temperature of about —78° C. in a gradual manner. After about 30 minutes. The reaction mixture is allowed to warm to about 0° C. and about 15 molar equivalent of sodium fluoride and $H_2O$ (about 1 ml/0.3 g of sodium fluoride) was added. The solution was stirred for about 5 minutes, allowed to warm to about room temperature and stirred vigorously for about 30 minutes The reaction mixture was extracted. The desired product is recovered from the organic phases yielding the optionally substituted 1-(hydroxymethylphenyl)-substituted-pyrido[-2,3-d]pyrimidine-2,4(1H,3H)-dione or -pyrido[2,3-d]-pyrimidine-2(1H, 3H)-one (Formula I, where $R^2$, $R^3$, $R^4$, $R^5$ and/or $R^6$ is —$CH_2OH$).

REACTION SCHEME I

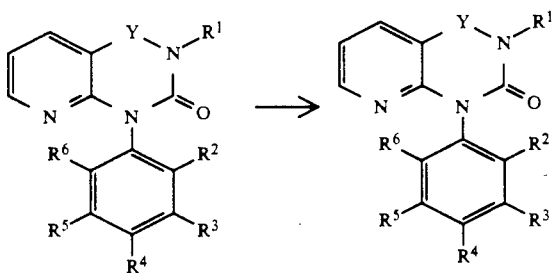

Formula I, where
$R^2$, $R^3$, $R^4$, $R^5$ and/or $R^6$
is —$NO_2$

Formula I, where
$R^2$, $R^3$, $R^4$, $R^5$ and/or $R^6$
is —$NH_2$

PREPARATION OF FORMULA I, WHERE $R^2$, $R^3$, $R^4$, $R^5$ AND/OR $R^6$ IS —$NH_2$.

1-(optionally substituted nitrophenyl)pyrido[2,3-d]-pyrimidine-2,4(1H,3H)-dione or pyrido[2,3-d]pyrimidine2(1H,3H)-one [i.e., Formula I, where $R^2$, $R^3$, $R^4$, $R^5$ and/or $R^6$ is —$NO_2$, prepared according to Reaction Scheme A (where Y is —C(O)') or Reaction Scheme B (where Y is —$CH_2$—)] is dissolved in a solvent (e.g., methanol) at a concentration of about 0.02 mmole/ml of solvent. A solution of reducing agent, such as hydrazine hydrate and Raney nickel reagent is prepared by combining about 1.5 molar equivalent of hydrazine hydrate, about 1.5 molar equivalent of Raney nickel and a solvent (e.g., methanol) at a concentration of about 0.02 mmole/ml of solvent and refluxing the mixture for a period of about 5 minutes. The starting material solution is added to the reducing agent in a dropwise manner, the reaction mixture is then refluxed for a period of about 1 hour. The reaction mixture is filtered (e.g., Celite or the like) and washed with a solvent (e.g., methanol). The solvents are removed and the product is further purified by preparative thin-layer chromatography yielding an optionally substituted 1-(aminophenyl)-pyrido[2,3-d]pyrimidine-2,4(1H,3H)-dione or -pyrido[2,3-d]pyrimidine-2(1H,3H)-one (Formula I, where $R^2$, $R^3$, $R^4$, $R^5$ and/or $R^6$ is —$NH_2$).

REACTION SCHEME J

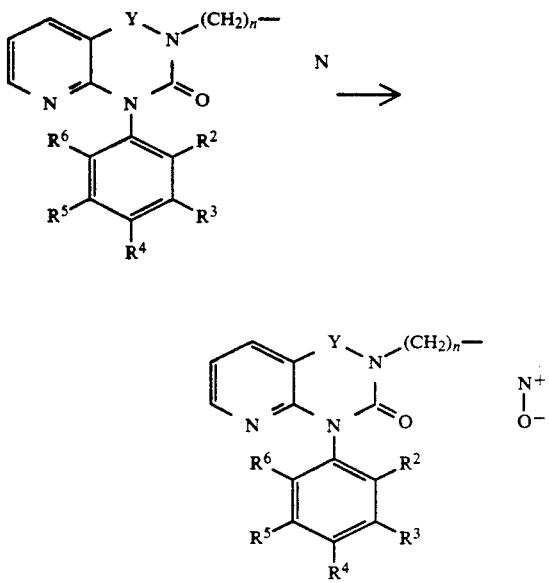

PREPARATION OF N-OXIDE COMPOUNDS FORMULA I

A 1-(optionally substituted phenyl)pyrido[2,3-d]-pyrimidine-2,4(1H,3H)-dione or pyrido[2,3-d]pyrimidine2(1H,3H)-one [i.e., Formula I, where $R^7$ is a N-heteroaryl, prepared according to Reaction Scheme A (where Y is —C(O) —) or Reaction Scheme B (where Y is —CH$_2$)] is dissolved in a suitable solvent (e.g., methylene chloride or tetrahydrofuran) and cooled to about 0° C. To the solution is added about 0.5 molar equivalent of an oxidizing reagent, such as m-chloroperoxybenzoic acid. The reaction mixture is stirred for about 1 hour at about 0° C., and allowed to warm to about room temperature and stirred for a period of about 12 to 24 hours, preferably about 18 hours. The reaction mixture is treated with about 10 molar equivalent (molar excess) of an appropriate quenching reagent (e.g., Na$_2$SO$_4$, Na$_2$CO$_3$) and stirred for a period of about 1 to 2 hours, preferably about 1.5 hours. The desired product is isolated as a solid from the reaction mixture by filtration and is washed and dried yielding the corresponding desired N-oxide of the pyrido[2,3-d]pyrimidine-2,4(1lH,3H)-dione or -pyrido[2,3-d]-pyrimidine-2(1H,3H)-one starting material.

PREPARATION OF THE SALT OF FORMULA I

The pharmaceutically acceptable salts of Formula I are prepared by dissolving a compound of Formula I in a suitable solvent (such as methanol) adding 1 to 3 molar equivalents (preferably about two molar equivalent) of an appropriate acid (such as hydrochloric acid) or base (such as an alkaline earth hydroxide, e.g., lithium hydroxide, calcium hydroxide, potassium hydroxide, sodium hydroxide or the like; preferably sodium hydroxide) and stirring. The salt is isolated by lyophilization or by precipitation, using techniques that will be apparent to those skilled in the art.

PREFERRED COMPOUNDS

Presently preferred are the compounds of Formula I where Y is C(O), particularly where $R^7$ is pyridyl (especially 4-pyridyl or 3-pyridyl), $R^2$, $R^4$, $R^5$ and $R^6$ are hydrogen, n is one and $R^3$ is an electron withdrawing substituent, such as halo (especially chloro), nitro or methoxycarbonyl.

Especially preferred is the compound of Formula I that is, 1-(3-nitrophenyl)-3-(3-pyridylmethyl)-pyrido[2,3-d]-pyrimidine-2,4(1H,3H)-dione.

Especially preferred is the compound of Formula I that is 1-(3-nitrophenyl)-3-(4-pyridylmethyl)pyrido[2,3-d]-pyrimidine-2,4(1H,3H)-dione.

Especially preferred is the compound of Formula I that is 1-(3-methoxycarbonylphenyl)-3-(3-pyridylmethyl)pyrido[2,3-d]pyrimidine-2,4(1H,3H)-dione.

Especially preferred is the compound of Formula I that is 1-(3-methoxycarbonylphenyl)-3-(4-pyridylmethyl)pyrido[2,3-d]pyrimidine-2,4(1H,3H)-dione.

Especially preferred is the compound of Formula I that is 1-(3-chlorophenyl)-3-(3-pyridylmethyl)-pyrido[2,3-d]-pyrimidine-2,4(1H,3H)-dione.

Especially preferred is the compound of Formula I that is 1-(3-chlorophenyl)-3-(4-pyridylmethyl)-pyrido[2,3-d]- -pyrimidine-2,4(1H,3H)-dione.

PREFERRED PROCESSES AND LAST STEPS

A preferred process for making optionally substituted 1-aryl-3-(heteroarylalkyl)pyrido[2,3-d]pyrimidine-2,4(1H, 3H)-dione or 1-aryl-3-(heteroarylalkyl)-pyrido[2,3-d]pyrimidine-2(1H,3H)-one entails contacting a suitably substituted pyrido[2,3-d]pyrimidine-2,4(1H,3H)-dione pyrido[2,3-d]-pyrimidine-2 -pyrimidine-2(1H,3H)-one with a suitably substituted heteroarylalkyl halide in the presence of a strong base.

A preferred process for making optionally substituted 1-aryl-3-(2,5-dimethylpyridylmethyl)pyrido[2,3-d]pyrimidine-2,4(1H,3H)-dione or 1-aryl-3-(2,5-dimethylpyridylmethyl)pyrido[2,3-d]pyrimidine-2(1H,3H)-one entails contacting a suitably substituted pyrido[2,3-d]pyrimidine-2,4(1H,3H)-dione or pyrido[2,3-d]pyrimidine-2(1H,3H)-one with a suitably substituted heteroarylalkyl alcohol in the presence of intermolecular dehydration reagent (e.g., the combination of DIAD/triphenylphosphine).

A preferred process for making optionally substituted 1-(carbamoylphenyl)-3-(heteroarylalkyl)pyrido[2,3-d]-pyrimidine-2,4(1H,3H)-dione or 1-(carbamoylphenyl)-3-(heteroarylalkyl)pyrido[2,3-d]pyrimidine-2(1H,3H)-one entails contacting a suitably substituted 1-(cyanophenyl)-3-(heteroarylalkyl)pyrido[2,3-d]pyrimidine-2,4(1H,3H)-dione or 1-(cyanophenyl)-3-(heteroarylalkyl)pyrido[2,3-d]pyrimidine-2(1H,3H)-one with a strong acid.

A preferred process for making optionally substituted 1-(N-alkylcarbamoylphenyl)-3-(heteroarylalkyl)-pyrido[2,3-d]-pyrimidine-2,4(1H,3H)-dione or 1-(N-alkylcarbamoylphenyl)-3(heteroarylalkyl)pyrido[2,3-d]pyrimidine-2(1lH,3H)-one entails contacting a suitably substituted 1-(methoxycarbonylphenyl)-3-(heteroarylalkyl)pyrido[2,3-d]pyrimidine-2,4(lH, 3H)-dione or 1-(3-methoxycarbonylphenyl)-3-(heteroarylalkyl)pyrido[2,3-d]pyrimidine-2(1H,3H)-one with a suitably substituted aluminum amide reagent.

A preferred process for making optionally substituted 1-(methylsulfinylphenyl)-3-(heteroarylalkyl)pyrido[2,3-d]-pyrimidine-2,4(1H,3H)-dione or 1-(methylsulfinyl-phenyl)-3(heteroarylalkyl)pyrido[2,3-d]pyrimidine-2(1H,3H)-one entails contacting a suitably substituted 1-(methylthiophenyl)-3-(heteroarylalkyl)pyrido[2,3-d]pyrimidine-2,4(1H,3H)-dione or 1-(methylthiophenyl)-3-(heteroarylalkyl)pyrido[2,3-d]-pyrimidine-2(1H,3H)-one with an oxidizing reagent.

A preferred process for making optionally substituted 1-(methylsulfonylphenyl)-3-(heteroarylalkyl)-pyrido[2,3-d]-pyrimidine-2,4(1H,3H)-dione or 1-(methylsulfonylphenyl)-3(heteroarylalkyl)pyrido[2,3-d]pyrimidine-2(1H,3H)-one entails contacting a suitably substituted 1-(methylthiophenyl)-3(heteroarylalkyl)-pyrido[2,3-d]pyrimidine-2,4(1H,3H)-dione or 1-(methylthiophenyl)-3-(heteroarylalkyl)pyrido[2,3-d]-pyrimidine-2(1H,3H)-one with an oxidizing reagent.

A preferred process for making optionally substituted 1-(hydroxymethylphenyl)-3-(heteroarylalkyl)-pyrido[2,3-d]-pyrimidine-2,4(1H,3H)-dione or 1-(hydroxymethylphenyl)-3(heteroarylalkyl)pyrido[2,3-d]pyrimidine-2(1H, 3H)-one entails contacting a suitably substituted 1-(methoxycarbonylphenyl)-3-(heteroarylalkyl)pyrido[2,3-d]pyrimidine-2,4(1H,3H)-dione or 1-(methoxycarbonylphenyl)-3-(heteroarylalkyl)pyrido[2,3-d]pyrimidine-2(1H,3H)-one with a reducing agent.

A preferred process for making optionally substituted 1-(aminophenyl)-3-(heteroarylalkyl)pyrido[2,3-d]pyrimidine-2,4(1H,3H)-dione or 1-(aminophenyl)-3(heteroarylalkyl)pyrido[2,3-d]pyrimidine-2(1H,3H)-one entails contacting a suitably substituted 1-(nitrophenyl)-3(heteroarylalkyl)pyrido[2,3-d]pyrimidine-2,4(1H,3H)-dione or 1-(nitrophenyl)-3-(heteroarylalkyl)pyrido[2,3-d]pyrimidine-2(1H, 3H)-one with a reducing agent.

UTILITY, TESTING AND ADMINISTRATION
GENERAL UTILITY

The compounds of this invention, including the pharmaceutically acceptable salts, esters and ethers thereof, and the compositions containing them are particularly useful as anti-inflammatory, immunosuppressive, anti-allograft rejection, anti-graft-vs-host disease, anti-allergic agents (e.g., asthma, rhinitis and atopic dermatitis), anti-autoimmune disease or analgetic agents. The compounds of this invention act as PDE IV selective inhibitors, thereby modulating cAMP levels. Thus, these compounds are of use for the treatment of cAMP related conditions or diseases, particularly those that are modulated by leukocyte cAMP.

For example, inflammation, autoimmune diseases, graft-vs-host disease and allograft rejection are conditions that are manifested by the proliferation of lymphocytes. The proliferation is triggered by the presence of cAMP at specific levels. Inhibition of lymphocyte proliferation is accomplished by increasing levels of cAMP resulting from the inhibition of lymphocyte phosphodiesterase.

TESTING

Potency and selectivity of compounds as inhibitors of PDE IV is determined by following, for example, the procedures described in Example 23, or modifications thereof.

The immunomodulatory and anti-inflammatory activity of the compounds of the invention can be determined by a variety of assays utilizing both in vitro and in vivo procedures.

Inhibition of the proliferation of lymphocytes in response to mitogenic stimulation is determined by the procedures described by Greaves, et al. ["Activation of human T and B lymphocytes by polyclonal mitogens," *Nature*, 248, 698-701 (1974)], or modifications thereof (see, Example 24).

Inhibition of lymphocyte activation in response to antigenic challenge is determined in vitro by inhibition of a cytolytic T-cell assay (CTL) as described by Wunderlich, et al., *Nature* (1970), Vol. 228, p. 62, or a modification thereof.

Immune modulation is determined by in vivo procedures utilizing the Jerne Hemolytic Plaque Assay, [Jerne, et al., "The agar plaque technique for recognizing antibody producing cells," *Cell-bound Antibodies*, Amos, B. and Kaprowski, H. editors (Wistar Institute Press, Philadelphia) 1963, p. 109] or a modification thereof (see, Example 25).

Anti-inflammatory activity is determined by the Arachidonic Acid-Induced Mouse Ear Edema Assay [Young, et al, *J. Invest. Derm.*, 82: 367-371 (1984) ] (see, Example 26).

Anti-inflammatory activity is also determined by the Adjuvant Arthritis assay [Pearson, C. M., *Proc. Soc. Exp. Biol. Med.*, 91:95-101 (1956)], or modifications thereof (see Example 27).

Anti-autoimmune activity in treating autoimmune disease can be determined utilizing the survivability of MRL/lpr mice described by Theofilopoulos, et al., *Advances in Immunology*, Vol 37 pages 269-390 (1985)

Analgetic activity is determined by the Phenylquinone-induced Mouse Writhing Assay [Hendershot, et al., *J. Pharmacol. Exp. Ther.*, 125: 237-240 (1959)] (see Example 29).

ADMININISRATION

The compounds of this invention are administered at a therapeutically effective dosage, i.e., that amount which, when administered to a mammal in need thereof, is sufficient to effect treatment, as described above (for example, to reduce or otherwise treat inflammation, pain and/or pyrexia in the mammal). Administration of the active compounds and salts described herein can be via any of the accepted modes of administration for agents that serve similar utilities.

The level of the drug in a formulation can vary within the full range employed by those skilled in the art, e.g., from about 0.01 percent weight (%w) to about 99.99%w of the drug based on the total formulation and about 0.01% w to 99.99% w excipient. Preferably the drug is present at a level of about 10% w to about 70% w.

Generally, an acceptable daily dose is of about 0.001 to 50 mg per kilogram body weight of the recipient per day, preferably about 0.05 to 25 mg per kilogram body weight per day, and most preferably about 0.01 to 10 mg per kilogram body weight per day. Thus, for administration to a 70 kg person, the dosage range would be about 0.07 mg to 3.5 g per day, preferably about 3.5mg to 1.75 g per day, and most preferably about 0.7 mg to 0.7 g per day depending upon the individuals and disease state being treated. Such use optimization is well within the ambit of those of ordinary skill in the art.

Administration can be via any accepted systemic or local route, for example, via parenteral, oral (particularly for infant formulations), intravenous, nasal, transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient and an active compound of Formula I and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's PharmaceuticalI Sciences" by E. W. Martin.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a compound of Formula I. The level of the drug in a formulation can vary within the full range employed by those skilled in the art, e.g., from about 0.01 percent weight (% w) to about 99.99% w of the total formulation and about b 0.01% w to 99.99% w excipient. Preferably, the formulation will be about 3.5 to 60% by weight of the pharmaceutically active compound, with the rest being suitable pharmaceutical excipients.

INTRAVENOUS ADMINISTRATION

Intravenous injection has proven to be an important route of administration for therapeutic agents. The compounds of the present invention can be administered via this route, for example, by dissolving the compound, salt, ester or ether in a suitable solvent (such as water or saline) or incorporation in a liposomal formulation followed, by dispersal into an acceptable infusion fluid. A typical daily dose of a compound of the invention can be administered by one infusion, or by a series of infusions spaced over periodic intervals.

ORAL ADMINISTRATION

Oral administration can be used to deliver the compound of Formula I using a convenient daily dosage regimen which can be adjusted according to the degree of affliction or for renal impairment, or to compensate for the toxic effects of other medications administered contemporaneously. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/wt % and 99.99 wt/wt % of the compound of Formula I, but preferably such compositions will contain between 25 wt/wt % and about 80 wt/wt %.

Preferably the compositions will take the form of a capsule, pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like. For oral administration to infants, a liquid formulation (such as a syrup or suspension) is preferred.

LIPOSOMAL FORMULATIONS

Pharmaceutical formulations based on liposomes have recently reached human clinical trials. Their benefits are believed related to favorable changes in tissue distribution and pharmacokinetic parameters that result from liposome entrapment of drugs, and may be applied to the compounds of the present invention by those skilled in the art.

The formulations can be designed to either target drug to disease sites [see: Lopez-Berestein et al., *J. Infect. Dis.*, 151: 704–710 (1985); Gotfredsen et al., *Biochemical Pharmacology*, 32: 3389-3396 (1983)]; or to the reticuloendothelial system [see Eppstein et al., *Int. J. Immunotherapy*, 2:115-126 (1986)], to increase duration of drug action [see: Gabizon et al., *Cancer Res.*, 42: 4734 (1982); Eppstein et al., *Delivery Systems for Peptide Drugs*, Eds. S. S. Davis, L. Illum and E. Tomlinson, Plenum Pub. Corp., New York, pp. 277-283; C. A. Hunt, *Biochemica et Biophysica Acta.*, 719: 450–463 (1982); and Senior et al., *Biochemica et Biophysica Acta.*, 839: 1–8 (1985)], or to divert a drug away from organs that are particularly sensitive to its toxic effects [see: Weinstein et al., *Pharmac. Ther.*, 24: 207-233 (1983); Olson et al., *Eur. J. Cancer Clin. Oncol.*, 18: 167-176 (1982); and Gabzion et al. supra.].

Controlled release liposomal liquid pharmaceutical formulations for injection or oral administration are described in U.S. Pat. No. 4,016,100. Liposomal applications for oral drug delivery of a lyophilized liposome/peptide drug mixture filled into intesting capsules have also been suggested, see U.S. Pat. No. 4,348,384. The foregoing are incorporated herein by reference.

SUPPOSITORIES

For systemic administration via suppository, traditional binders and carriers include, for example, polyalkaline glycol or triglycerides [e.g., PEG 1000 (96%) and PEG 4000 (4%)]. Such suppositories may be formed from mixtures containing active ingredients in the range of from about 0.5 wt/wt % to about 10 wt/wt %; preferably from 1 wt/wt % to about 2 wt/wt %.

LIQUIDS

Liquid pharmaceutically administrable compositions can, for example, be prepared by dissolving, dispersing, etc. an active compound (about 0.5% to about 20%), as described above, and optional pharmaceutical adjuvants in a carrier, such as, for examle, water, saline, aqueous dextrose, glycerol, ethanol and the like, to thereby form a solution or suspension.

Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

EXAMPLES

The following examples are given to enable those skilled in the art to more clearly understand and to practice the present invention. They should not be considered as limiting the scope of the invention, but merely as being illustrative and representative thereof.

EXAMPLE 1

Preparation of Potassium 2-Chloronicotinate

1. Formula 2

2-Chloro nicotinic acid (50 g, 317.5 mmole) was suspended in ethanol (1400 ml). To this solution potassium hydroxide pellets (20 g, 349.5 mmole) were added gradually over 30 minutes with stirring at room temperature. The suspension was stirred for 18 hours during which a clear solution was formed followed by the precipitation of a white solid, i.e., the potassium salt of the 2-chloro nicotinic acid. Three-quarters of the solvent was removed. The precipitate was isolated, washed with ethyl ether, and air dried yielding 58 g (296.5 mmole, 93% yield) of potassium 2-chloro nicotinate (mp >270° C.).

EXAMPLE 2

Preparation of 2-(3-Nitroanilino)-3-Carboxypyridine

2A. Formula 4, Where $R^3$ is Nitro

Potassium-2-chloro-nicotinate (89 g, 455 mmole) was suspended in 630 ml of dimethylformamide. To this suspension was added 3-nitroaniline (75.3 gm, 546 mmole), cupric acetate (5.1 g, 25.5 mmole) and N-ethyl morpholine (52.3 g, 455 mmoles). The suspension was refluxed with stirring under $N_2$ for 4 hours. The reaction mixture was cooled to room temperature and the pH was adjusted to 4–5 by the addition of 6M HCl. A yellow precipitate was isolated from the reaction mixture, washed with water and air dried yielding 66.3 g (256 mmole, 56% yield) of 2-(3-nitroanilino)-3-carboxypyridine (mp 262°–264° C.).

2B. Preparation of Other Compounds of Formula 4, Varying $R^2$–$R^6$.

By following the procedures of Example 2A and substituting for 3-nitroaniline with the following:
4-methyl-3-nitroaniline,
3-cyanoaniline,
aniline,
3-chloroaniline,
3-methoxycarbonylaniline,
3-methylthioaniline,
3-fluoroaniline,
2,4-dimethyl-3-methoxycarbonylaniline,
2,4-dimethyl-3-nitroaniline,
2,4-dimethylaniline,
3,4-dichloroaniline,
3-methylcarbonylaniline,
3,5-dibromoaniline,
2,4,6-trifluoro-3-ethylaniline,
2,4-dimethyl-3-methylcarbonylaniline,
2,6-difluoro-4-propylaniline,
2,6-difluoro-4-cyanoaniline, and
3,5-dimethylthioaniline;
there are obtained the following compounds:
1-(4-methyl-3-nitroanilino)-3-carboxypyridine,
1-(3-cyanoanilino)-3-carboxypyridine, mp 246°–247° C.,
1-anilino-3-carboxypyridine,
1-(3-chloroanilino)-3-carboxypyridine,
1-(3-methoxycarbonylanilino)-3-carboxypyridine,
1-(3-methylthioanilino)-3-carboxypyridine, mp 170°–172° C.,
1-(3-fluoroanilino)-3-carboxypyridine,
1-(2,4-dimethyl-3-methoxycarbonylanilino)-3-carboxypyridine,
1-(2,4-dimethyl-3-nitroanilino)-3-carboxypyridine,
1-(2,4-dimethylanilino)-3-carboxypyridine,
1-(3,4-dichloroanilino)-3-carboxypyridine,
1-(3-methylcarbonylanilino)-3-carboxypyridine,
1-(3,5-dibromoanilino)-3-carboxypyridine,
1-(2,4,6-trifluoro-3-ethylanilino)-3-carboxypyridine,
1-(2,4-dimethyl-3-methylcarbonylanilino)-3-carboxypyridine,
1-(2,6-difluoro-4-propylanilino)-3-carboxypyridine,
1-(2,6-difluoro-4-cyanoanilino)-3-carboxypyridine, and
1-(3,5-dimethylthioanilino)-3-carboxypyridine.

EXAMPLE 3

Preparation of 2-(3-Nitroanilino)-3-Carbamoylpyridine

3A. Formula 5, where $R^3$ is Nitro 2-(3-Nitroanilino)-3-carboxypyridine (66.3 g, 256 mmole) was suspended in benzene (1100 ml). To this suspension, thionyl chloride (66.3 ml) was added dropwise with stirring. The reaction mixture was refluxed for 4 hours. Excess solid material was filtered from the solution while the solution was still hot. The solvent was stripped from the solution and 69.7 g (251 mmole, 98% yield) of crude 2-(3-nitroanilino)-3-chloroformylpyridine (i.e., an acid chloride) as a solid was recovered, which was taken to the next step without further purification.

The 2-(3-nitroanilino)-3-chloroformylpyridine was dissolved in tetrahydrofuran (2000 ml) and 70 ml of 30% solution of $NH_4OH$ was added dropwise with stirring to the reaction mixture. The reaction mixture was stirred at room temperature for 18 hours. Water was added to the mixture to dissolve the solid ammonium chloride that was formed. The tetrahydrofuran was removed, and the resulting aqueous slurry was filtered and washed yielding a yellow solid. The solid was washed with water and air dried yielding 64.8 g (250 mmole, 99% yield) of 2-(3-nitroanilino)-3-carbamoylpyridine (mp 240°–241° C.).

3B. Preparation of Other Compounds of Formula 5

By following the procedures of Example 3A and substituting 2-(3-nitroanilino)-3-carboxypyridine with the following:
1-(4-methyl-3-nitroanilino)-3-carboxypyridine,
1-(3-cyanoanilino)-3-carboxypyridine,
1-anilino-3-carboxypyridine,
1-(3-chloroanilino)-3-carboxypyridine,
1-(3-methoxycarbonylanilino)-3-carboxypyridine,
1-(3-methylthioanilino)-3-carboxypyridine,
1-(3-fluoroanilino)-3-carboxypyridine,
1-(2,4-dimethyl-3-methoxycarbonylanilino)-3-carboxypyridine,
1-(2,4-dimethyl-3-nitroanilino)-3-carboxypyridine,
1-(2,4-dimethylanilino)-3-carboxypyridine,
1-(3,4-dichloroanilino)-3-carboxypyridine,
1-(3-methylcarbonylanilino)-3-carboxypyridine,
1-(3,5-dibromoanilino)-3-carboxypyridine,
1-(2,4,6-trifluoro-3-ethylanilino)-3-carboxypyridine,
1-(2,4-dimethyl-3-methylcarbonylanilino)-3-carboxypyridine,
1-(2,6-difluoro-4-cyanoanilino)-3-carboxypyridine, and
1-(3,5-dimethylthioanilino)-3-carboxypyridine;

there are obtained the following compounds:
1-(4-methyl-3-nitroanilino)-3-carbamoylpyridine,
1-(3-cyanoanilino)-3-carbamoylpyridine, mp 218°–219° C.,
1-anilino-3-carbamoylpyridine,
1-(3-chloroanilino)-3-carbamoylpyridine,
1-(3-methoxycarbonylanilino)-3-carbamoylpyridine,
1-(3-methylthioanilino)-3-carbamoylpyridine,
1-(3-fluoroanilino)-3-carbamoylpyridine,
1-(2,4-dimethyl-3-methoxycarbonylanilino)-3-carbamoylpyridine,
1-(2,4-dimethyl-3-nitroanilino)-3-carbamoylpyridine,
1-(2,4-dimethylanilino)-3-carbamoylpyridine,
1-(3,4-dichloroanilino)-3-carbamoylpyridine,
1-(3-methylcarbonylanilino)-3-carbamoylpyridine,
1-(3,5-dibromoanilino)-3-carbamoylpyridine,
1-(2,4,6-trifluoro-3-ethylanilino)-3-carbamoylpyridine,
1-(2,4-dimethyl-3-methylcarbonylanilino)-3-carbamoylpyridine,
1-(2,6-difluoro-4-propylanilino)-3-carbamoylpyridine,
1-(2,6-difluoro-4-cyanoanilino)-3-carbamoylpyridine, and
1-(3,5-dimethylthioanilino)-3-carbamoylpyridine.

EXAMPLE 4

Preparation of 1-N-(3-Nitrophenyl)pyrido[2,3-d]pyrimidine-2,4(1H,3H)-dione

4A. Formula 6, Where Y is —C(O)— and $R^3$ is Nitro 2-(3-Nitroanilino)-3-carbamoylpyridine (20 g, 77.5 mmole) was dissolved in tetrahydrofuran (2000 ml). Sodium hydride (60% dispersion in oil) (12.4 g, 310.0 mmole) was washed in hexanes and added to the solution. The solution was stirred for 5 minutes at room temperature under an inert atmosphere. To the solution, CDI (1,1'-carbonyldiimidazole) (18.8 g, 116.2 mmole) was added in a gradual manner over a period of 15 minutes, the resulting mixture was stirred at room temperature for 1 hour and subsequently refluxed for 24 hours. The solvent was removed resulting in a brown residue. Water was added to the residue and the resulting solution was extracted with ethyl acetate (5×300 ml). The phases were separated and the product was recrystallized from EtOAc/Et₂O yielding a 12 g (42.4 mmole, 54.5% yield) of 1-N-(3-nitrophenyl)pyrido[2,3-d]pyrimidine-2,4(1H,3H)-dione (mp 262°–263° C.).

4B. Preparation of Other Compounds of Formula 6

By following the procedures of Example 4A and substituting 2-(3-nitroanilino)-3-carbamoylpyridine with the following:
1-(4-methyl-3-nitroanilino)-3-carbamoylpyridine,
1-(3-cyanoanilino)-3-carbamoylpyridine,
1-anilino-3-carbamoylpyridine,
1-(3-chloroanilino)-3-carbamoylpyridine,
1-(3-methoxycarbonylanilino)-3-carbamoylpyridine,
1-(3-methylthioanilino)-3-carbamoylpyridine,
1-(3-fluoroanilino)-3-carbamoylpyridine,
1-(2,4-dimethyl-3-methoxycarbonylanilino)-3-carbamoylpyridine,
1-(2,4-dimethyl-3-nitroanilino)-3-carbamoylpyridine,
1-(2,4-dimethylanilino)-3-carbamoylpyridine,
1-(3,4-dichloroanilino)-3-carbamoylpyridine,
1-(3-methylcarbonylanilino)-3-carbamoylpyridine,
1-(3,5-dibromoanilino)-3-carbamoylpyridine,
1-(2,4,6-trifluoro-3-ethylanilino)-3-carbamoylpyridine,
1-(2,4-dimethyl-3-methylcarbonylanilino)-3-carbamoylpyridine,
1-(2,6-difluoro-4-propylanilino)-3-carbamoylpyridine,
1-(2,6-difluoro-4-cyanoanilino)-3-carbamoylpyridine, and
1-(3,5-dimethylthioanilino)-3-carbamoylpyridine;
there are obtained the following compounds:
1-(4-methyl-3-nitrophenyl)pyrido[2,3-d]pyrimidine-2,4(1H,3H)-dione,
1-(3-cyanophenyl)pyrido[2,3-d]pyrimidine-2,4(1H,3H)-dione, mp 88°–89° C.,
1-phenyl-pyrido[2,3-d]pyrimidine-2,4(1H,3H)-dione,
1-(3-chlorophenyl)pyrido[2,3-d]pyrimidine-2,4(1H,3H)-dione,
1-(3-methoxycarbonylphenyl)pyrido[2,3-d]pyrimidine-2,4(1H,3H)-dione,
1-(3-methylthiophenyl)pyrido[2,3-d]pyrimidine-2,4(1H,3H)-dione, mp is greater than 280° C.,
1-(3-fluorophenyl)pyrido[2,3-d]pyrimidine-2,4(1H,3H)-dione,
1-(2,4-dimethyl-3-methoxycarbonylphenyl)pyrido[2,3-d]pyrimidine-2,4(1H,3H)-dione,
1-(2,4-dimethyl-3-nitrophenyl)pyrido[2,3-d]pyrimidine-2,4(1H,3H)-dione,
1-(2,4-dimethylphenyl)pyrido[2,3-d]pyrimidine-2,4(1H,3H)-dione,
1-(3,4-dichlorophenyl)pyrido[2,3-d]pyrimidine-2,4(1H,3H)-dione,
1-(3-methylcarbonylphenyl)pyrido[2,3-d]pyrimidine-2,4(1H,3H)-dione,
1-(3,5-dibromophenyl)pyrido[2,3-d]pyrimidine-2,4(1H,3H)-dione,
1-(2,4,6-trifluoro-3-ethylphenyl)pyrido[2,3-d]pyrimidine-2,4(1H,3H)-dione,
1-(2,4-dimethyl-3-methylcarbonylphenyl)pyrido[2,3-d]pyrimidine-2,4(1H,3H)-dione,
1-(2,6-difluoro-4-propylphenyl)pyrido[2,3-d]pyrimidine-2,4(1H,3H)-dione,
1-(2,6-difluoro-4-cyanophenyl)pyrido[2,3-d]pyrimidine-2,4(1H,3H)-dione, and
1-(3,5-dimethylthiophenyl)pyrido[2,3-d]pyrimidine-2,4(1H,3H)-dione.

EXAMPLE 5

Preparation of 1-(3-Nitrophenyl)-3-(4-pyridylmethyl)pyrido[2,3-d]pyrimidine-2,4(1H,3H)-dione 5A. Formula I, Where Y is —C(O)—, $R^1$ is 4-Pyridylmethyl and $R^3$ is Nitro 1-(3-Nitrophenyl)pyrido[2,3-d]pyrimidine-2,4(1H,3H)-dione (12.0 g, 42.2 mmoles) was added into 2 liters of acetone and warmed with stirring until a solution was formed. To the solution was added powdered potassium carbonate (23.4 g, 169.3 mmoles) and 4-chloromethylpyridine hydrochloride (10.4 g, 63.4 mmoles). The solution was stirred at reflux temperature for 18 hours. The solution was filtered while hot. Three quarters of the solvent was removed resulting in the formation of a precipitate. The solution was cooled to 0° C. and the precipitate was removed by filtration. The precipitate was washed with ethyl ether and air dried yielding 10.0 g (26.6 mmole, 63% yield) of 1-(3-nitrophenyl)-3-(4-pyridylmethyl)pyrido[2,3-d]pyrimidine-2,4(1H,3H)-dione (mp 207°–209° C.).

5B. Formula I, Varying $R^2$–$R^6$.

By following the procedures of Example 5A and substituting 1-(3-nitrophenyl)pyrido[2,3-d]pyrimidine-2,4(1H,3H)-dione with the following:

1-(4-methyl-3-nitrophenyl)pyrido[2,3-d]pyrimidine-2,4(1H,3H)-dione,
1-(3-cyanophenyl)pyrido[2,3-d]pyrimidine-2,4(1H,3H)-dione,
1-phenyl-pyrido[2,3-d]pyrimidine-2,4(1H,3H)-dione,
1-(3-chlorophenyl)pyrido[2,3-d]pyrimidine-2,4(1H,3H)-dione,
1-(3-methoxycarbonylphenyl)pyrido[2,3-d]pyrimidine-2,4(1H,3H)-dione,
1-(3-methylthiophenyl)pyrido[2,3-d]pyrimidine-2,4(1H,3H)-dione,
1-(3-fluorophenyl)pyrido[2,3-d]pyrimidine-2,4(1H,3H)-dione,
1-(2,4-dimethyl-3-methoxycarbonylphenyl)pyrido[2,3-d]pyrimidine-2,4(1H,3H)-dione,
1-(2,4-dimethyl-3-nitrophenyl)pyrido[2,3-d]pyrimidine-2,4(1H,3H)-dione,
1-(2,4-dimethylphenyl)pyrido[2,3-d]pyrimidine-2,4(1H,3H)-dione,
1-(3,4-dichlorophenyl)pyrido[2,3-d]pyrimidine-2,4(1H,3H)-dione,
1-(3-methylcarbonylphenyl)pyrido[2,3-d]pyrimidine-2,4(1H,3H)-dione,
1-(3,5-dibromophenyl)pyrido[2,3-d]pyrimidine-2,4(1H,3H)-dione,
1-(2,4,6-trifluoro-3-ethylphenyl)pyrido[2,3-d]pyrimidine-2,4(1H,3H)-dione,
1-(2,4-dimethyl-3-methylcarbonylphenyl)pyrido[2,3-d]pyrimidine-2,4(1H,3H)-dione,
1-(2,6-difluoro-4-propylphenyl)pyrido[2,3-d]pyrimidine-2,4(1H,3H)-dione,
1-(2,6-difluoro-4-cyanophenyl)pyrido[2,3-d]pyrimidine-2,4(1H,3H)-dione, and
1-(3,5-dimethylthiophenyl)pyrido[2,3-d]pyrimidine-2,4(1H,3H)-dione;

there are obtained the following compounds:
1-4-methyl-3-nitrophenyl)-3-(3-pyridylmethyl)-pyrido[2,3-d]pyrimidine-2,4(1H,3H)-dione, mp 221°–222° C.,
1-(3-cyanophenyl)-3-(4-pyridylmethyl)pyrido[2,3-d]pyrimidine-2,4(1H,3H)-dione, mp 174°–176° C.,
1-phenyl-3-(4-pyridylmethyl)pyrido[2,3-d]pyrimidine-2,4(1H,3H)-dione, mp 202°–203° C.,
1-(3-chlorophenyl)-3-(4-pyridylmethyl)pyrido[2,3-d]pyrimidine-2,4(1H,3H)-dione, mp 196.0°–196.6° C.,
1-(3-methoxycarbonylphenyl)-3-(4-pyridylmethyl)-pyrido[2,3-d]pyrimidine-2,4(1H,3H)-dione, mp 207°–208° C.,
1-(3-methylthiophenyl)-3-(4-pyridylmethyl)pyrido[2,3-d]pyrimidine-2,4(1H,3H)-dione, mp 205°–206° C.,
1-(3-fluorophenyl)-3-(4-pyridylmethyl)pyrido[2,3-d]pyrimidine-2,4(1H,3H)-dione, mp 184.5°–185° C.,
1-(2,4-dimethyl-3-methoxycarbonylphenyl)-3-(4-pyridylmethyl)pyrido[2,3-d]pyrimidine-2,4(1H,3H)-dione,
1-(2,4-dimethyl-3-nitrophenyl)-3-(4-pyridylmethyl)-pyrido[2,3-d]pyrimidine-2,4(1H,3H)-dione,
1-(2,4-dimethylphenyl)-3-(4-pyridylmethyl)pyrido[2,3-d]pyrimidine-2,4(1H,3H)-dione,
1-(3,4-dichlorophenyl)-3-(4-pyridylmethyl)pyrido[2,3-d]pyrimidine-2,4(1H,3H)-dione,
1-(3-methylcarbonylphenyl)-3-(4-pyridylmethyl)-pyrido[2,3-d]pyrimidine-2,4(1H,3H)-dione,
1-(3,5-dibromophenyl)-3-(4-pyridylmethyl)pyrido[2,3-d]pyrimidine-2,4(1H,3H)-dione,
1-(2,4,6-trifluoro-3-ethylphenyl)-3-(4-pyridylmethyl)pyrido[2,3-d]pyrimidine-2,4(1H,3H)-dione,
1-(2,4-dimethyl-3-methylcarbonylphenyl)-3-(4-pyridylmethyl)pyrido[2,3-d]pyrimidine-2,4(1H,3H)-dione,
1-(2,6-difluoro-4-propylphenyl)-3-(4-pyridylmethyl)-pyrido[2,3-d]pyrimidine-2,4(1H,3H)-dione,
1-(2,6-difluoro-4-cyanophenyl)-3-(4-pyridylmethyl)-pyrido[2,3-d]pyrimidine-2,4(1H,3H)-dione, and
1-(3,5-dimethylthiophenyl)-3-(4-pyridylmethyl)-pyrido[2,3-d]pyrimidine-2,4(1H,3H)-dione.

5C. Other Compounds of Formula I, Varying $R^1$

By following the procedures of Example 5A and substituting 4-chloromethylpyridine hydrochloride with the following:
2-(chloromethyl)pyridine,
3-(chloromethyl)pyridine,
2-(chloromethyl)quinoline,
4-(2-chloroethyl)pyridine,
3-(2-chloroethyl)pyridine,
2-(2-chloroethyl)quinoline,
4-chloromethyl-(2,6-dimethyl)pyridine,
4-(2-chloroethyl)-(2,6-dimethyl)pyridine,
4-chloromethyl-2-pyridone,
4-(2-chloroethyl)-2-pyridone,
4-chloromethyl-1-methyl-2-pyridone,
5-bromomethyl-2-pyridone,
5-(2-chloroethyl)-2-pyridone,
5-(2-chloromethyl)-2-pyridone,
5-(2-chloroethyl)-1-methyl-2-pyridone,
5-bromomethyl-1-methyl-2-pyridone,
4-bromomethyl-2-pyranone,
4-(2-chloroethyl)-2-pyranone, and
4-(chloromethyl)-2-pyranone;

there are obtained the following compounds:
1-(3-nitrophenyl)-3-(2-pyridylmethyl)pyrido[2,3-d]pyrimidine-2,4(1H,3H)-dione, mp 194°–195° C.,
1-(3-nitrophenyl)-3-(3-pyridylmethyl)pyrido[2,3-d]pyrimidine-2,4(1H,3H)-dione, mp 232°–234° C.,
1-(3-nitrophenyl)-3-[2-(1-quinolinyl)methyl]pyrido[2,3-d]pyrimidine-2,4(1H,3H)-dione, mp 209°–210° C.,
1-(3-nitrophenyl)-3-(4-pyridyl-2-ethyl)pyrido[2,3-d]pyrimidine-2,4(1H,3H)-dione,
1-(3-nitrophenyl)-3-(3-pyridyl-2-ethyl)pyrido[2,3-d]pyrimidine-2,4(1H,3H)-dione,
1-(3-nitrophenyl)-3-(2-quinolinyl-2-ethyl)pyrido[2,3-d]pyrimidine-2,4(1H,3H)-dione,
1-(3-nitrophenyl)-3-[4-(2,6-dimethyl)pyridylmethyl]-pyrido[2,3-d]pyrimidine-2,4(1H,3H)-dione,
1-(3-nitrophenyl)-3-[4-(2,6-dimethyl)pyridyl-2-ethyl]-pyrido[2,3-d]pyrimidine-2,4(1H,3H)-dione,
1-(3-nitrophenyl)-3-(4-pyridonylmethyl)pyrido[2,3-d]pyrimidine-2,4(1H,3H)-dione,
1-(3-nitrophenyl)-3-[4-(2-pyridonyl)-2-ethyl]pyrido[2,3-d]pyrimidine-2,4(1H,3H)-dione,
1-(3-nitrophenyl)-3-[4-(2-pyridonyl-1-methyl)methyl]-pyrido[2,3-d]pyrimidine-2,4(1H,3H)-dione,
1-(3-nitrophenyl)-3-[5-(2-pyridonyl)methyl]pyrido[2,3-d]pyrimidine-2,4(1H,3H)-dione,
1-(3-nitrophenyl)-3-[5-(2-pyridonyl)-2-ethyl]pyrido[2,3-d]pyrimidine-2,4(1H,3H)-dione,
1-(3-nitrophenyl)-3-[5-(2-pyridonyl)methyl]pyrido[2,3-d]pyrimidine-2,4(1H,3H)-dione,
1-(3-nitrophenyl)-3-[5-(2-pyridonyl-1-methyl)-2-ethyl]-pyrido[2,3-d]pyrimidine-2,4(1H,3H)-dione,
1-(3-nitrophenyl)-3-[5-(2-pyridonyl-1-methyl)methyl]-pyrido[2,3-d]pyrimidine-2,4(1H,3H)-dione,
1-(3-nitrophenyl)-3-[4-(2-pyranonyl)methyl]pyrido[2,3-d]pyrimidine-2,4(1H,3H)-dione,
1-(3-nitrophenyl)-3-[4-(2-pyranonyl)-2-ethyl]-pyrido[2,3-d]pyrimidine-2,4(1H,3H)-dione, and 1-(3-nitrophenyl)-3-[4-(2-pyranonyl)methyl]pyrido[2,3-d]pyrimidine-2,4(1H,3H)-dione.

5D. Other Compounds of Formula I, Varying $R^1$ and $R^2$-$R^6$

By following the procedures of Example 5A and substituting 4-chloromethylpyridine hydrochloride and 1-(3-nitrophenyl)pyrido[2,3-d]pyrimidine-2,4(1H,3H)-dione with the following:

1-(4-methyl-3-nitrophenyl)pyrido[2,3-d]pyrimidine-2,4(1H,3H)-dione, and 3-chloromethylpyridine, 1-(3-chlorophenyl)pyrido[2,3-d]pyrimidine-2,4(1H,3H)-dione and 3-(chloromethyl)pyridine, 1-(3-methoxycarbonylphenyl)pyrido[2,3-d]pyrimidine-2,4(1H,3H)-dione and 3-(chloromethyl)pyridine;

1-(3,5-diethyl-4-carbamoylphenyl)pyrido[2,3-d]pyrimidine-2,4(1H,3H)-dione and 2-chloromethylpyridine, 1-(3-chloro-6-fluorophenyl)pyrido[2,3-d]pyrimidine-2,4(1H,3H)-dione and 2-(2-bromoethyl)quinoline, 1-(2-methyl-4-methylcarbonylphenyl)pyrido[2,3-d]pyrimidine-2,4(1H,3H)-dione and 4-methylchloro-2-pyridone, 1-(3-cyano-4-methoxycarbonylphenyl)pyrido[2,3-d]pyrimidine-2,4(1H,3H)-dione and 4-(2-chloroethyl)-2-pyridone, and 1-(3-methoxycarbonyl-4-fluorophenyl)pyrido[2,3-d]pyrimidine-2,4(1H,3H)-dione and 4-(2-chloroethyl)-2-pyranone;

there are obtained the following compounds:

1-(4-methyl-3-nitrophenyl)-3-(3-pyridylmethyl)-pyrido[2,3-d]pyrimidine-2,4(1H,3H)-dione, mp 221°-222° C., 1-(3-chlorophenyl)-3-(3-pyridylmethyl)pyrido[2,3-d]pyrimidine-2,4(1H,3H)-dione, mp 181°-183° C., 1-(3-methoxycarbonylphenyl)-3-(3-pyridylmethyl)-pyrido[2,3-d]pyrimidine-2,4(1H,3H)-dione, mp 188° C., 1-(3,5-diethyl-4-carbamoylphenyl)-3-(2-pyridylmethyl)-pyrido[2,3-d]pyrimidine-2,4(1H,3H)-dione, 1-(3-chloro-6-fluorophenyl)-3-(2-quinolinyl-2-ethyl)-pyrido[2,3-d]pyrimidine-2,4(1H,3H)-dione, 1-(2-methyl-4-methylcarbonylphenyl)-3-(4-pyridonyl-methyl)pyrido[2,3-d]pyrimidine-2,4(1H,3H)-dione, 1-(3-cyano-4-methoxycarbonylphenyl)-3-[4-(2-pyridonyl)-2-ethyl]pyrido[2,3-d]pyrimidine-2,4(1H,3H)-dione, and 1-(3-methoxycarbonyl-4-fluorophenyl)-3-[4-(2-pyranonyl)-2-ethyl]pyrido[2,3-d]pyrimidine-2,4(1H,3H)-dione.

EXAMPLE 6

Preparation of 2-(3-Chloroanilino)-3-aminomethylpyridine

6A. Formula 8, Where $R^3$ is Chloro

A suspension of lithium aluminum hydride (4.6 g, 121.2 mmoles) in tetrahydrofuran (300 ml) was heated to reflux. To this refluxing suspension, a solution of 2-(3-chloroanilino)-3-carbamoylpyridine (10.0 g, 40.4 mmole) in tetrahydrofuran (200 ml), (prepared, for example, as described in Example 3B), was slowly added dropwise. The reaction mixture was stirred for 18 hours and cooled to room temperature. Solutions of tetrahydrofuran and H2O (20 ml, 50:50), 20 ml of 10% NaOH and 20 ml of H2O were added to the reaction mixture. A white precipitate was formed and removed by filtration. Three quarters of the solvent was removed. The residue was extracted in ethyl acetate (5×100 ml) and washed with H2O. The solution was dried over MgSO4 and the MgSO4 was removed by filtration. The solvent was removed by evaporation resulting in a 10.3 g of 2-(3-chloroanilino)-3-aminomethylpyridine, as a light yellow oil, which was used without further purification.

6B. Preparation of Other Compounds of Formula 8

By following the procedures of Example 6A and substituting for 2-(3-chloroanilino)-3-carbamoylpyridine with the following:

2-(3-methylthioanilino)-3-carbamoylpyridine,
2-(2,4-dimethylanilino)-3-carbamoylpyridine,
2-(3,4-dichloroanilino)-3-carbamoylpyridine, and
2-(3-fluoroanilino)-3-carbamoylpyridine;
there are obtained the following compounds:
2-(3-methylthioanilino)-3-aminomethylpyridine,
2-(2,4-dimethylanilino)-3-aminomethylpyridine,
2-(3,4-dichloroanilino)-3-aminomethylpyridine, and
2-(3-fluoroanilino)-3-aminomethylpyridine.

EXAMPLE 7

Preparation of 1-(3-Chlorophenyl)pyrido[2,3-d]pyrimidine-2(1H,3H)-one

7A. Formula 9, Where Y is —CH2— and $R^3$ is Chloro

Sodium hydride (previously washed in hexanes) was added to a solution of 2-(3-chloroanilino)-3-aminomethylpyridine (10.3 g, 44.1 mmole) in tetrahydrofuran (200 ml). The solution was stirred at room temperature for 5 minutes. 1,1'-Carbonyldiimidazole (10.7 g, 66.1 mmole) was added gradually to the solution with stirring; after the addition the solution was refluxed for 22 hours. The solvents were removed and H2O was added to the residue. The solid material was extracted in ethyl acetate, washed with H2O and dried over MgSO4. The MgSO4 was removed by filtration and the solvents by evaporation. The product was recrystallized out of ethyl acetate/ethyl ether yielding 5.7 g (21.9 mmole, 50% yield) of 1-(3-chlorophenyl)pyrido[2,3-d]pyrimidine-2(1H,3H)-one (mp 188°-187° C.), as a tan solid.

7B. Preparation of Other Compounds of Formula 9

By following the procedures of Example 7A and substituting 2-(3-chloroanilino)-3-aminomethylpyridine with the following:

2-(3-methylthioanilino)-3-aminomethylpyridine,
2-(2,4-dimethylanilino)-3-aminomethylpyridine,
2-(3,4-dichloroanilino)-3-aminomethylpyridine, and
2-(3-fluoroanilino)-3-aminomethylpyridine;
there are obtained the following compounds:
1-(3-methylthiophenyl)pyrido[2,3-d]pyrimidine-2(1H,3H)-one,
1-(2,4-dimethylphenyl)pyrido[2,3-d]pyrimidine-2(1H,3H)-one,
1-(3,4-dichlorophenyl)pyrido[2,3-d]pyrimidine-2(1H,3H)-one, and
1-(3-fluorophenyl)pyrido[2,3-d]pyrimidine-2(1H,3H)-one.

EXAMPLE 8

Preparation of 1-(3-Chlorophenyl)-3-(4-pyridylmethyl)pyrido[2,3-d]-pyrimidine-2(1H,3H)-one 8A. Formula I, Where Y is —CH2—, $R^1$ is 4-pyridylmethyl and $R^3$ is Chloro Sodium hydride (50% dispersion in oil) (364 mg, 7.6 mmole), previously washed in hexanes, was added to a solution of 1-(3-chlorophenyl)pyrido[2,3-d]pyrimidine-2(1H,3H)-one (500 mg, 1.9 mmole) in tetrahydrofuran (100 ml). The suspension was stirred for 5 minutes at room temperature and 4-chloromethylpyridine hydrochloride was added. The suspension was refluxed for 18 hours. The solvents were removed and H₂O was added to the residue. The residue was extracted twice with ethyl acetate (2×25 ml). The organic phases were combined and the solvents removed. The residue was purified with preparative thin-layer chromatography (ethyl acetate as the eluent) yielding 116 mg (0.33 mmole, 17% yield) of 1-(3-chlorophenyl)-3-(4-pyridylmethyl)-pyrido[2,3-d]pyrimidine-2(1H,3H)-one (mp 132°-134° C.), as a white solid.

8B. Formula I Where Y is —CH₂—, Varying $R^2$-$R^6$.

By following the procedures of Example 8A and substituting 1-(3-chlorophenyl)pyrido[2,3-d]pyrimidine-2(1H, 3H)-one with the following:
1-(3-methylthiophenyl)pyrido[2,3-d]pyrimidine-2(1H,3H)-one,
1-(2,4-dimethylphenyl)pyrido[2,3-d]pyrimidine-2(1H,3H)-one,
1-(3,4-dichlorophenyl)pyrido[2,3-d]pyrimidine-2(1H,3H)-one, and
1-(3-fluorophenyl)pyrido[2,3-d]pyrimidine-2(1H,3H)-one;
there are obtained the following compounds:
1-(3-methylthiophenyl)-3-(4-pyridylmethyl)pyrido[2,3-d]pyrimidine-2(1H,3H)-one,
1-(2,4-dimethylphenyl)-3-(4-pyridylmethyl)pyrido[2,3-d]pyrimidine-2(1H,3H)-one,
1-(3,4-dichlorophenyl)-3-(4-pyridylmethyl)pyrido[2,3-d]pyrimidine-2(1H,3H)-one, and
1-(3-fluorophenyl)-3-(4-pyridylmethyl)pyrido[2,3-d]pyrimidine-2(1H,3H)-one.

8C. Formula I, Where Y is —CH₂—, Varying $R^1$

By following the procedures of Example 8A and substituting 4-chloromethypyridine hydrochloride with the following:
3-chloromethylpyridine,
4-(2-chloroethyl)pyridine,
3-(2-chloroethyl)pyridine,
2-chloromethylquinoline,
2-(2-chloroethyl)quinoline,
4-chloromethyl-(2,6-dimethyl)pyridine,
4-(2-chloroethyl)-(2,6-dimethyl)pyridine,
4-chloromethyl-2-pyridone,
4-(2-chloroethyl)-2-pyridone,
4-chloromethyl-1-methyl-2-pyridone,
5-bromomethyl-2-pyridone,
5-(2-chloroethyl)-2-pyridone,
5-(2-chloroethyl)-2-pyridone,
5-(2-chloroethyl)-1-methyl-2-pyridone,
5-bromomethyl-1-methyl-2-pyridone,
4-bromomethyl-2-pyranone, and
4-(2-chloroethyl)-2-pyranone;
there are obtained the following compounds:
1-(3-chlorophenyl)-3-(3-pyridylmethyl)pyrido[2,3-d]pyrimidine-2(1H,3H)-one, mp 179°-180° C.,
1-(3-chlorophenyl)-3-(4-pyridyl-2-ethyl)pyrido[2,3-d]pyrimidine-2(1H,3H)-one,
1-(3-chlorophenyl)-3-(3-pyridyl-2-ethyl)pyrido[2,3-d]pyrimidine-2(1H,3H)-one,
1-(3-chlorophenyl)-3-(2-quinolinylmethyl)pyrido[2,3-d]pyrimidine-2(1H,3H)-one,
1-(3-chlorophenyl)-3-(2-quinolinyl-2-ethyl)pyrido[2,3-d]pyrimidine-2(1H,3H)-one,
1-(3-chlorophenyl)-3-[4-(2,6-dimethyl)pyridylmethyl]-pyrido[2,3-d]pyrimidine-2(1H,3H)-one,
1-(3-chlorophenyl)-3-[4-(2,6-dimethyl)pyridyl-2-ethyl]-pyrido[2,3-d]pyrimidine-2(1H,3H)-one,
1-(3-chlorophenyl)-3-(4-pyridonylmethyl)pyrido[2,3-d]pyrimidine-2(1H,3H)-one,
1-(3-chlorophenyl)-3-[4-(2-pyridonyl)-2-ethyl]-pyrido[2,3-d]pyrimidine-2(1H,3H)-one,
1-(3-chlorophenyl)-3-[4-(2-pyridonyl-1-methyl)methyl]pyrido[2,3-d]pyrimidine-2(1H,3H)-one,
1-(3-chlorophenyl)-3-[5-(2-pyridonyl)methyl]-pyrido[2,3-d]pyrimidine-2(1H,3H)-one,
1-(3-chlorophenyl)-3-[5-(2-pyridonyl)-2-ethyl]-pyrido[2,3-d]pyrimidine-2(1H,3H)-one,
1-(3-chlorophenyl)-3-[5-(2-pyridonyl)-methyl]-pyrido[2,3-d]pyrimidine-2(1H,3H)-one,
1-(3-chlorophenyl)-3-[5-(2-pyridonyl-1-methyl)-2-ethyl]pyrido[2,3-d]pyrimidine-2(1H,3H)-one,
1-(3-chlorophenyl)-3-[5-(2-pyridonyl-1-methyl)methyl]pyrido[2,3-d]pyrimidine-2(1H,3H)-one,
1-(3-chlorophenyl)-3-[4-(2-pyranonyl)methyl]-pyrido[2,3-d]pyrimidine-2(1H,3H)-one, and
1-(3-chlorophenyl)-3-[4-(2-pyranonyl)-2-ethyl]-pyrido[2,3-d]pyrimidine-2(1H,3H)-one.

EXAMPLE 9

Preparation of 2-(3-Nitroanilino)-3-aminomethylpyridine

9. Formula 8, Where $R^3$ is Nitro 2-(3-Nitroanilino)-3-carbamoylpyridine (1.8 g, 6.9 mmole) (prepared, for example as described in Example 3A) was dissolved in dry tetrahydrofuran (20 ml) and added dropwise to a cooled (0° C.) 1M solution of borane in tetrahydrofuran (16.0 ml, 16.0 mmole) over 15 minutes and refluxed for 8 hours. The reaction mixture was allowed to cool to room temperature and 4 ml of 6N HCl was added dropwise. An orange precipitate was formed. The now acidic solution was placed in an ice bath and neutralized with NaOH pellets (10 pellets approximately 2.0 g). This reaction was very exothermic. The slurry was cooled to 0° C. and extracted with ethyl acetate (5×25 ml). The organic phases were combined, dried over MgSO₄, filtered and the solvents removed yielding 1.5 g of 2-(N-nitroanilino)-3-aminomethylpyridine, as an orange oil, which was used without further purification.

EXAMPLE 10

Preparation of 1-(3-Nitrophenyl)pyrido[2,3-d]pyrimidine-2(1H,3H)-one

10A. Formula 9, Where Y is —CH₂— and $R^3$ is nitro

Following the procedures of Example 7, and substituting 2-(3-nitroanilino)-3-aminomethylpyridine [1.5 g (crude), 6.1 mmole] for 2-(3-chloroanilino)-3-aminomethylpyridine, there was obtained 1.0 g (3.7 mmole, 61% yield) of 1-3-nitrophenyl)pyrido[2,3-d]pyrimidine-2(1H,3H)-one (mp 236°-238° C.), as a brown solid.

EXAMPLE 11

Preparation of 1-(3-Nitrophenyl)-3-benzylpyrido[2,3-d]pyrimidine-2(1H,3H)-one

11A. Formula I, Where Y is —CH₂— and $R^3$ is nitro 1-(3-Nitrophenyl)pyrido[2,3-d]pyrimidine-2(1H,3H)-one (300 mg, 1.1 mmole) was suspended in acetone (100 ml). To this suspension was added powdered K₂CO₃ (607 mg, 4.4 mmole) and benzyl bromide (282 mg, 1.65 mmole). The suspension was refluxed for 18 hours. The suspension was filtered, while still hot, to remove solid unreacted K$_2$CO$_3$, which was discarded. The solvents were removed from the filtrate and the residue was purified by preparative thin-layer chromatography (eluted with ethyl acetate) yielding 104 mg (0.289 mmole, 26% yield) of 1-(3-nitrophenyl)-3-benzyl-pyrido[2,3-d]pyrimidine-2(1H,3H)-one (mp 144°-145° C.), as a yellow solid.

11B. Formula I Varying R$^1$

By following the procedures of Example 11A and substituting benzyl bromide with 4-chloromethylpyridine hydrochloride, there was obtained 1-(3-nitrophenyl)-3-(4-pyridylmethyl)pyrido[2,3-d]pyrimidine-2(1H,3H)-one, mp 169°-170° C.

EXAMPLE 12

Preparation of
1-(3-Chlorophenyl)-3-[5-(2-methyl)pyridylmethyl]-pyrido[2,3-d]pyrimidine-2,4(1H,3H)-dione 12A. Formula I, where R$^1$ is 5-(2-methyl)pyridylmethyl Preparation of 5-hydroxymethyl-2-methyl-pyridine 5-Methoxycarbonyl-2-methyl-pyridine (3.0 g, 19.8 mmole) was dissolved in toluene (60 ml) and cooled to −78° C. To this solution, a 39.7 ml of a solution of 1M diisobutylaluminum hydride in toluene was added dropwise. The reaction mixture was stirred for 1 hour at −78° C., allowed to warm to room temperature and stirred for an additional 18 hours. Methanol (8 ml) was then added dropwise at room temperature to the reaction mixture. The mixture was stirred until a thick gel was formed. 1N HCl (10 ml) was added to dissolve the gel. The resulting phases were separated, the organic phase was extracted in ethyl acetate and dried over MgSO$_4$. The solvents were removed yielding crude 5-hydroxymethyl-2-methylpyridine (540 mg) as an oil, which was used without further purification.

1-(3-chlorophenyl)-pyrido[2,3-d]pyrimidine-2,4(1H,3H)-dione (983 mg, 3.59 mmoles), prepared, e.g., as described in Example 4B, was dissolved in tetrahydrofuran (25 ml). 5-Hydroxymethyl-2-methyl-pyridine (540 mg, 3.99 mmole) and triphenylphosphine (1.4 g, 5.39 mmole) was added to this solution under an inert atmosphere with stirring at room temperature. Diisopropyl azodicarboxylate, i.e., DIAD, 1.1 g, 5.39 mmole) in tetrahydrofuran (25 ml) was added dropwise to the solution. The reaction mixture was stirred at room temperature under an inert atmosphere for 3 hours. The solvents were removed and the residue was chromatographed yielding 1.1 g (2.9 mmole, 81% yield) of 1-(3-chlorophenyl)-3-[5-(2-methyl)pyridylmethyl]-pyrido[2,3-d]pyrimidine-2,4(1H,3H)-dione (mp 174°-175.5° C.), as a white solid.

12B. Formula I, Where Y is —C(O)—, Varying R$^2$-R$^6$.

By following the procedures of Example 12A and substituting 1-(3-nitrophenyl)pyrido[2,3-d]pyrimidine-2,4(1H,3H)-dione with the following:

1-(2,4-dimethyl-3-methoxycarbonylphenyl)pyrido[2,3-d]-pyrimidine-2,4(1H,3H)-dione,
1-(2,4-dimethyl-3-nitrophenyl)pyrido[2,3-d]pyrimidine-2,4(1H,3H)-dione,
1-(3-chlorophenyl)pyrido[2,3-d]pyrimidine-2,4(1H,3H)-dione,
1-(3-methoxycarbonylphenyl)pyrido[2,3-d]pyrimidine-2,4(1H,3H)-dione,
1-(3-methylthiophenyl)pyrido[2,3-d]pyrimidine-2,4(1H,3H)-dione,
1-(2,4-dimethylphenyl)pyrido[2,3-d]pyrimidine-2,4(1H,3H)-dione,
1-(3,4-dichlorophenyl)pyrido[2,3-d]pyrimidine-2,4(1H,3H)-dione,
1-(3-fluorophenyl)pyrido[2,3-d]pyrimidine-2,4(1H,3H)-dione, and
1-(3-methylcarbonylphenyl)pyrido[2,3-d]pyrimidine-2,4(1H,1H)-dione, there are obtained the following compounds:

1-(2,4-dimethyl-3-methoxycarbonylphenyl)-3-[5-(2-methyl)pyridylmethyl]methyl)pyrido[2,3-d]-pyrimidine-2,4(1H,3H)-dione,
1-(2,4-dimethyl-3-nitrophenyl)-3-[5-(2-methyl)pyridylmethyl]pyrido[2,3-d]pyrimidine-2,4(1H,3H)-dione,
1-(3-chlorophenyl)-3-[5-(2-methyl)pyridylmethyl]-pyrido-2,3-d]pyrimidine-2,4(1H,3H)-dione,
1-(3-methoxycarbonylphenyl)-3-[5-(2-methyl)pyridylmethyl]pyrido[2,3-d]pyrimidine-2,4(1H,3H)-dione,
1-(3-methylthiophenyl)-3-[5-(2-methyl)pyridylmethyl]-pyrido[2,3-d]pyrimidine-2,4(1H,3H)-dione,
1-(2,4-dimethylphenyl)-3-[5-(2-methyl)pyridylmethyl]-pyrido[2,3-d]pyrimidine-2,4(1H,3H)-dione,
1-(3,4-dichlorophenyl)-3-[5-(2-methyl)pyridylmethyl]-pyrido[2,3-d]pyrimidine-2,4(1H,3H)-dione,
1-(3-fluorophenyl)-3-[5-(2-methyl)pyridylmethyl]-pyrido[2,3-d]pyrimidine-2,4(1H,3H)-dione, and
1-(3-methylcarbonylphenyl)-3-[5-(2-methyl)pyridylmethyl]pyrido[2,3-d]pyrimidine-2,4(1H,3H)-dione.

12C. Formula I, Where Y is —CH$_2$—

By following the procedures of Example 12A and substituting 1-(3-nitrophenyl)pyrido[2,3-d]pyrimidine-2,4(1H,3H)-dione with the following:

1-(2,4-dimethyl-3-methoxycarbonylphenyl)pyrido[2,3-d]-pyrimidine-2(1H,3H)-one,
1-(2,4-dimethyl-3-nitrophenyl)pyrido[2,3-d]pyrimidine-2(1H,3H)-one,
1-(3-chlorophenyl)pyrido[2,3-d]pyrimidine-2(1H,3H)-one,
3-methoxycarbonylphenyl)pyrido[2,3-d]pyrimidine-2(1H,3H)-one,
1-(3-methylthiophenyl)pyrido[2,3-d]pyrimidine-2(1H,3H)one,
2,4-dimethylphenyl)pyrido[2,3-d]pyrimidine-2(1H,3H)one,
1-(3,4-dichlorophenyl)pyrido[2,3-d]pyrimidine-2(1H,3H)one,
1-(3-fluorophenyl)pyrido[2,3-d]pyrimidine-2(1H,3H)-one, and
1-(3-methylcarbonylphenyl)pyrido[2,3-d]pyrimidine-2(1H,3H)-one;

there are obtained the following compounds:

1-(2,4-dimethyl-3-methoxycarbonylphenyl)-3-[5-(2-methyl)pyridylmethyl]pyrido[2,3-d]pyrimidine-2(1H,3H)-one,
1-(2,4-dimethyl-3-nitrophenyl)-3-[5-(2-methyl)pyridylmethylmethyl][2,3-d]pyrimidine-2(1H,3H)-one,
1-(3-chlorophenyl)-3-[5-(2-methyl)pyridylmethyl]-pyrido[2,3-d]pyrimidine-2(1H,3H)-one,
1-(3-methoxycarbonylphenyl)-3-[5-(2-methyl)pyridylmethyl]pyrido[2,3-d]pyrimidine-2(1H,3H)-one,
1-(3-methylthiophenyl)-3-[5-(2-methyl)pyridylmethyl]-pyrido[2,3-d]pyrimidine-2(1H,3H)-one,
1-(2,4-dimethylphenyl)-3-[5-(2-methyl)pyridylmethyl]-pyrido[2,3-d]pyrimidine-2(1H,3H)-one,
1-(3,4-dichlorophenyl)-3-[5-(2-methyl)pyridylmethyl]-pyrido[2,3-d]pyrimidine-2(1H,3H)-one,
1-(3-fluorophenyl)-3-[5-(2-methyl)pyridylmethyl]-pyrido[2,3-d]pyrimidine-2(1H,3H)-one, and 1-(3-methylcarbonylphenyl)-3-[5-(2-methyl)pyridylmethyl][2,3-d]pyrimidine-2(1H,3H)-one.

EXAMPLE 13

Preparation of 1-(3-Carbamoylphenyl)-3-(4=pyridylmethyl)pyrido-2,3-d]pyrimidine-2,4(1H,3H)-dione 13A. Formula I, Where $R^3$ is —C(O)NR$^8$R$^9$ 1-(3-Cyanophenyl)-3-(4-pyridylmethyl)pyrido[2,3-d]-pyrimidine-2,4(3H,3H)-dione, prepared, e.g., as described in Example 5B, (100 mg, 0.3 mmole) was suspended in 0.2 ml of H$_2$O, to which 0.9 ml of concentrated sulfuric acid was added. The suspension was heated to 90° C. and stirred for 3 hours monitoring by TLC (thin-layer chromatography) indicated that the reaction was complete]. Upon completion, the mixture was quenched by slowly adding a 10 % solution of Na$_2$CO$_3$ (until pH was neutral by litmus) yielding a solid. The solid was extracted in ethyl acetate and dried over MgSO$_4$. The solvents were removed and the residue further purified using preparative thin-layer chromatography (eluting with ethyl acetate) yielding 64 mg (0.17 mmole, 57% yield) of 1-(3-carbamoylphenyl)-3-carbamoylphenyl)-3-(4-pyridylmethyl)pyrido[2,3-d]pyrimidine-2,4(1H,3H)-dione (mp 244°-245° C.).

13B. Formula I, Where Y is —C(O)—, varying R$^1$.

By following the procedures of Example 13A and substituting 1-(3-cyanophenyl)-3-(4-pyridylmethyl)-pyrido[2,3-d]pyrimidine-2,4(1H,3H)-dione with the following:

1-(2-cyanophenyl)-3-(4-pyridyl-2-ethyl)pyrido[2,3-d]-pyrimidine-2,4(1H,3H)-dione,
1-(3-cyanophenyl)-3-(3-pyridylmethyl)pyrido[2,3-d]-pyrimidine-2,4(1H,3H)-dione,
1-(4-cyanophenyl)-3-(3-pyridyl-2-ethyl)pyrido[2,3-d]-pyrimidine-2,4(1H,3H)-dione,
1-(3-cyanophenyl)-3-(2-quinolinylmethyl)pyrido[2,3-d]-pyrimidine-2,4(1H,3H)-dione,
1-(4-cyanophenyl)-3-(2-quinolinyl-2-ethyl)pyrido[2,3-d]-pyrimidine-2,4(1H,3H)-dione,
1-(2-cyanophenyl)-3-[4-(2,6-dimethyl)pyridylmethyl]-pyrido[2,3-d]pyrimidine-2,4(1H,3H)-dione,
1-(4-cyanophenyl)-3-[4-(2,6-dimethyl)pyridyl-2-ethyl]-pyrido[2,3-d]pyrimidine-2,4(1H,3H)-dione,
1-(2-cyanophenyl)-3-(4-pyridonylmethyl)pyrido[2,3-d]-pyrimidine-2,4(1H,3H)-dione,
1-(3-cyanophenyl)-3-[4-(2-pyridonyl)-2-ethyl]-pyrido[2,3-d]pyrimidine-2,4(1H,3H)-dione,
1-(4-cyanophenyl)-3-[4-(2-pyridonyl-1-methyl)methyl]-pyrido[2,3-d]pyrimidine-2,4(1H,3H)-dione,
1-(2-cyanophenyl)-3-[5-(2-pyridonyl)methyl]pyrido-[2,3-d]pyrimidine-2,4(1H,3H)-dione,
1-(3-cyanophenyl)-3-[5-(2-pyridonyl)-2-ethyl]pyrido-[2,3-d]pyrimidine-2,4(1H,3H)-dione,
1-(4-cyanophenyl)-3-[5-(2-pyridonyl)-2-ethyl]-pyrido[2,3-d]pyrimidine-2,4(1H,3H)-dione,
1-(3-cyanophenyl)-3-[5-(2-pyridonyl-1-methyl)-2-ethyl]pyrido[2,3-d]pyrimidine-2,4(1H,3H)-dione,
1-(3-cyanophenyl)-3-[5-(2-pyridonyl-1-methyl)methyl]-pyrido-[2,3-d]pyrimidine-2,4(1H,3H)-dione,
1-(2-cyanophenyl)-3-[4-(2-pyranonyl)methyl]pyrido-[2,3-d]pyrimidine-2,4(1H,3H)-dione,
1-(3-cyanophenyl)-3-[4-(2-pyranonyl)-2-ethyl]pyrido-[2,3-d]pyrimidine-2,4(1H,3H)-dione, and
1-(4-cyanophenyl)-3-[4-(2-pyranonyl)methyl]-pyrido[2,3-d]pyrimidine-2,4(1H,3H)-dione;
there are obtained the following compounds:

1-(2-carbamoylphenyl)-3-(4-pyridyl-2-ethyl)pyrido-[2,3-d]pyrimidine-2,4(1H,3H)-dione,
1-(3-carbamoylphenyl)-3-(3-pyridylmethyl)pyrido[2,3-d]-pyrimidine-2,4-(1H,3H)-dione,
1-(4-carbamoylphenyl)-3-(3-pyridyl-2-ethyl)pyrido[2,3-d]pyrimidine-2,4(1H,3H)-dione,
1-(3-carbamoylphenyl)-3-(2-quinolinylmethyl)pyrido-[2,3-d]pyrimidine-2,4(1H,3H)-dione,
1-(4-carbamoylphenyl)-3-(2-quinolinyl-2-ethyl)pyrido-[2,3-d]pyrimidine-2,4(1H,3H)-dione,
1-(2-carbamoylphenyl)-3-[4-(2,6-dimethyl)pyridylmethyl]pyrido-[2,3-d]pyrimidine-2,4(1H,3H)-dione,
1-(4-carbamoylphenyl)-3-[4-(2,6-dimethyl)pyridyl-2-ethyl]pyrido[2,3-d]pyrimidine-2,4(1H,3H)-dione,
1-(2-carbamoylphenyl)-3-(4-pyridonylmethyl)pyrido-[2,3-d]pyrimidine-2,4(1H,3H)-dione,
1-(3-carbamoylphenyl)-3-[4-(2-pyridonyl)-2-ethyl]-pyrido-[2,3-d]pyrimidine-2,4(1H,3H)-dione,
4-carbamoylphenyl)-3-[4-(2-pyridonyl-1-methyl)methyl]pyrido[2,3-d]pyrimidine-2,4(1H,3H)-dione,
1-(2-carbamoylphenyl)-3-[5-(2-pyridonyl)methyl]-pyrido[2,3-d]pyrimidine-2,4(1H,3H)-dione,
1-(3-carbamoylphenyl)-3-[5-(2-pyridonyl)-2-ethyl]-pyrido[2,3-d]pyrimidine-2,4(1H,3H)-dione,
1-(4-carbamoylphenyl)-3-[5-(2-pyridonyl)-2-ethyl]-pyrido[2,3-d]pyrimidine-2,4(1H,3H)-dione,
1-(3-carbamoylphenyl)-3-[5-(2-pyridonyl-1-methyl)-2-ethyl]pyrido[2,3-d]pyrimidine-2,4(1H,3H)-dione,
1-(3-carbamoylphenyl)-3-[5-(2-pyridonyl-1-methyl)methyl]pyrido[2,3-d]pyrimidine-2,4(1H,3H)-dione,
1-(2-carbamoylphenyl)-3-[4-(2-pyranonyl)methyl]-pyrido[2,3-d]pyrimidine-2,4(1H,3H)-dione,
1-(3-carbamoylphenyl)-3-[4-(2-pyranonyl)-2-ethyl]-pyrido[2,3-d]pyrimidine-2,4(1H,3H)-dione, and
1-(4-carbamoylphenyl)-3-[4-(2-pyranonyl)methyl]-pyrido[2,3-d]pyrimidine-2,4(1H,3H)-dione.

13C. Formula I, Where Y is —CH$_2$—, and R$^1$

By following the procedures of Example 13A and substituting 1-(3-cyanophenyl)-3-(4-pyridylmethyl)-pyrido[2,3-d]pyrimidine-2,4(1H,3H)-dione with the following:

1-(2-cyanophenyl)-3-(4-pyridyl-2-ethyl)pyrido[2,3-d]-pyrimidine-2(1H,3H)-one,
1-(3-cyanophenyl)-3-(3-pyridylmethyl)pyrido[2,3-d]-pyrimidine-2(1H,3H)-one,
1-(4-cyanophenyl)-3-(3-pyridyl-2-ethyl)pyrido[2,3-d]-pyrimidine-2(1H,3H)-one,
1-(3-cyanophenyl)-3-(2-quinolinylmethyl)pyrido[2,3-d]-pyrimidine-2(1H,3H)-one,
1-(4-cyanophenyl)-3-(2-quinolinyl-2-ethyl)pyrido[2,3-d]-pyrimidine-2(1H,3H)-one,
1-(2-cyanophenyl)-3-[4-(2,6-dimethyl)pyridylmethyl]-pyrido[2,3-d]pyrimidine-2(1H,3H)-one,
1-(4-cyanophenyl)-3-[4-(2,6-dimethyl)pyridyl-2-ethyl]-pyrido[2,3-d]pyrimidine-2(1H,3H)-one,
1-(2-cyanophenyl)-3-(4-pyridonylmethyl)pyrido[2,3-d]-pyrimidine-2(1H,3H)-one,
1-(3-cyanophenyl)-3-[4-(2-pyridonyl)-2-ethyl]-pyrido[2,3-d]pyrimidine-2(1H,3H)-one,
1-(4-cyanophenyl)-3-[4-(2-pyridonyl-1-methyl)methyl]-pyrido[2,3-d]pyrimidine-2(1H,3H)-one,
1-(2-cyanophenyl)-3-[5-(2-pyridonyl)methyl]-pyrido[2,3-d]pyrimidine-2(1H,3H)-one,
1-(3-cyanophenyl)-3-[5-(2-pyridonyl)-2-ethyl]-pyrido[2,3-d]pyrimidine-2(1H,3H)-one,
1-(4-cyanophenyl)-3-[5-(2-pyridonyl)-2-ethyl]-pyrido[2,3-d]pyrimidine-2(1H,3H)-one, 1-(3-cyanophenyl)-3-[5-(2-pyridonyl-1-methyl)-2-ethyl]pyrido[2,3-d]pyrimidine-2(1H,3H)-one,
1-(3-cyanophenyl)-3-[5-(2-pyridonyl-1-methyl)methyl]-pyrido[2,3-d]pyrimidine-2(1H,3H)-one,
1-(2-cyanophenyl)-3-[4-(2-pyranonyl)methyl]-pyrido[2,3-d]pyrimidine-2(1H,3H)-one,
1-(3-cyanophenyl)-3-[4-(2-pyranonyl)-2-ethyl]-pyrido[2,3-d]pyrimidine-2(1H,3H)-one, and
1-(4-cyanophenyl)-3-[4-(2-pyranonyl)-2-ethyl]-pyrido[2,3-d]pyrimidine-2(1H,3H)-one.
there are obtained the following compounds:
1-(2-carbamoylphenyl)-3-(4-pyridyl-2-ethyl)pyrido[2,3-d]pyrimidine-2(1H,3H)-one,
1-(3-carbamoylphenyl)-3-(3-pyridylmethyl)pyrido[2,3-d]-pyrimidine-2(1H,3H)-one,
1-(4-carbamoylphenyl)-3-(3-pyridyl-2-ethyl)pyrido[2,3-d]pyrimidine-2(1H,3H)-one,
1-(3-carbamoylphenyl)-3-(2-quinolinylmethyl)-pyrido[2,3-d]pyrimidine-2(1H,3H)-one,
1-(4-carbamoylphenyl)-3-(2-quinolinyl-2-ethyl)-pyrido[2,3-d]pyrimidine-2(1H,3H)-one,
1-(2-carbamoylphenyl)-3-[4-(2,6-dimethyl)pyridylmethyl]pyrido[2,3-d]pyrimidine-2(1H,3H)-one,
1-(4-carbamoylphenyl)-3-[4-(2,6-dimethyl)pyridyl-2-ethyl-]pyrido[2,3-d]pyrimidine-2(1H,3H)-one,
1-(2-carbamoylphenyl)-3-(4-pyridonylmethyl)-pyrido[2,3-d]pyrimidine-2(1H,3H)-one,
1-(3-carbamoylphenyl)-3-[4-(2-pyridonyl)-2-ethyl]-pyrido[2,3-d]pyrimidine-2(1H,3H)-one,
1-(4-carbamoylphenyl)-3-[4-(2-pyridonyl-1-methyl)methyl]pyrido[2,3-d]pyrimidine-2(1H,3H)-one,
1-(2-carbamoylphenyl)-3-[5-(2-pyridonyl)methyl]-pyrido[2,3-d]pyrimidine-2(1H,3H)-one,
1-(3-carbamoylphenyl)-3-[5-(2-pyridonyl)-2-ethyl]-pyrido[2,3-d]pyrimidine-2(1H,3H)-one,
1-(4-carbamoylphenyl)-3-[5-(2-pyridonyl)-2-ethyl]-pyrido[2,3-d]pyrimidine-2(1H,3H)-one,
1-(3-carbamoylphenyl)-3-[5-(2-pyridonyl-1-methyl-2-ethyl[ethyl]pyrido[2,3-d]pyrimidine-2(1H,3H)-one,
1-(3-carbamoylphenyl)-3-[5-(2-pyridonyl-1-methyl)methyl]pyrido[2,3-d]pyrimidine-2(1H,3H)-one,
1-(2-carbamoylphenyl)-3-[4-(2-pyranonyl)methyl]-pyrido[2,3-d]pyrimidine-2(1H,3H)-one,
1-(3-carbamoylphenyl)-3-[4-(2-pyranonyl)-2-ethyl]-pyrido[2,3-d]pyrimidine-2(1H,3H)-one, and
1-(4-carbamoylphenyl)-3-[4-(2-pyranonyl)-2-ethyl]-pyrido-2,3-d]pyrimidine-2(1H,3H)-one.

EXAMPLE 14

Preparation of 1-(3-Carbamoylphenyl)-3-(3-pyridylmethyl)pyrido[2,3-d]pyrimidine-2,4(1H,3H)-dione 4A. Preparation of Methylaluminum amide reagent Solid ammonium chloride (81.8 g, 1.53 mmole) was finely ground and dried over $P_2O_5$. The ammonium chloride was dissolved in dry toluene (3 ml) and stirred for 30 minutes under an inert atmosphere at room temperature. The solution, while still being stirred, was cooled to 5° C. and a 2 M solution of trimethyl aluminum in toluene (0.77 ml, 1.53 mmole) was slowly added to the solution resulting in the formation of the reagent, methylaluminum amide.

14B. Formula I, Where $R^3$ is —C(O)NR$^8$R$^9$ 1-(3-Methoxycarbonylphenyl)-3-(3-pyridylmethyl)-pyrido[2,3-d]pyrimidine-2,4(1H,3H)-dione (200 mg, 0.51 mmole) was suspended in toluene (5 ml). The suspension was added to the methylaluminum reagent (as prepared in Example 14A). The suspension was stirred for 5 hours at 80° C. The reaction mixture was allowed to cool, quenched with 5% HCl and neutralized with saturated NaHCO$_3$. The reaction mixture was evaporated, the resulting residue was dissolved in ethanol and the solid salt was removed by filtration. The solvent was removed yielding appoximately 200 mg of the crude product. The product was purified by preparative thin-layer chromatography (eluted with CH$_2$Cl$_1$:CH$_3$OH 9:1) yielding 80 mg (0.21 mmole, 42% yield) of 1-(3-carbamoylphenyl)-3(3-pyridylmethyl)-pyrido[2,3-d]pyrimidine-2,4(1H,3H)-dione (mp 219°-220° C.).

14C. Formula I, Where Y is —C(O)—

By following the procedures of Example 14A and substituting 1-(3-methoxycarbonylphenyl)-3-(3-pyridylmethyl)pyrido[2,3-d]pyrimidine-2,4(1H,3H)-dione with the following:
1-(2-methoxycarbonylphenyl)-3-(4-pyridyl-2-ethyl)-pyrido[2,3-d]pyrimidine-2,4(1H,3H)-dione,
1-(3-methoxycarbonylphenyl)-3-(3-pyridylmethyl)-pyrido[2,3-d]pyrimidine-2,4(1H,3H)-dione,
1-(4-methoxycarbonylphenyl)-3-(3-pyridyl-2-ethyl)-pyrido[2,3-d]pyrimidine-2,4 (1H,3H)-dione,
1-(3-methoxycarbonylphenyl)-3-(2-quinolinylmethyl)-pyrido[2,3-d]pyrimidine-2,4(1H,3H)-dione,
1-(4-methoxycarbonylphenyl)-3-(2-quinolinyl-2-ethyl)-pyrido[2,3-d]pyrimidine-2,4(1H,3H)-dione,
1-(2-methoxycarbonylphenyl)-3-[4-(2,6-dimethyl)-pyridylmethyl]pyrido[2,3-d]pyrimidine-2,4(1H,3H)-dione,
1-(4-methoxycarbonylphenyl)-3-[4-(2,6-dimethyl)pyridyl-2-ethyl]pyrido[2,3-d]pyrimidine-2,4(1H,3H)-dione,
1-(2-methoxycarbonylphenyl)-3-(4-pyridonylmethyl)-pyrido[2,3-d]pyrimidine-2,4(1H,3H)-dione,
1-(3-methoxycarbonylphenyl)-3-[4-(2-pyridonyl)-2-ethyl]pyrido[2,3-d]pyrimidine-2,4(1H,3H)-dione,
1-(4-methoxycarbonylphenyl)-3-[4-(2-pyridonyl-1-methyl)methyl]-methyl]pyrido[2,3-d]pyrimidine-2,4(1H,3H)-dione,
1-(2-methoxycarbonylphenyl)-3-[5-(2-pyridonyl)methyl]pyrido[2,3-d]pyrimidine-2,4(1H,3H)-dione,
1-(3-methoxycarbonylphenyl)-3-[5-(2-pyridonyl)-2-ethyl]pyrido[2,3-d]pyrimidine-2,4(1H,3H)-dione,
1-(4-methoxycarbonylphenyl)-3-[5-(2-pyridonyl)-2-ethyl]pyrido[2,3-d]pyrimidine-2,4(1H,3H)-dione,
1-(3-methoxycarbonylphenyl)-3-[5-(2-pyridonyl-4-methyl)-2-ethyl]pyrido[2,3-d]pyrimidine-2,4(1H,3H)-dione, and
1-(3-methoxycarbonylphenyl)-3-[5-(2-pyridonyl-3-methyl)methyl]pyrido[2,3-d]pyrimidine-2,4(1H,3H)dione;
there are obtained the following compounds:
1-(2-carbamoylphenyl)-3-(4-pyridyl-2-ethyl)pyrido[2,3-d]pyrimidine-2,4(1H,3H)-dione,
1-(3-carbamoylphenyl)-3-(3-pyridylmethyl)pyrido[2,3-d]-pyrimidine-2,4(1H,3H)-dione,
1-(4-carbamoylphenyl)-3-(3-pyridyl-2-ethyl)pyrido[2,3-d]pyrimidine-2,4(1H,3H)-dione,
1-(3-carbamoylphenyl)-3-(2-quinolinylmethyl)-pyrido[2,3-d]pyrimidine-2,4(1H,3H)-dione,
1-(4-carbamoylphenyl)-3-(2-quinolinyl-2-ethyl)-pyrido[2,3-d]pyrimidine-2,4(1H,3H)-dione,
1-(2-carbamoylphenyl)-3-[4-(2,6-dimethyl)pyridylmethyl]pyrido[2,3-d]pyrimidine-2,4(1H,3H)-dione,
1-(4-carbamoylphenyl)-3-[4-(2,6-dimethyl)pyridyl-2-ethyl]pyrido[2,3-d]pyrimidine-2,4(1H,3H)-dione, 1-(2-carbamoylphenyl)-3-(4-pyridonylmethyl)-pyrido[2,3-d]pyrimidine-2,4(1H,3H)-dione,
1-(3-carbamoylphenyl)-3-[4-(2-pyridonyl)-2-ethyl]-pyrido[2,3-d]pyrimidine-2,4(1H,3H)-dione,
1(4-carbamoylphenyl)-3-[4-(2-pyridonyl-1-methyl)methyl]pyrido[2,3-d]pyrimidine-2,4(1H,3H)-dione,
1-(2-carbamoylphenyl)-3-[5-(2-pyridonyl)methyl]-pyrido[2,3-d]pyrimidine-2,4(1H,3H)-dione,
1-(3-carbamoylphenyl)-3-[5-(2-pyridonyl)-2-ethyl]-pyrido[2,3-d]pyrimidine-2,4(1H,3H)-dione,
1-(4-carbamoylphenyl)-3-[5-(2-pyridonyl)-2-ethyl]-pyrido2,3-d]pyrimidine-2,4(1H,3H)-dione,
1-(3-carbamoylphenyl)-3-[5-(2-pyridonyl-4-methyl)-2-ethyl]pyrido[2,3-d]pyrimidine-2,4(1H,3H)-dione, and
1-(3-carbamoylphenyl)-3-[5-(2-pyridonyl-3-methyl)-methyl]pyrido[2,3-d]pyrimidine-2,4(1H,3H)-dione.

14D. Formula I, Where Y is —CH$_2$—

By following the procedures of Example 14A and substituting 1-(3-methoxycarbonylphenyl)-3-(3-pyridylmethyl)pyrido[2,3-d]pyrimidine-2,4(1H,3H)-dione with the following:

1-(2-methoxycarbonylphenyl)-3-(phenyl-2-ethyl)-pyrido2,3-d]pyrimidine-2(1H,3H)-one,
20 1-(2-methoxycarbonylphenyl)-3-(benzyl)pyrido[2,3-d]-pyrimidine-2(1H,3H)-one,
1-(2-methoxycarbonylphenyl)-3-(4-pyridyl-2-ethyl)-pyrido[2,3-d]pyrimidine-2(1H,3H)-one,
1-(3-methoxycarbonylphenyl)-3-(3-pyridylmethyl)-pyrido[2,3-d]pyrimidine-2(1H,3H)-one,
1-(4-methoxycarbonylphenyl)-3-(3-pyridyl-2-ethyl)-pyrido[2,3-d]pyrimidine-2(1H,3H)-one,
1-(3-methoxycarbonylphenyl)-3-(2-quinolinylmethyl)-pyrido[2,3-d]pyrimidine-2(1H,3H)-one,
1-(4-methoxycarbonylphenyl)-3-(2-quinolinyl-2-ethyl)-pyrido[2,3-d]pyrimidine-2(1H,3H)-one,
1-(2-methoxycarbonylphenyl)-3-[4-(2,6-dimethyl)-pyridylmethyl]pyrido[2,3-d]pyrimidine-2(1H,3H)-one,
1-(4-methoxycarbonylphenyl)-3-[4-(2,6-dimethyl)pyridyl-2-ethyl]pyrido[2,3-d]pyrimidine-2(1H,3H)-one,
1-(2-methoxycarbonylphenyl)-3-(4-pyridonylmethyl)-pyrido[2,3-d]pyrimidine-2(1H,3H)-one,
1-(3-methoxycarbonylphenyl)-3-[4-(2-pyridonyl)-2-ethyl]pyrido[2,3-d]pyrimidine-2(1H,3H)-one,
1-(4-methoxycarbonylphenyl)-3-[4-(2-pyridonyl-i-methyl)methyl]pyrido[2,3-d]pyrimidine-2(1H,3H)-one,
1-(2-methoxycarbonylphenyl)-3-[5-(2-pyridonyl)methyl]pyrido[2,3-d]pyrimidine-2(1H,3H)-one,
13-methoxycarbonylphenyl)-3-[5-(2-pyridonyl)-2-ethyl]pyrido[2,3-d]pyrimidine-2(1H,3H)-one,
1-(4-methoxycarbonylphenyl)-3-[5-(2-pyridonyl)-2-ethyl]pyrido[2,3-d]pyrimidine-2(1H,3H)-one,
1-(3-methoxycarbonylphenyl)-3-[5-(2-pyridonyl-1-methyl)-2-ethyl]pyrido[2,3-d]pyrimidine-2(1H,3H)-one, and
1-(3-methoxycarbonylphenyl)-3-[5-(2-pyridonyl-1-methyl)methyl]pyrido[2,3-d]pyrimidine-2(1H,3H)-one;

there are obtained the following compounds:
1-(2-carbamoylphenyl)-3-(phenyl-2-ethyl)pyrido[2,3-d]-pyrimidine-2(1H,3H)-one,
1-(2-carbamoylphenyl)-3-(benzyl)pyrido[2,3-d]pyrimidine-2(1H,3H)-one,
1-(2-carbamoylphenyl)-3-(4-pyridyl-2-ethyl)pyrido[2,3-d]pyrimidine-2(1H,3H)-one,
1-(3-carbamoylphenyl)-3-(3-pyridylmethyl)pyrido[2,3-d]-pyrimidine-2(1H,3H)-one,
1-(4-carbamoylphenyl)-3-(3-pyridyl-2-ethyl)pyrido[2,3-d]pyrimidine-2(1H,3H)-one,
1-(3-carbamoylphenyl)-3-(2-quinolinylmethyl)-pyrido[2,3-d]pyrimidine-2(1H,3H)-one,
1-(4-carbamoylphenyl)-3-(2-quinolinyl-2-ethyl)-pyrido[2,3-d]pyrimidine-2(1H,3H)-one,
1-(2-carbamoylphenyl)-3-[4-(2,6-dimethyl)pyridylmethyl]pyrido[2,3-d]pyrimidine-2(1H,3H)-one,
1-(4-carbamoylphenyl)-3-[4-(2,6-dimethyl)pyridyl-2-ethyl]pyrido[2,3-d]pyrimidine-2(1H,3H)-one,
1-(2-carbamoylphenyl)-3-(4-pyridonylmethyl)-pyrido[2,3-d]pyrimidine-2(1H,3H)-one,
1-(3-carbamoylphenyl)-3-[4-(2-pyridonyl)-2-ethyl]-pyrido[2,3-d]pyrimidine-2(1H,3H)-one,
1-(4-carbamoylphenyl)-3-[4-(2-pyridonyl-1-methyl)methyl]pyrido[2,3-d]pyrimidine-2(1H,3H)-one,
1-(2-carbamoylphenyl)-3-[5-(2-pyridonyl)methyl]-pyrido[2,3-d]pyrimidine-2(1H,3H)-one,
3-carbamoylphenyl)-3-[5-(2-pyridonyl)-2-ethyl]-pyrido[2,3-d]pyrimidine-2(1H,3H)-one,
1-(4-carbamoylphenyl)-3-[5-(2-pyridonyl)-2-ethyl]-pyrido[2,3-d]pyrimidine-2(1H,3H)-one,
1-(3-carbamoylphenyl)-3-[5-(2-pyridonyl-1-methyl)-2-ethyl]pyrido[2,3-d]pyrimidine-2(1H,3H)-one, and
1-(3-carbamoylphenyl)-3-[5-(2-pyridonyl-1-methyl)methyl]pyrido[2,3-d]pyrimidine-2(1H,3H)-one.

EXAMPLE 15

Preparation of
1-(3-N-Methylcarbamoylphenyl)-3-(3-pyridylmethyl)-pyrido[2,3-d]pyrimidine-2,4(1H,3H)-dione 15A.
Preparation of Methyl-N ™ methylaluminum Amide Reagent A 37% solution of concentrated hydrochloric acid (12.6 g) was added dropwise to a solution of 40% aqueous monomethylamine (7.3 ml) and cooled to 0° C. with vigorous stirring. The aqueous solution was evaporated yielding methylamine hydrochloride as white solid crystals, which were dried over $P_2O_5$. The dried crystals were finely ground and stirred in toluene (3 ml) for 30 minutes under an inert atmosphere at room temperature. The solution was cooled to 5° C. and a 2M solution of trimethylaluminum in toluene (0.51 ml) was added slowly into the stirring solution resulting in the reagent, methyl-N-methylaluminum. The solution was allowed to warm to room temperature.

15B. Formula I, Where $R^3$ is —C(O)NR$^8$R$^9$, Where $R^8$ is hydrogen and $R^9$ is methyl A suspension of 1-(3-methoxycarbonylphenyl)-3-(3-pyridylmethyl)pyrido[2,3-d]pyrimidine-2,4(1H,3H)-dione was prepared by suspending the material (200 mg, 0.51 mmole) in toluene (5 ml) with stirring. The suspension was then added dropwise to the methyl-N-methylaluminum amide reagent (as prepared in Example 15A). The reaction mixture was stirred for 5 hours at 80° C. and allowed to cool. It was then quenched with 5% HCl solution and $H_2O$ and neutralized with saturated $NaHCO_3$ (pH at 7). The solvents were evaporated and the residue was dissolved in acetone/ethanol. Solid salts were removed from the solution by filtration, and the remaining solvent was removed in vacuo yielding yellow crystals. The crystals were purified by preparative thin-layer chromatography yielding 56 mg (0.145 mmole, 28% yield) of 1-(3-N-methylcarbamoylphenyl)-3-(3-pyridylmethyl)pyrido[2,3-d]pyrimidine-2,4(1H,3H)-dione (mp 117° C.).

15C. Formula I, Where Y is —C(O)—, Varying $R^2$—$R^6$ and $R^1$.

By following the procedures of Example 15A and substituting I-(3-methoxycarbonylphenyl)-3-(3-pyridylmethyl)pyrido [2,3-d]pyrimidine-2,4(1H,3H)-dione with the following:

1-(2-methoxycarbonylphenyl)-3-(4-pyridyl-2-ethyl)-pyrido[2,3-d]pyrimidine-2,4(1H,3H)-dione,
1-(3-methoxycarbonylphenyl)-3-(3-pyridylmethyl)-pyrido[2,3-d]pyrimidine-2,4(1H,3H)-dione,
1-(4-methoxycarbonylphenyl)-3-(3-pyridyl-2-ethyl)-pyrido[2,3-d]pyrimidine-2,4(1H,3H)-dione,
1-(3-methoxycarbonylphenyl)-3-(2-quinolinylmethyl)-pyrido[2,3-d]pyrimidine-2,4(1H,3H)-dione,
1-(4-methoxycarbonylphenyl)-3-(2-quinolinyl-2-ethyl)-pyrido[2,3-d]pyrimidine-2,4(1H,3H)-dione,
1-(2-methoxycarbonylphenyl)-3-[4-(2,6-dimethyl)-pyridylmethyl]pyrido[2,3-d]pyrimidine-2,4(1H,3H)-dione, dione,
1-(4-methoxycarbonylphenyl)-3-[4-(2,6-dimethyl)pyridyl-2-ethyl]pyrido[2,3-d]pyrimidine-2,4(1H,3H)-dione,
1- (2-methoxycarbonylphenyl)-3-(4-pyridonylmethyl)-pyrido-2,3-d]pyrimidine-2,4(1H,3H)-dione,
1-(3-methoxycarbonylphenyl)-3-[4-(2-pyridonyl)-2-ethyl]-pyrido[2,3-d]pyrimidine-2,4(1H,3H)-dione,
1-(4-methoxycarbonylphenyl)-3-[4-(2-pyridonyl-1-methyl)methyl]pyrido[2,3-d]pyrimidine-2,4(1H,3H)-dione,
1-(2-methoxycarbonylphenyl)-3-[5-(2-pyridonyl)methyl]pyrido[2,3-d]pyrimidine-2,4(1H,3H)-dione,
1-(3-methoxycarbonylphenyl)-3-[5-(2-pyridonyl)-2-ethyl]pyrido[2,3-d]pyrimidine-2,4(1H,3H)-dione,
1-(4-methoxycarbonylphenyl)-3-[5-(2-pyridonyl)-2-ethyl]pyrido[2,3-d]pyrimidine-2,4(1H,3H)-dione,
1-(3-methoxycarbonylphenyl)-3-[5-(2-pyridonyl-1-methyl)-2-ethyl]pyrido[2,3-d]pyrimidine-2,4(1H,3H)-dione, and
1-(3-methoxycarbonylphenyl)-3-[5-(2-pyridonyl-1-methyl)methyl]pyrido[2,3-d]pyrimidine-2,4(1H,3H)-dione;

there are obtained the following compounds:

1-(2-N-methylcarbamoylphenyl)-3-(4-pyridyl-2-ethyl)-pyrido[2,3-d]pyrimidine-2,4(1H,3H)-dione,
1-(3-N-methylcarbamoylphenyl)-3-(3-pyridylmethyl)-pyrido[2,3-d]pyrimidine-2,4(1H,3H)-dione,
1-(4-N-methylcarbamoylphenyl)-3-(3-pyridyl-2-ethyl)-pyrido[2,3-d]pyrimidine-2,4(1H,3H)-dione,
1-(3-N-methylcarbamoylphenyl)-3-(2-quinolinylmethyl)pyrido[2,3-d]pyrimidine-2,4(1H,3H)-dione,
1-(4-N-methylcarbamoylphenyl)-3-(2-quinolinyl-2-ethyl)pyrido[2,3-d]pyrimidine-2,4(1H,3H)-dione,
1-(2-N-methylcarbamoylphenyl)-3-[4-(2,6-dimethyl)-pyridylmethyl]pyrido[2,3-d]pyrimidine-2,4(1H,3H)-dione,
1-(4-N-methylcarbamoylphenyl)-3-[4-(2,6-dimethyl)-pyridyl-2-ethyl]pyrido[2,3-d]pyrimidine-2,4(1H,3H)-dione,
1-(2-N-methylcarbamoylphenyl)-3-(4-pyridonylmethyl)pyrido[2,3-d]pyrimidine-2,4(1H,3H)-dione,
1-(3-N-methylcarbamoylphenyl)-3-[4-(2-pyridonyl)-2-ethyl]pyrido[2,3-d]pyrimidine-2,4(1H,3H)-dione,
1-(4-N-methylcarbamoylphenyl)-3-[4-(2-pyridonyl-1-methyl)methyl]pyrido[2,3-d]pyrimidine-2,4(1H,3H)-dione,
1-(2-N-methylcarbamoylphenyl)-3-[5-(2-pyridonyl)methyl]pyrido[2,3-d]pyrimidine-2,4(1H,3H)-dione,
1-(3-N-methylcarbamoylphenyl)-3-[5-(2-pyridonyl)-2-ethyl]pyrido[2,3-d]pyrimidine-2,4(1H,3H)-dione,
1-(4-N-methylcarbamoylphenyl)-3-[5-(2-pyridonyl)-2-ethyl]pyrido[2,3-d]pyrimidine-2,4(1H,3H)-dione,
1-(3-N-methylcarbamoylphenyl)-3-[5-(2-pyridonyl-1-methyl)-2-ethyl]pyrido[2,3-d]pyrimidine-2,4(1H,3H)-dione, and
1-(3-N-methylcarbamoylphenyl)-3-[5-(2-pyridonyl-1-methyl)methyl]pyrido[2,3-d]pyrimidine-2,4(1H,3H)dione.

15D. Formula I, Where Y is —$CH_2$—

By following the procedures of Example 15A and substituting 1-(3-methoxycarbonylphenyl)-3-(3-pyridylmethyl)pyrido[2,3-d]pyrimidine-2,4(1H,3H)-dione with the following:

1-(2-methoxycarbonylphenyl)-3-(phenyl-2-ethyl)-pyrido[2,3-d]pyrimidine-2(1H,3H)-one,
1-(2-methoxycarbonylphenyl)-3-(benzyl)pyrido[2,3-d]-pyrimidine-2(1H,3H)-one,
1-(2-methoxycarbonylphenyl)-3-(4-pyridyl-2-ethyl)-pyrido[2,3-d]pyrimidine-2(1H,3H)-one,
1-(3-methoxycarbonylphenyl)-3-(3-pyridylmethyl)-pyrido[2,3-d]pyrimidine-2(1H,3H)-one,
1-(4-methoxycarbonylphenyl)-3-(3-pyridyl-2-ethyl)-pyrido[2,3-d]pyrimidine-2(1H,3H)-one,
1-(3-methoxycarbonylphenyl)-3-(2-quinolinylmethyl)-pyrido[2,3-d]pyrimidine-2(1H,3H)-one,
1-(4-methoxycarbonylphenyl)-3-(2-quinolinyl-2-ethyl)-pyrido[2,3-d]pyrimidine-2(1H,3H)-one,
1-(2-methoxycarbonylphenyl)-3-[4-(2,6-dimethyl)-pyridylmethyl]pyrido[2,3-d]pyrimidine-2(1H,3H)-one,
1-(4-methoxycarbonylphenyl)-3-[4-(2,6-dimethyl)pyridyl-2-ethyl]pyrido[2,3-d]pyrimidine-2(1H,3H)-one,
1-(2-methoxycarbonylphenyl)-3-(4-pyridonylmethyl)-pyrido[2,3-d]pyrimidine-2(1H,3H)-one,
1-(3-methoxycarbonylphenyl)-3-[4-(2-pyridonyl)-2-ethyl]pyrido[2,3-d]pyrimidine-2(1H,3H)-one,
1-(4-methoxycarbonylphenyl)-3-[4-(2-pyridonyl-1-methyl)methyl]pyrido[2,3-d]pyrimidine-2(1H,3H)-one,
1-(2-methoxycarbonylphenyl)-3-[5-(2-pyridonyl)methyl]pyrido[2,3-d]pyrimidine-2(1H,3H)-one,
1-(3-methoxycarbonylphenyl)-3-[5-(2-pyridonyl)-2-ethyl]pyrido[2,3-d]pyrimidine-2(1H,3H)-one,
1-(4-methoxycarbonylphenyl)-3-[5-(2-pyridonyl)-2-ethyl]pyrido[2,3-d]pyrimidine-2(1H,3H)-one,
1-(3-methoxycarbonylphenyl)-3-[5-(2-pyridonyl-1-methyl)-2-ethyl]pyrido[2,3-d]pyrimidine-2(1H,3H)-one, and
1-(3-methoxycarbonylphenyl)-3-[5-(2-pyridonyl-1-methyl)methyl]pyrido[2,3-d]pyrimidine-2(1H,3H)-one;

there are obtained the following compounds:

1-(2-N-methylcarbamoylphenyl)-3-(phenyl-2-ethyl)-pyrido[2,3-d]pyrimidine-2(1H,3H)-one,
1-(2-N-methylcarbamoylphenyl)-3-(benzyl)pyrido[2,3-d]pyrimidine-2(1H,3H)-one,
1-(2-N-methylcarbamoylphenyl)-3-(4-pyridyl-2-ethyl)-pyrido[2,3-d]pyrimidine-2(1H,3H)-one,
1-(3-N-methylcarbamoylphenyl)-3-(3-pyridylmethyl)-pyrido[2,3-d]pyrimidine-2-(1H,3H)-one,
1-(4-N-methylcarbamoylphenyl)-3-(3-pyridyl-2-ethyl)-pyrido[2,3-d]pyrimidine-2(1H,3H)-one,
1-(3-N-methylcarbamoylphenyl)-3-(2-quinolinylmethyl)pyrido[2,3-d]pyrimidine-2(1H,3H)-one,
1-(4-N-methylcarbamoylphenyl)-3-(2-quinolinyl-2-ethyl)pyrido[2,3-d]pyrimidine-2(1H,3H)-one, 1-(2-N-methylcarbamoylphenyl)-3-[4-(2,6-dimethyl)-pyridylmethyl]pyrido[2,3-d]pyrimidine-2(1H,3H)-one, 1-(4-N-methylcarbamoylphenyl)-3-[4-(2,6-dimethyl)-pyridyl-2-ethyl]pyrido[2,3-d]pyrimidine-2(1H,3H)-one, 1-(2-N-methylcarbamoylphenyl)-3-(4-pyridonylmethyl)pyrido[2,3-d]pyrimidine-2(1H,3H)-one, 1-(3-N-methylcarbamoylphenyl)-3-[4-(2-pyridonyl)-2-ethyl]pyrido[2,3-d]pyrimidine-2(1H,3H)-one, 1-(4-N-methylcarbamoylphenyl)-3-[4-(2-pyridonyl-1-methyl)methyl]pyrido[2,3-d]pyrimidine-2(1H,3H)-one, 1-(2-N-methylcarbamoylphenyl)-3-[5-(2-pyridonyl)methyl]pyrido[2,3-d]pyrimidine-2(1H,3H)-one, 1-(3-N-methylcarbamoylphenyl)-3-[5-(2-pyridonyl)-2-ethyl]pyrido[2,3-d]pyrimidine-2(1H,3H)-one, 1-(4-N-methylcarbamoylphenyl)-3-[5-(2-pyridonyl)-2-ethyl]pyrido[2,3-d]pyrimidine-2(1H,3H)-one, 1-(3-N-methylcarbamoylphenyl)-3-[5-(2-pyridonyl-1-methyl)-2-ethyl]pyrido[2,3-d]pyrimidine-2(1H,3H)-one, and 1-(3-N-methylcarbamoylphenyl)-3-[5-(2-pyridonyl-1-methyl)methyl]pyrido[2,3-d]pyrimidine-2(1H,3H)-one.

EXAMPLE 16

Preparation of 1-(3-N,N'-Dimethylcarbamoylphenyl)-3-(3-pyridylmethyl)pyrido[2,3-d]pyrimidine-2,4(1H,3H)-dione 16A. Preparation of Methyl-N,N'-dimethylaluminum Amide Reagent Solid dimethylamine hydrochloride (83.2 mg, 1.02 mmoles) was finely ground and dried over $P_2O_5$ under an inert atmosphere. The ground crystals were stirred into toluene (3 ml) for 30 minutes under an inert atmosphere and cooled to 5° C. A 2M solution of trimethyl aluminum in toluene (0.51 ml, 1.02 mmole) was slowly added to the solution and stirred for 30 minutes at room temperature resulting in the reagent, methyl-N,N'-dimethylaluminum amide.

16B. Formula I, Where $R^3$ is —C(O)NR$^8$R$^9$, Where $R^8$ and $R^9$ are methyl 1-(3-Methoxycarbonylphenyl)-3-(3-pyridylmethyl)-pyrido[2,3-d]pyrimidine-2,4(1H,3H)-dione (200 mg, 0.51 mmole) was suspended in toluene (5 ml) with stirring. The suspension was slowly added to the methyl-N,N'-dimethylaluminum amide reagent (as prepared in Example 16A). The reaction mixture was stirred for 5 hours and heated to 80° C., cooled to 0° C., quenched with 5% HCl and neutralized (pH at 7) with saturated NaHCO$_3$. The solvents were removed from the reaction mixture. The resulting residue was dissolved in ethanol and any residual solid salt removed by filtration. The ethanol was removed yielding 490 mg of crude 1-(3-N,N'-dimethylcarbamoylphenyl)-3-(3-pyridylmethyl)pyrido[2,3-d]pyrimidine-2,4(1H, 3H)-dione, as a light yellow brown powder. The crude product was chromatographed purified by preparative thin-layer chromatography (eluent ethyl acetate) to yield 122 mg (0.304 mmole, 60% yield) pure product (mp 87° C.).

16C. Formula I, Where Y is —C(O)—

By following the procedures of Example 16B and substituting 1-(3-methoxycarbonylphenyl)-3-(3-pyridylmethyl)pyrido[2,3-d]pyrimidine-2,4(1H,3H)-dione with the following:

1-(2-methoxycarbonylphenyl)-3-(4-pyridyl-2-ethyl)-pyrido[2,3-d]pyrimidine-2,4(1H,3H)-dione, 1-(3-methoxycarbonylphenyl)-3-(3-pyridylmethyl)-pyrido[2,3-d]pyrimidine-2,4(1H,3H)-dione, 1-(4-methoxycarbonylphenyl)-3-(3-pyridyl-2-ethyl)-pyrido[2,3-d]pyrimidine-2,4(1H,3H)-dione, 1-(3-methoxycarbonylphenyl)-3-(2-quinolinylmethyl)-pyrido[2,3-d]pyrimidine-2,4(1H,3H)-dione, 1-(4-methoxycarbonylphenyl)-3-(2-quinolinyl-2-ethyl)-pyrido[2,3-d]pyrimidine-2,4(1H,3H)-dione, 1-(2-methoxycarbonylphenyl)-3-[4-(2,6-dimethyl)-pyridylmethyl]pyrido[2,3-d]pyrimidine-2,4(1H,3H)-dione, 1-(4-methoxycarbonylphenyl)-3-[4-(2,6-dimethyl)pyridyl-2-ethyl]pyrido[2,3-d]pyrimidine-2,4(1H,3H)-dione, 1-(2-methoxycarbonylphenyl)-3-(4-pyridonylmethyl)-pyrido[2,3-d]pyrimidine-2,4(1H,3H)-dione, 1-(3-methoxycarbonylphenyl)-3-[4-(2-pyridonyl)-2-ethyl]pyrido[2,3-d]pyrimidine-2,4(1H,3H)-dione, 1-(4-methoxycarbonylphenyl)-3-[4-(2-pyridonyl-1-methyl)methyl]pyrido[2,3-d]pyrimidine-2,4(1H,3H)-dione, 1-(2-methoxycarbonylphenyl)-3-[5-(2-pyridonyl)methyl]pyrido[2,3-d]pyrimidine-2,4(1H,3H)-dione, 1-(3-methoxycarbonylphenyl)-3-[5-(2-pyridonyl)-2-ethyl]pyrido[2,3-d]pyrimidine-2,4(1H,3H)-dione, 1-(4-methoxycarbonylphenyl)-3-[5-(2-pyridonyl)-2-ethyl]pyrido[2,3-d]pyrimidine-2,4(1H,3H)-dione, 1-(3-methoxycarbonylphenyl)-3-[5-(2-pyridonyl-1-methyl)-2-ethyl]pyrido[2,3-d]pyrimidine-2,4(1H,3H)-dione, and 1-(3-methoxycarbonylphenyl)-3-[5-(2-pyridonyl-1-methyl)methyl]pyrido[2,3-d]pyrimidine-2,4(1H,3H)-dione;

there are obtained the following compounds:

1-(2-N,N'-dimethylcarbamoylphenyl)-3-(4-pyridyl-2-ethyl)pyrido[2,3-d]pyrimidine-2,4(1H,3H)-dione, 1-(3-N,N'-dimethylcarbamoylphenyl)-3-(3-pyridylmethyl)pyrido[2,3-d]pyrimidine-2,4(1H,3H)-dione, 1-(4-N,N'-dimethylcarbamoylphenyl)-3-(3-pyridyl-2-ethyl)pyrido[2,3-d]pyrimidine-2,4(1H,3H)-dione, 1-(3-N,N'-dimethylcarbamoylphenyl)-3-(2quinolinylmethyl)pyrido[2,3-d]pyrimidine-2,4(1H,3H)-dione, 1-(4-N,N'-dimethylcarbamoylphenyl)-3-(2-quinolinyl-2-ethyl)pyrido[2,3-d]pyrimidine-2,4(1H,3H)-dione, 1-(2-N,N'-dimethylcarbamoylphenyl)-3-[4-(2,6-dimethyl)pyridylmethyl]pyrido[2,3-d]pyrimidine-2,4(1H,3H)-dione, 1-(4-N,N'-dimethylcarbamoylphenyl)-3-[4-(2,6-dimethyl)pyridyl-2-ethyl]pyrido[2,3-d]pyrimidine-2,4(1H,3H)-dione, 1-(2-N,N'-dimethylcarbamoylphenyl)-3-(4-pyridonylmethyl)pyrido[2,3-d]pyrimidine-2,4(1H,3H)-dione, 1-(3-N,N'-dimethylcarbamoylphenyl)-3-[4-(2-pyridonyl)-2-ethyl]pyrido[2,3-d]pyrimidine-2,4(1H,3H)-dione, 1-(4-N,N'-dimethylcarbamoylphenyl)-3-[4-(2-pyridonyl-1-methyl)methyl]pyrido[2,3-d]pyrimidine-2,4(1H,3H)-dione, 1-(2-N,N'-dimethylcarbamoylphenyl)-3-[5-(2-pyridonyl)methyl]pyrido[2,3-d]pyrimidine-2,4(1H,3H)-dione, 1-(3-N,N'-dimethylcarbamoylphenyl)-3-[5-(2-pyridonyl)-2-ethyl]pyrido[2,3-d]pyrimidine-2,4(1H,3H)-dione, 1-(4-N,N'-dimethylcarbamoylphenyl)-3-[5-(2-pyridonyl)-2-ethyl]pyrido[2,3-d]pyrimidine-2,4(1H,3H)-dione, 1-(3-N,N'-dimethylcarbamoylphenyl)-3-[5-(2-pyridonyl-1-methyl)-2-ethyl]pyrido[2,3-d]pyrimidine-2,4(1H,3H)-dione, and 1-(3-N,N'-dimethylcarbamoylphenyl)-3-[5-(2-pyridonyl-1-methyl)methyl]pyrido[2,3-d]pyrimidine-2,4(1H,3H)-dione.

16D. Formula I, Where Y is —CH$_2$—

By following the procedures of Example 16A and substituting 1-(3-methoxycarbonylphenyl)-3-(3-pyridylmethyl)pyrido[2,3-d]pyrimidine-2,4(1H,3H)-dione with the following:

1-(2-methoxycarbonylphenyl)-3-(phenyl-2-ethyl)-pyrido[2,3-d]pyrimidine-2(1H,3H)-one, 1-(2-methoxycarbonylphenyl)-3-(benzyl)pyrido[2,3-d]pyrimidine-2(1H,3H)-one, 1-(2-methoxycarbonylphenyl)-3-(4-pyridyl-2-ethyl)-pyrido[2,3-d]pyrimidine-2(1H,3H)-one, 1-(3-methoxycarbonylphenyl)-3-(3-pyridylmethyl)-pyrido[2,3-d]pyrimidine-2(1H,3H)-one, 1-(4-methoxycarbonylphenyl)-3-(3-pyridyl-2-ethyl)-pyrido[2,3-d]pyrimidine-2(1H,3H)-one, 1-(3-methoxycarbonylphenyl)-3-(2-quinolinylmethyl)-pyrido[2,3-d]pyrimidine-2(1H,3H)-one, 1-(4-methoxycarbonylphenyl)-3-(2-quinolinyl-2-ethyl)-pyrido[2,3-d]pyrimidine-2(1H,3H)-one, 1-(2-methoxycarbonylphenyl)-3-[4-(2,6-dimethyl)-pyridylmethyl]pyrido[2,3-d]pyrimidine-2(1H,3H)-one, 1-(4-methoxycarbonylphenyl)-3-[4-(2,6-dimethyl)pyridyl-2-ethyl]pyrido[2,3-d]pyrimidine-2(1H,3H)-one, 1-(2-methoxycarbonylphenyl)-3-(4-pyridonylmethyl)-pyrido[2,3-d]pyrimidine-2(1H,3H)-one, 1-(3-methoxycarbonylphenyl)-3-[4-(2-pyridonyl)-2-ethyl]pyrido[2,3-d]pyrimidine-2(1H,3H)-one, 1-(4-methoxycarbonylphenyl)-3-[4-(2-pyridonyl-1-methyl)methyl]pyrido[2,3-d]pyrimidine-2(1H,3H)-one, 1-(2-methoxycarbonylphenyl)-3-[5-(2-pyridonyl)methyl]pyrido[2,3-d]pyrimidine-2(1H,3H)-one, 1-(3-methoxycarbonylphenyl)-3-[5-(2-pyridonyl)-2-ethyl]pyrido[2,3-d]pyrimidine-2(1H,3H)-one, 1-(4-methoxycarbonylphenyl)-3-[5-(2-pyridonyl)-2-ethyl]pyrido[2,3-d]pyrimidine-2(1H,3H)-one, 1-(3-methoxycarbonylphenyl)-3-[5-(2-pyridonyl-1-methyl)-2-ethyl]pyrido[2,3-d]pyrimidine-2(1H,3H)-one, and 1-(3-methoxycarbonylphenyl)-3-[5-(2-pyridonyl-1-methyl)methyl]pyrido[2,3-d]pyrimidine-2(1H,3H)-one;

there are obtained the following compounds:

1-(2-N,N'-dimethylcarbamoylphenyl)-3-(phenyl-2-ethyl)pyrido[2,3-d]pyrimidine-2(1H,3H)-one, 1-(2-N,N'-dimethylcarbamoylphenyl)-3-(benzyl)-pyrido[2,3-d]pyrimidine-2(1H,3H)-one, 1-(2-N,N'-dimethylcarbamoylphenyl)-3-(4-pyridyl-2-ethyl)pyrido[2,3-d]pyrimidine-2(1H,3H)-one, 1-(3-N,N'-dimethylcarbamoylphenyl)-3-(3-pyridylmethyl)pyrido[2,3-d]pyrimidine-2(1H,3H)-one, 1-(4-N,N'-dimethylcarbamoylphenyl)-3-(3-pyridyl-2-ethyl)pyrido[2,3-d]pyrimidine-2(1H,3H)-one, 1-(3-N,N'-dimethylcarbamoylphenyl)-3-(2-quinolinylmethyl)pyrido[2,3-d]pyrimidine-2(1H,3H)-one, 1-(4-N,N'-dimethylcarbamoylphenyl)-3-(2-quinolinyl-2-ethyl)pyrido[2,3-d]pyrimidine-2(1H,3H)-one, 1-(2-N,N'-dimethylcarbamoylphenyl)-3-[4-(2,6-dimethyl)pyridylmethyl]pyrido[2,3-d]pyrimidine-2(1H,3H)-one, 1-(4-N,N'-dimethylcarbamoylphenyl)-3-[4-(2,6-dimethyl)pyridyl-2-ethyl]pyrido[2,3-d]pyrimidine-2(1H,3H)-one, 1-(2-N,N'-dimethylcarbamoylphenyl)-3-(4-pyridonylmethyl)pyrido[2,3-d]pyrimidine-2(1H,3H)-one, 1-(3-N,N'-dimethylcarbamoylphenyl)-3-[4-(2-pyridonyl)-2ethyl]pyrido[2,3-d]pyrimidine-2(1H,3H)-one, 1-(4-N,N'-dimethylcarbamoylphenyl)-3-[4-(2-pyridonyl-1-methyl)methyl]pyrido[2,3-d]pyrimidine-2(1H,3H)-one, 1-(2-N,N'-dimethylcarbamoylphenyl)-3-[5-(2-pyridonyl)methyl]pyrido[2,3-d]pyrimidine-2(1H,3H)-one, 1-(3-N,N'-dimethylcarbamoylphenyl)-3-[5-(2-pyridonyl)-2ethyl]pyrido[2,3-d]pyrimidine-2(1H,3H)-one, 1-(4-N,N'-dimethylcarbamoylphenyl)-3-[5-(2-pyridonyl)-2ethyl]pyrido[2,3-d]pyrimidine-2(1H,3H)-one, 1(3-N,N'-dimethylcarbamoylphenyl)-3-[5-(2-pyridonyl-1-methyl)-2-ethyl]pyrido[2,3-d]pyrimidine-2(1H,3H)-one, and 1-(3-N,N'-dimethylcarbamoylphenyl)-3-[5-(2-pyridonyl-1-methyl)methyl]pyrido[2,3-d]pyrimidine-2(1H,3H)-one.

EXAMPLE 17

Preparation of 1-(3-Methylsulfinylphenyl)-3-(4-pyridylmethyl)-pyrido[2,3-d]pyrimidine-2,4(1H,3H)-dione 17A. Formula I, Where R$^3$ is —S(O)—CH$^3$ 1-(3-Methylthiophenyl)-3-(4-pyridylmethyl)-pyrido[2,3-d]pyrimidine-2,4(1H,3H)-dione (100 mg, 0.27 mmole), prepared, e.g., as described in Example 5B, was dissolved in methylene chloride (20 ml) and cooled to 0° C. m-Chloroperoxybenzoic acid (45 mg, 0.27 mmole) was added to the solution. The solution was stirred for 2 hours at 0° C. The solution was then washed with a 10% solution of Na$_2$SO$_3$ (2 ml) followed by a wash with saturated NaHCO$_3$ (10 ml). The organic and aqueous phases were separated and the organic phase was dried with MgSO$_4$. The solvents were removed and the residue purified by preparative thin-layer chromatography (ethyl acetate as eluent) yielding 51 mg (0.13 mmole, 48% yield) of 1-(3-methylsulfinylphenyl)-3-(4-pyridylmethyl)pyrido[2,3-d]pyrimidine-2,4(1H,3H)-dione, as a white solid, (mp 218°-219° C.).

17B. Formula I, where Y is —C(O)—

By following the procedures of Example 17A and substituting 1-(3-methylthiophenyl)-3-(4-pyridylmethyl)pyrido[2,3-d]pyrimidine-2,4(1H,3H)-dione with the following:

1-(2-methylthiophenyl)-3-(4-pyridyl-2-ethyl)pyrido[2,3-d]pyrimidine-2,4(1H,3H)-dione, 1-(3-methylthiophenyl)-3-(3-pyridylmethyl)pyrido[2,3-d]pyrimidine-2,4(1H,3H)-dione, 1-(4-methylthiophenyl)-3-(3-pyridyl-2-ethyl)pyrido[2,3-d]pyrimidine-2,4(1H,3H)-dione, 1-(3-methylthiophenyl)-3-(2-quinolinylmethyl)-pyrido[2,3-d]pyrimidine-2,4(1H,3H)-dione, 1-(4-methylthiophenyl)-3-(2-quinolinyl-2-ethyl)-pyrido[2,3-d]pyrimidine-2,4(1H,3H)-dione, 1-(2-methylthiophenyl)-3-[4-(2,6-dimethyl)pyridylmethyl]pyrido[2,3-d]pyrimidine-2,4(1H,3H)-dione,
1-(4-methylthiophenyl)-3-[4-(2,6-dimethyl)pyridyl-2-ethyl]pyrido[2,3-d]pyrimidine-2,4(1H,3H)-dione,
1-(2-methylthiophenyl)-3-(4-pyridonylmethyl)-pyrido[2,3-d]pyrimidine-2,4(1H,3H)-dione,
1-(3-methylthiophenyl)-3-[4-(2-pyridonyl)-2-ethyl]-pyrido[2,3-d]pyrimidine-2,4(1H,3H)-dione,
1-(4-methylthiophenyl)-3-[4-(2-pyridonyl-1-methyl)methyl]pyrido[2,3-d]pyrimidine-2,4(1H,3H)-dione,
1-(2-methylthiophenyl)-3-[5-(2-pyridonyl)methyl]-pyrido[2,3-d]pyrimidine-2,4(1H,3H)-dione,
1-(3-methylthiophenyl)-3-[5-(2-pyridonyl)-2-ethyl]-pyrido[2,3-d]pyrimidine-2,4(1H,3H)-dione,
1-(4-methylthiophenyl)-3-[5-(2-pyridonyl)-2-ethyl]-pyrido[2,3-d]pyrimidine-2,4(1H,3H)-dione,
1-(3-methylthiophenyl)-3-[5-(2-pyridonyl-1-methyl)-2-ethyl]pyrido[2,3-d]pyrimidine-2,4(1H,3H)-dione,
1-(3-methylthiophenyl)-3-[5-(2-pyridonyl-1-methyl)methyl]pyrido[2,3-d]pyrimidine-2,4(1H,3H)-dione,
1-(2-methylthiophenyl)-3-[4-(2-pyranonyl)methyl]-pyrido[2,3-d]pyrimidine-2,4(1H,3H)-dione,
1-(3-methylthiophenyl)-3-[4-(2-pyranonyl)-2-ethyl]-pyrido[2,3-d]pyrimidine-2,4(1H,3H)-dione, and
1-(4-methylthiophenyl)-3-[4-(2-pyranonyl)-2-ethyl]-pyrido[2,3-d]pyrimidine-2,4(1H,3H)-dione;
there are obtained the following compounds:
1-(2-methylsulfinylphenyl)-3-(4-pyridyl-2-ethyl)-pyrido[2,3-d]pyrimidine-2,4(1H,3H)-dione,
1-(3-methylsulfinylphenyl)-3-(3-pyridylmethyl)-pyrido[2,3-d]pyrimidine-2,4(1H,3H)-dione,
1-(4-methylsulfinylphenyl)-3-(3-pyridyl-2-ethyl)-pyrido[2,3-d]pyrimidine-2,4(1H,3H)-dione,
1-(3-methylsulfinylphenyl)-3-(2-quinolinylmethyl)-pyrido[2,3-d]pyrimidine-2,4(1H,3H)-dione,
1-(4-methylsulfinylphenyl)-3-(2-quinolinyl-2-ethyl)-pyrido[2,3-d]pyrimidine-2,4(1H,3H)-dione,
1-(2-methylsulfinylphenyl)-3-[4-(2,6-dimethyl)pyridylmethyl]pyrido[2,3-d]pyrimidine-2,4(1H,3H)-dione,
1-(4-methylsulfinylphenyl)-3-[4-(2,6-dimethyl)pyridyl-2-ethyl]pyrido[2,3-d]pyrimidine-2,4(1H,3H)-dione,
1-(2-methylsulfinylphenyl)-3-(4-pyridonylmethyl)-pyrido[2,3-d]pyrimidine-2,4(1H,3H)-dione,
1-(3-methylsulfinylphenyl)-3-[4-(2-pyridonyl)-2-ethyl]-pyrido[2,3-d]pyrimidine-2,4(1H,3H)-dione,
1-(4-methylsulfinylphenyl)-3-[4-(2-pyridonyl-1-methyl)methyl]pyrido[2,3-d]pyrimidine-2,4(1H,3H)-dione,
1-(2-methylsulfinylphenyl)-3-[5-(2-pyridonyl)methyl]-pyrido[2,3-d]pyrimidine-2,4(1H,3H)-dione,
1-(3-methylsulfinylphenyl)-3-[5-(2-pyridonyl)-2-ethyl]-pyrido[2,3-d]pyrimidine-2,4(1H,3H)-dione,
1-(4-methylsulfinylphenyl)-3-[5-(2-pyridonyl)-2-ethyl]-pyrido[2,3-d]pyrimidine-2,4(1H,3H)-dione,
1-(3-methylsulfinylphenyl)-3-[5-(2-pyridonyl-1-methyl)2-ethyl]pyrido[2,3-d]pyrimidine-2,4(1H,3H)-dione,
1-(3-methylsulfinylphenyl)-3-[5-(2-pyridonyl-1-methyl)methyl]pyrido[2,3-d]pyrimidine-2,4(1H,3H)-dione,
1-(2-methylsulfinylphenyl)-3-[4-(2-pyranonyl)methyl]-pyrido[2,3-d]pyrimidine-2,4(1H,3H)-dione,
1-(3-methylsulfinylphenyl)-3-[4-(2-pyranonyl)-2-ethyl]-pyrido[2,3-d]pyrimidine-2,4(1H,3H)-dione, and
1-(4-methylsulfinylphenyl)-3-[4-(2-pyranonyl)-2-ethyl]-pyrido[2,3-d]pyrimidine-2,4(1H,3H)-dione.

17C. Formula I, Where Y is —CH$_2$—

By following the procedures of Example 17A and substituting 1-(3-methylthiophenyl)-3-(4-pyridylmethyl)pyrido[2,3-d]pyrimidine-2,4(1H,3H)-dione with the following:
1-(2-methylthiophenyl)-3-(phenyl-2-ethyl)pyrido[2,3-d]pyrimidine-2(1H,3H)-one,
1-(2-methylthiophenyl)-3-(benzyl-2-ethyl)pyrido[2,3-d]pyrimidine-2(1H,3H)-one,
1-(2-methylthiophenyl)-3-(4-pyridyl-2-ethyl)pyrido[2,3-d]pyrimidine-2(1H,3H)-one,
1-(3-methylthiophenyl)-3-(3-pyridylmethyl)pyrido[2,3-d]pyrimidine-2(1H,3H)-one,
1-4-methylthiophenyl)-3-(3-pyridyl-2-ethyl)pyrido[2,3-d]pyrimidine-2(1H,3H)-one,
1-(3-methylthiophenyl)-3-(2-quinolinylmethyl)-pyrido[2,3-d]pyrimidine-2(1H,3H)-one,
1-(4-methylthiophenyl)-3-(2-quinolinyl-2-ethyl)-pyrido[2,3-d]pyrimidine-2(1H,3H)-one,
1-(2-methylthiophenyl)-3-[4-(2,6-dimethyl)pyridylmethyl]pyrido[2,3-d]pyrimidine-2(1H,3H)-one,
1-(4-methylthiophenyl)-3-[4-(2,6-dimethyl)pyridyl-2ethyl]pyrido[2,3-d]pyrimidine-2(1H,3H)-one,
1-(2-methylthiophenyl)-3-(4-pyridonylmethyl)-pyrido[2,3-d]pyrimidine-2(1H,3H)-one,
1-(3-methylthiophenyl)-3-[4-(2-pyridonyl)-2-ethyl]-pyrido[2,3-d]pyrimidine-2(1H,3H)-one,
1-(4-methylthiophenyl)-3-[4-(2-pyridonyl-1-methyl)methyl]pyrido[2,3-d]pyrimidine-2(1H,3H)-one,
1-(2-methylthiophenyl)-3-[5-(2-pyridonyl)methyl]-pyrido[2,3-d]pyrimidine-2(1H,3H)-one,
1-(3-methylthiophenyl)-3-[5-(2-pyridonyl)-2-ethyl]-pyrido[2,3-d]pyrimidine-2(1H,3H)-one,
1-(4-methylthiophenyl)-3-[5-(2-pyridonyl)-2-ethyl]-pyrido[2,3-d]pyrimidine-2(1H,3H)-one,
1-(3-methylthiophenyl)-3-[5-(2-pyridonyl-1-methyl)-2-ethyl]pyrido[2,3-d]pyrimidine-2(1H,3H)-one,
1-(3-methylthiophenyl)-3-[5-(2-pyridonyl-1-methyl)methyl]pyrido[2,3-d]pyrimidine-2(1H,3H)-one,
1-(2-methylthiophenyl)-3-[4-(2-pyranonyl)methyl]-pyrido[2,3-d]pyrimidine-2(1H,3H)-one,
1-(3-methylthiophenyl)-3-[4-(2-pyranonyl)-2-ethyl]-pyrido[2,3-d]pyrimidine-2(1H,3H)-one, and
1-(4-methylthiophenyl)-3-[4-(2-pyranonyl)-2-ethyl]-pyrido[2,3-d]pyrimidine-2(1H,3H)-one;
there are obtained the following compounds:
1-(2-methylsulfinylphenyl)-3-(phenyl-2-ethyl)-pyrido[2,3-d]pyrimidine-2(1H,3H)-one,
1-(2-methylsulfinylphenyl)-3-(benzyl-2-ethyl)-pyrido[2,3-d]pyrimidine-2(1H,3H)-one,
1-(2-methylsulfinylphenyl)-3-(4-pyridyl-2-ethyl)-pyrido[2,3-d]pyrimidine-2(1H,3H)-one,
1-(3-methylsulfinylphenyl)-3-(3-pyridylmethyl)-pyrido[2,3-d]pyrimidine-2(1H,3H)-one,
1-(4-methylsulfinylphenyl)-3-(3-pyridyl-2-ethyl)-pyrido[2,3-d]pyrimidine-2(1H,3H)-one,
1-(3-methylsulfinylphenyl)-3-(2-quinolinylmethyl)-pyrido[2,3-d]pyrimidine-2(1H,3H)-one,
1-(4-methylsulfinylphenyl)-3-(2-quinolinyl-2-ethyl)-pyrido[2,3-d]pyrimidine-2(1H,3H)-one,
1-(2-methylsulfinylphenyl)-3-[4-(2,6-dimethyl)pyridylmethyl]pyrido[2,3-d]pyrimidine-2(1H,3H)-one,
1-(4-methylsulfinylphenyl)-3-[4-(2,6-dimethyl)pyridyl-2-ethyl]pyrido[2,3-d]pyrimidine-2(1H,3H)-one,
1-(2-methylsulfinylphenyl)-3-(4-pyridonylmethyl)-pyrido[2,3-d]pyrimidine-2(1H,3H)-one,
1-(3-methylsulfinylphenyl)-3-[4-(2-pyridonyl)-2-ethyl]-pyrido[2,3-d]pyrimidine-2(1H,3H)-one, 1-(4-methylsulfinylphenyl)-3-[4-(2-pyridonyl-1-methyl)methyl]pyrido[2,3-d]pyrimidine-2(1H,3H)-one,
1-(2-methylsulfinylphenyl)-3-[5-(2-pyridonyl)methyl]pyrido[2,3-d]pyrimidine-2(1H,3H)-one,
1-(3-methylsulfinylphenyl)-3-[5-(2-pyridonyl)-2-ethyl]pyrido[2,3-d]pyrimidine-2(1H,3H)-one,
1-(4-methylsulfinylphenyl)-3-[5-(2-pyridonyl)-2-ethyl]pyrido[2,3-d]pyrimidine-2(1H,3H)-one,
1-(3-methylsulfinylphenyl)-3-[5-(2-pyridonyl-1-methyl)-2-ethyl]pyrido[2,3-d]pyrimidine-2(1H,3H)-one,
1-(3-methylsulfinylphenyl)-3-[5-(2-pyridonyl-1-methyl)methyl]pyrido[2,3-d]pyrimidine-2(1H,3H)-one,
1-(2-methylsulfinylphenyl)-3-[4-(2-pyranonyl)methyl]pyrido[2,3-d]pyrimidine-2(1H,3H)-one,
1-(3-methylsulfinylphenyl)-3-[4-(2-pyranonyl)-2-ethyl]pyrido[2,3-d]pyrimidine-2(1H,3H)-one, and
1-(4-methylsulfinylphenyl)-3-[4-(2-pyranonyl)-2-ethyl]pyrido[2,3-d]pyrimidine-2(1H,3H)-one.

EXAMPLE 18

Preparation of 1-(3-Methylsulfonylphenyl)-3-(4-pyridylmethyl)-pyrido[2,3-d]pyrimidine-2,4(1H,3H)-dione 18A. Formula I, Where $R^3$ is —S(O$_2$)—CH$^3$ 1-(3-Methylthiophenyl)-3-(4-pyridylmethyl)-pyrido[2,3-d]pyrimidine-2,4(1H,3H)-dione (250 mg, 0.664 mmole), prepared, e.g., as described in Example 5B, was dissolved in methanol (3 ml) and cooled to 0° C. To this solution, a 50% solution of 2KHSO$_5$.KHSO$_4$.K$_2$SO$_4$ in H$_2$O, (this reagent is commercially available under the trademark of "OXONE®" from the Aldrich Chemical Company), (1.22 g, 1.99 mmole) was added. A cloudy slurry was formed and stirred at room temperature for 4 hours. The reaction mixture was diluted by adding H$_2$O (2.4 ml) and extracted three times with methylene chloride (3×5 ml). The organic phases were combined and dried over Na$_2$SO$_4$, followed by filtration. The solvent was removed and the residue was dissolved in ethyl acetate/ethyl ether. The product was recrystallized out of the solution yielding 190 mg (0.465 mmole, 79% yield) of 1-(3-methylsulfonylphenyl)-3-(4-pyridylmethyl)pyrido[2,3-d]pyrimidine-2,4(1H,3H)-dione (mp 254°–256° C.) as a white solid.

18B. Formula I, Where Y is —C(O)—

By following the procedures of Example 18A and substituting 1-(3-methylthiophenyl)-3-(4-pyridylmethyl)pyrido[2,3-d]pyrimidine-2,4(1H,3H)-dione with the following:

1-(2-methylthiophenyl)-3-(4-pyridyl-2-ethyl)pyrido[2,3-d]pyrimidine-2,4(1H,3H)-dione,
1-(3-methylthiophenyl)-3-(3-pyridylmethyl)pyrido[2,3-d]pyrimidine-2,4(1H,3H)-dione,
1-(4-methylthiophenyl)-3-(3-pyridyl-2-ethyl)pyrido[2,3-d]pyrimidine-2,4(1H,3H)-dione,
1-(3-methylthiophenyl)-3-(2-quinolinylmethyl)-pyrido[2,3-d]pyrimidine-2,4(1H,3H)-dione,
1-(4-methylthiophenyl)-3-(2-quinolinyl-2-ethyl)-pyrido[2,3-d]pyrimidine-2,4(1H,3H)-dione,
1-(2-methylthiophenyl)-3-[4-(2,6-dimethyl)pyridylmethyl]pyrido[2,3-d]pyrimidine-2,4(1H,3H)-dione,
1-(4-methylthiophenyl)-3-[4-(2,6-dimethyl)pyridyl-2-ethyl]pyrido[2,3-d]pyrimidine-2,4(1H,3H)-dione,
1-(2-methylthiophenyl)-3-(4-pyridonylmethyl)-pyrido[2,3-d]pyrimidine-2,4(1H,3H)-dione,
1-(3-methylthiophenyl)-3-[4-(2-pyridonyl)-2-ethyl]-pyrido[2,3-d]pyrimidine-2,4(1H,3H)-dione,
1-(4-methylthiophenyl)-3-[4-(2-pyridonyl-1-methyl)methyl]pyrido[2,3-d]pyrimidine-2,4(1H,3H)-dione,
1-(2-methylthiophenyl)-3-[5-(2-pyridonyl)methyl]-pyrido[2,3-d]pyrimidine-2,4(1H,3H)-dione,
1-(3-methylthiophenyl)-3-[5-(2-pyridonyl)-2-ethyl]-pyrido[2,3-d]pyrimidine-2,4(1H,3H)-dione,
1-(4-methylthiophenyl)-3-[5-(2-pyridonyl)-2-ethyl]-pyrido[2,3-d]pyrimidine-2,4(1H,3H)-dione,
1-(3-methylthiophenyl)-3-[5-(2-pyridonyl-1-methyl)-2-ethyl]pyrido[2,3-d]pyrimidine-2,4(1H,3H)-dione,
1-(3-methylthiophenyl)-3-[5-(2-pyridonyl-1-methyl)methyl]pyrido[2,3-d]pyrimidine-2,4(1H,3H)-dione,
1-(2-methylthiophenyl)-3-[4-(2-pyranonyl)methyl]-pyrido[2,3-d]pyrimidine-2,4(1H,3H)-dione,
1-(3-methylthiophenyl)-3-[4-(2-pyranonyl)-2-ethyl]-pyrido[2,3-d]pyrimidine-2,4(1H,3H)-dione, and
1-(4-methylthiophenyl)-3-[4-(2-pyranonyl)-2-ethyl]-pyrido[2,3-d]pyrimidine-2,4(1H,3H)-dione;

there are obtained the following compounds:

1-(2-methylsulfonylphenyl)-3-(4-pyridyl-2-ethyl)-pyrido[2,3-d]pyrimidine-2,4(1H,3H)-dione,
1-(3-methylsulfonylphenyl)-3-(3-pyridylmethyl)-pyrido[2,3-d]pyrimidine-2,4(1H,3H)-dione,
1-(4-methylsulfonylphenyl)-3-(3-pyridyl-2-ethyl)-pyrido[2,3-d]pyrimidine-2,4(1H,3H)-dione,
1-(3-methylsulfonylphenyl)-3-(2-quinolinylmethyl)-pyrido[2,3-d]pyrimidine-2,4(1H,3H)-dione,
1-(4-methylsulfonylphenyl)-3-(2-quinolinyl-2-ethyl)-pyrido[2,3-d]pyrimidine-2,4(1H,3H)-dione,
1-(2-methylsulfonylphenyl)-3-[4-(2,6-dimethyl)pyridylmethyl]pyrido[2,3-d]pyrimidine-2,4(1H,3H)-dione,
1-(4-methylsulfonylphenyl)-3-[4-(2,6-dimethyl)pyridyl-2-ethyl]pyrido[2,3-d]pyrimidine-2,4(1H,3H)-dione,
1-(2-methylsulfonylphenyl)-3-(4-pyridonylmethyl)-pyrido[2,3-d]pyrimidine-2,4(1H,3H)-dione,
1-(3-methylsulfonylphenyl)-3-[4-(2-pyridonyl)-2-ethyl]pyrido[2,3-d]pyrimidine-2,4(1H,3H)-dione,
1-(4-methylsulfonylphenyl)-3-[4-(2-pyridonyl-1-methyl)methyl]pyrido[2,3-d]pyrimidine-2,4(1H,3H)-dione,
1-(2-methylsulfonylphenyl)-3-[5-(2-pyridonyl)methyl]pyrido[2,3-d]pyrimidine-2,4(1H,3H)-dione,
1-(3-methylsulfonylphenyl)-3-[5-(2-pyridonyl)-2-ethyl]pyrido[2,3-d]pyrimidine-2,4(1H,3H)-dione,
1-(4-methylsulfonylphenyl)-3-[5-(2-pyridonyl)-2-ethyl]pyrido[2,3-d]pyrimidine-2,4(1H,3H)-dione,
1-(3-methylsulfonylphenyl)-3-[5-(2-pyridonyl-1-methyl)2-ethyl]pyrido[2,3-d]pyrimidine-2,4(1H,3H)-dione,
1-(3-methylsulfonylphenyl)-3-[5-(2-pyridonyl-1-methyl)methyl]pyrido[2,3-d]pyrimidine-2,4(1H,3H)-dione,
1-(2-methylsulfonylphenyl)-3-[4-(2-pyranonyl)methyl]pyrido[2,3-d]pyrimidine-2,4(1H,3H)-dione,
1-(3-methylsulfonylphenyl)-3-[4-(2-pyranonyl)-2-ethyl]pyrido[2,3-d]pyrimidine-2,4(1H,3H)-dione, and
1-(4-methylsulfonylphenyl)-3-[4-(2-pyranonyl)-2-ethyl]pyrido[2,3-d]pyrimidine-2,4(1H,3H)-dione.

18C. Formula I, Where Y is —CH$_2$—

By following the procedures of Example 18A and substituting 1-(3-methylthiophenyl)-3-(4-pyridylmethyl)pyrido[2,3-d]pyrimidine-2,4(1H,3H)-dione with the following:

1-(2-methylthiophenyl)-3-(phenyl-2-ethyl)pyrido[2,3-d]pyrimidine-2(1H,3H)-one,
1-(2-methylthiophenyl)-3-(benzyl)pyrido[2,3-d]pyrimidine-2(1H,3H)-one,
1-(2-methylthiophenyl)-3-(4-pyridyl-2-ethyl)pyrido[2,3-d]pyrimidine-2(1H,3H)-one,
1-(3-methylthiophenyl)-3-(3-pyridylmethyl)pyrido[2,3-d]pyrimidine-2(1H,3H)-one,
1-(4-methylthiophenyl)-3-(3-pyridyl-2-ethyl)pyrido[2,3-d]pyrimidine-2(1H,3H)-one,
1-(3-methylthiophenyl)-3-(2-quinolinylmethyl)-pyrido[2,3-d]pyrimidine-2(1H,3H)-one,
1-(4-methylthiophenyl)-3-(2-quinolinyl-2-ethyl)-pyrido[2,3-d]pyrimidine-2(1H,3H)-one,
1-(2-methylthiophenyl)-3-[4-(2,6-dimethyl)pyridylmethyl]pyrido[2,3-d]pyrimidine-2(1H,3H)-one,
1-(4-methylthiophenyl)-3-[4-(2,6-dimethyl)pyridyl-2-ethyl]pyrido[2,3-d]pyrimidine-2(1H,3H)-one,
1-(2-methylthiophenyl)-3-(4-pyridonylmethyl)-pyrido[2,3-d]pyrimidine-2(1H,3H)-one,
1-(3-methylthiophenyl)-3-[4-(2-pyridonyl)-2-ethyl]-pyrido[2,3-d]pyrimidine-2(1H,3H)-one,
1-(4-methylthiophenyl)-3-[4-(2-pyridonyl-1-methyl)methyl]pyrido[2,3-d]pyrimidine-2(1H,3H)-one,
1-(2-methylthiophenyl)-3-[5-(2-pyridonyl)methyl]-pyrido[2,3-d]pyrimidine-2(1H,3H)-one,
1-(3-methylthiophenyl)-3-[5-(2-pyridonyl)-2-ethyl]-pyrido[2,3-d]pyrimidine-2(1H,3H)-one,
1-(4-methylthiophenyl)-3-[5-(2-pyridonyl)-2-ethyl]-pyrido[2,3-d]pyrimidine-2(1H,3H)-one,
1-(3-methylthiophenyl)-3-[5-(2-pyridonyl-1-methyl)-2-ethyl]pyrido[2,3-d]pyrimidine-2(1H,3H)-one,
1-(3-methylthiophenyl)-3-[5-(2-pyridonyl-1-methyl)methyl]pyrido[2,3-d]pyrimidine-2(1H,3H)-one,
1-(2-methylthiophenyl)-3-[4-(2-pyranonyl)methyl]-pyrido[2,3-d]pyrimidine-2(1H,3H)-one,
1-(3-methylthiophenyl)-3-[4-(2-pyranonyl)-2-ethyl]-pyrido[2,3-d]pyrimidine-2(1H,3H)-one, and
1-(4-methylthiophenyl)-3-[4-(2-pyranonyl)-2-ethyl]-pyrido[2,3-d]pyrimidine-2(1H,3H)-one;
there are obtained the following compounds:
1-(2-methylsulfonylphenyl)-3-(phenyl-2-ethyl)-pyrido[2,3-d]pyrimidine-2(1H,3H)-one,
1-(2-methylsulfonylphenyl)-3-(benzyl)pyrido[2,3-d]pyrimidine-2(1H,3H)-one,
1-(2-methylsulfonylphenyl)-3-(4-pyridyl-2-ethyl)-pyrido[2,3-d]pyrimidine-2(1H,3H)-one,
1-(3-methylsulfonylphenyl)-3-(3-pyridylmethyl)-pyrido[2,3-d]pyrimidine-2(1H,3H)-one,
1-(4-methylsulfonylphenyl)-3-(3-pyridyl-2-ethyl)-pyrido[2,3-d]pyrimidine-2(1H,3H)-one,
1-(3-methylsulfonylphenyl)-3-(2-quinolinylmethyl)-pyrido[2,3-d]pyrimidine-2(1H,3H)-one,
1-(4-methylsulfonylphenyl)-3-(2-quinolinyl-2-ethyl)-pyrido[2,3-d]pyrimidine-2(1H,3H)-one,
1-(2-methylsulfonylphenyl)-3-[4-(2,6-dimethyl)pyridylmethyl]pyrido[2,3-d]pyrimidine-2(1H,3H)-one,
1-(4-methylsulfonylphenyl)-3-[4-(2,6-dimethyl)pyridyl-2-ethyl]pyrido[2,3-d]pyrimidine-2(1H,3H)-one,
1-(2-methylsulfonylphenyl)-3-(4-pyridonylmethyl)-pyrido[2,3-d]pyrimidine-2(1H,3H)-one,
1-(3-methylsulfonylphenyl)-3-[4-(2-pyridonyl)-2-ethyl]-pyrido[2,3-d]pyrimidine-2(1H,3H)-one,
1-(4-methylsulfonylphenyl)-3-[4-(2-pyridonyl-1-methyl)methyl]pyrido[2,3-d]pyrimidine-2(1H,3H)-one,
1-(2-methylsulfonylphenyl)-3-[5-(2-pyridonyl)methyl]pyrido[2,3-d]pyrimidine-2(1H,3H)-one,
1-(3-methylsulfonylphenyl)-3-[5-(2-pyridonyl)-2-ethyl]-pyrido[2,3-d]pyrimidine-2(1H,3H)-one,
1-(4-methylsulfonylphenyl)-3-[5-(2-pyridonyl)-2-ethyl]-pyrido[2,3-d]pyrimidine-2(1H,3H)-one,
1-(3-methylsulfonylphenyl)-3-[5-(2-pyridonyl-1-methyl)2-ethyl]pyrido[2,3-d]pyrimidine-2(1H,3H)-one,
1-(3-methylsulfonylphenyl)-3-[5-(2-pyridonyl-1-methyl)methyl]pyrido[2,3-d]pyrimidine-2(1H,3H)-one,
1-(2-methylsulfonylphenyl)-3-[4-(2-pyranonyl)methyl]-pyrido[2,3-d]pyrimidine-2(1H,3H)-one,
1-(3-methylsulfonylphenyl)-3-[4-(2-pyranonyl)-2-ethyl]-pyrido[2,3-d]pyrimidine-2(1H,3H)-one, and
1-(4-methylsulfonylphenyl)-3-[4-(2-pyranonyl)-2-ethyl]-pyrido[2,3-d]pyrimidine-2(1H,3H)-one.

EXAMPLE 19

Preparation of 1-(3-Hydroxymethylphenyl)-3-(3-pyridylmethyl)-pyrido[2,3-d]pyrimidine-2,4(1H,3H)-dione 19A. Formula I, Where $R^3$ is $-CH_2-OH$ 1-(3-Methoxycarbonylphenyl)-3-(3-pyridylmethyl)-pyrido[2,3-d]pyrimidine-2,4(1H,3H)-dione (200 mg) was dissolved in toluene (5 ml) and cooled to $-78°$ C. under an inert atmosphere. A 1.0M solution of DIBAL-H in toluene, i.e., diisobutylaluminum hydride, (1.0 ml, 1.0 mmole) was added dropwise over a period of 5 minutes and stirred at $-78°$ C. After 30 minutes, the reaction solution was warmed to 0° C., sodium fluoride (0.3 g) and $H_2O$ (1 ml) were added and stirred for minutes. The solution was allowed to warm to room temperature and was stirred vigorously for 30 minutes. Water (5 ml) was added to the solution and the organic phase was isolated and evaporated yielding 45 mg of yellow solid (crude product). The aqueous phase was extracted again with ethyl acetate, followed with another extraction with methylene chloride. The organic layers were collected and evaporated yielding another 65 mg of crude product. The crude products were combined and chromatographed on preparative thin-layer chromatography (10% methanol in methylene chloride) to yield mg (0.069 mmole, 14% yield) of 1-(3-hydroxymethylphenyl)-3-(3-pyridylmethyl)pyrido[2,3-d]pyrimidine-2,4(1H,3H)-dione (mp 197°-198° C.).

19B. Formula I, Where Y is $-C(O)-$

By following the procedures of Example 19A and substituting 1-(3-methoxycarbonylphenyl)-3-(3-pyridylmethyl)pyrido[2,3-d]pyrimidine-2,4(1H,3H)-dione with the following:

1-(2-methoxycarbonylphenyl)-3-(4-pyridyl-2-ethyl)-pyrido[2,3-d]pyrimidine-2,4(1H,3H)-dione,
1-(3-methoxycarbonylphenyl)-3-(3-pyridylmethyl)-pyrido[2,3-d]pyrimidine-2,4(1H,3H)-dione,
1-(4-methoxycarbonylphenyl)-3-(3-pyridyl-2-ethyl)-pyrido[2,3-d]pyrimidine-2,4(1H,3H)-dione,
1-(3-methoxycarbonylphenyl)-3-(2-quinolinylmethyl)-pyrido[2,3-d]pyrimidine-2,4(1H,3H)-dione,
1-(4-methoxycarbonylphenyl)-3-(2-quinolinyl-2-ethyl)-pyrido[2,3-d]pyrimidine-2,4(1H,3H)-dione,
1-(2-methoxycarbonylphenyl)-3-[4-(2,6-dimethyl)-pyridylmethyl]pyrido[2,3-d]pyrimidine-2,4(1H,3H)-dione,
1-(4-methoxycarbonylphenyl)-3-[4-(2,6-dimethyl)pyridyl-2-ethyl]pyrido[2,3-d]pyrimidine-2,4(1H,3H)-dione, 1-(2-methoxycarbonylphenyl)-3-(4-pyridonylmethyl)-pyrido[2,3-d]pyrimidine-2,4(1H,3H)-dione,
1-(3-methoxycarbonylphenyl)-3-[4-(2-pyridonyl)-2-ethyl]pyrido[2,3-d]pyrimidine-2,4(1H,3H)-dione,
1-(4-methoxycarbonylphenyl)-3-[4-(2-pyridonyl-1-methyl)methyl]pyrido[2,3-d]pyrimidine-2,4(1H,3H)-dione,
1-(2-methoxycarbonylphenyl)-3-[5-(2-pyridonyl)methyl]pyrido[2,3-d]pyrimidine-2,4(1H,3H)-dione,
1-(3-methoxycarbonylphenyl)-3-[5-(2-pyridonyl)-2-ethyl]pyrido[2,3-d]pyrimidine-2,4(1H,3H)-dione,
1-(4-methoxycarbonylphenyl)-3-[5-(2-pyridonyl)-2-ethyl]pyrido[2,3-d]pyrimidine-2,4(1H,3H)-dione,
1-(3-methoxycarbonylphenyl)-3-[5-(2-pyridonyl-1-methyl)-2-ethyl]pyrido[2,3-d]pyrimidine-2,4(1H,3H)-dione, and
1-(3-methoxycarbonylphenyl)-3-[5-(2-pyridonyl-1-methyl)methyl]pyrido[2,3-d]pyrimidine-2,4(1H,3H)-dione;

there are obtained the following compounds:
1-(2-hydroxymethylphenyl)-3-(4-pyridyl-2-ethyl)-pyrido[2,3-d]pyrimidine-2,4(1H,3H)-dione,
1-(3-hydroxymethylphenyl)-3-(3-pyridylmethyl)-pyrido[2,3-d]pyrimidine-2,4(1H,3H)-dione,
1-(4-hydroxymethylphenyl)-3-(3-pyridyl-2-ethyl)-pyrido[2,3-d]pyrimidine-2,4(1H,3H)-dione,
1-(3-hydroxymethylphenyl)-3-(2-quinolinylmethyl)-pyrido[2,3-d]pyrimidine-2,4(1H,3H)-dione,
1-(4-hydroxymethylphenyl)-3-(2-quinolinyl-2-ethyl)-pyrido[2,3-d]pyrimidine-2,4(1H,3H)-dione,
1-(2-hydroxymethylphenyl)-3-[4-(2,6-dimethyl)pyridylmethyl]pyrido[2,3-d]pyrimidine-2,4(1H,3H)-dione,
1-(4-hydroxymethylphenyl)-3-[4-(2,6-dimethyl)pyridyl-2-ethyl]pyrido[2,3-d]pyrimidine-2,4(1H,3H)-dione,
1-(2-hydroxymethylphenyl)-3-(4-pyridonylmethyl)-pyrido[2,3-d]pyrimidine-2,4(1H,3H)-dione,
1-(3-hydroxymethylphenyl)-3-[4-(2-pyridonyl)-2-ethyl]pyrido[2,3-d]pyrimidine-2,4(1H,3H)-dione,
1-(4-hydroxymethylphenyl)-3-[4-(2-pyridonyl-1-methyl)methyl]pyrido[2,3-d]pyrimidine-2,4(1H,3H)-dione,
1-(2-hydroxymethylphenyl)-3-[5-(2-pyridonyl)methyl]-pyrido[2,3-d]pyrimidine-2,4(1H,3H)-dione,
1-(3-hydroxymethylphenyl)-3-[5-(2-pyridonyl)-2-ethyl]pyrido[2,3-d]pyrimidine-2,4(1H,3H)-dione,
1-(4-hydroxymethylphenyl)-3-[5-(2-pyridonyl)-2-ethyl]pyrido[2,3-d]pyrimidine-2,4(1H,3H)-dione,
1-(3-hydroxymethylphenyl)-3-[5-(2-pyridonyl-1-methyl)-2-ethyl]pyrido[2,3-d]pyrimidine-2,4(1H,3H)-dione, and
1-(3-hydroxymethylphenyl)-3-[5-(2-pyridonyl-1-methyl)methyl]pyrido[2,3-d]pyrimidine-2,4(1H,3H)-dione.

19C. Formula I, Where Y is —CH$_2$—

By following the procedures of Example 19A and substituting 1-(3-methoxycarbonylphenyl)-3-(3-pyridylmethyl)pyrido[2,3-d]pyrimidine-2,4(1H,3H)-dione with the following:
1-(2-methoxycarbonylphenyl)-3-(phenyl-2-ethyl)-pyrido[2,3-d]pyrimidine-2(1H,3H)-one,
1-(2-methoxycarbonylphenyl)-3-(benzyl)pyrido[2,3-d]pyrimidine-2(1H,3H)-one,
1-(2-methoxycarbonylphenyl)-3-(4-pyridyl-2-ethyl)-pyrido[2,3-d]pyrimidine-2(1H,3H)-one,
1-(3-methoxycarbonylphenyl)-3-(3-pyridylmethyl)-pyrido[2,3-d]pyrimidine-2(1H,3H)-one,
1-(4-methoxycarbonylphenyl)-3-(3-pyridyl-2-ethyl)-pyrido[2,3-d]pyrimidine-2(1H,3H)-one,
1-(3-methoxycarbonylphenyl)-3-(2-quinolinylmethyl)-pyrido[2,3-d]pyrimidine-2(1H,3H)-one,
1-(4-methoxycarbonylphenyl)-3-(2-quinolinyl-2-ethyl)-pyrido[2,3-d]pyrimidine-2(1H,3H)-one,
1-(2-methoxycarbonylphenyl)-3-[4-(2,6-dimethyl)-pyridylmethyl]pyrido[2,3-d]pyrimidine-2(1H,3H)-one,
1-(4-methoxycarbonylphenyl)-3-[4-(2,6-dimethyl)pyridyl-2-ethyl]pyrido[2,3-d]pyrimidine-2(1H,3H)-one,
1-(2-methoxycarbonylphenyl)-3-(4-pyridonylmethyl)-pyrido[2,3-d]pyrimidine-2(1H,3H)-one,
1-(3-methoxycarbonylphenyl)-3-[4-(2-pyridonyl)-2-ethyl]pyrido[2,3-d]pyrimidine-2(1H,3H)-one,
1-(4-methoxycarbonylphenyl)-3-[4-(2-pyridonyl-1-methyl)methyl]pyrido[2,3-d]pyrimidine-2(1H,3H)-one,
1-(2-methoxycarbonylphenyl)-3-[5-(2-pyridonyl)methyl]pyrido[2,3-d]pyrimidine-2(1H,3H)-one,
1-(3-methoxycarbonylphenyl)-3-[5-(2-pyridonyl)-2-ethyl]pyrido[2,3-d]pyrimidine-2(1H,3H)-one,
1-(4-methoxycarbonylphenyl)-3-[5-(2-pyridonyl)-2-ethyl]pyrido[2,3-d]pyrimidine-2(1H,3H)-one,
1-(3-methoxycarbonylphenyl)-3-[5-(2-pyridonyl-1-methyl)-2-ethyl]pyrido[2,3-d]pyrimidine-2(1H,3H)-one, and
1-(3-methoxycarbonylphenyl)-3-[5-(2-pyridonyl-1-methyl)methyl]pyrido[2,3-d]pyrimidine-2(1H,3H)-one;

there are obtained the following compounds:
1-(2-hydroxymethylphenyl)-3-(phenyl-2-ethyl)-pyrido[2,3-d]pyrimidine-2(1H,3H)-one,
1-(2-hydroxymethylphenyl)-3-(benzyl)pyrido[2,3-d]pyrimidine-2(1H,3H)-one,
1-(2-hydroxymethylphenyl)-3-(4-pyridyl-2-ethyl)-pyrido[2,3-d]pyrimidine-2(1H,3H)-one,
1-(3-hydroxymethylphenyl)-3-(3-pyridylmethyl)-pyrido[2,3-d]pyrimidine-2(1H,3H)-one,
1-(4-hydroxymethylphenyl)-3-(3-pyridyl-2-ethyl)-pyrido[2,3-d]pyrimidine-2(1H,3H)-one,
1-(3-hydroxymethylphenyl)-3-(2-quinolinylmethyl)-pyrido[2,3-d]pyrimidine-2(1H,3H)-one,
1-(4-hydroxymethylphenyl)-3-(2-quinolinyl-2-ethyl)-pyrido[2,3-d]pyrimidine-2(1H,3H)-one,
1-(2-hydroxymethylphenyl)-3-[4-(2,6-dimethyl)pyridylmethyl]pyrido[2,3-d]pyrimidine-2(1H,3H)-one,
1-(4-hydroxymethylphenyl)-3-[4-(2,6-dimethyl)pyridyl-2-ethyl]pyrido[2,3-d]pyrimidine-2(1H,3H)-one,
1-(2-hydroxymethylphenyl)-3-(4-pyridonylmethyl)-pyrido[2,3-d]pyrimidine-2(1H,3H)-one,
1-(3-hydroxymethylphenyl)-3-[4-(2-pyridonyl)-2-ethyl]pyrido[2,3-d]pyrimidine-2(1H,3H)-one,
1-(4-hydroxymethylphenyl)-3-[4-(2-pyridonyl-1-methyl)methyl]pyrido[2,3-d]pyrimidine-2(1H,3H)-one,
1-(2-hydroxymethylphenyl)-3-[5-(2-pyridonyl)methyl]-pyrido[2,3-d]pyrimidine-2(1H,3H)-one,
1-(3-hydroxymethylphenyl)-3-[5-(2-pyridonyl)-2-ethyl]pyrido[2,3-d]pyrimidine-2(1H,3H)-one,
1-(4-hydroxymethylphenyl)-3-[5-(2-pyridonyl)-2-ethyl]pyrido[2,3-d]pyrimidine-2(1H,3H)-one,
1-(3-hydroxymethylphenyl)-3-[5-(2-pyridonyl-1-methyl)-2-ethyl]pyrido[2,3-d]pyrimidine-2(1H,3H)-one, and
1-(3-hydroxymethylphenyl)-3-[5-(2-pyridonyl-1-methyl)methyl]pyrido[2,3-d]pyrimidine-2(1H,3H)-one.

EXAMPLE 20

Preparation of
1-(3-Aminophenyl)-3-(4-pyridylmethyl)pyrido[2,3-d]pyrimidine-2,4(1H,3H)-dione 20A. Formula I, Where $R^3$ is $-NH_2$ 1-(3-Nitrophenyl)-3-(4-pyridylmethyl)pyrido[2,3-d]pyrimidine-2,4(1H,3H)-dione (150 mg, 0.4 mmoles), prepared, e.g., in Example 5, was dissolved in methanol (20 ml). A hydrazine hydrate and Raney nickel reagent was prepared by adding hydrazine hydrate (3 ml) to 150 mg of Raney nickel (washed four times with methanol), and methanol (20 ml). The reagent was refluxed for 5 minutes, then the solution of the starting material was added dropwise. The solution was refluxed for 1 hour. The solution was filtered over Celite and washed with methanol. The solvent was removed, the resulting residue was dissolved in methylene chloride, dried over $MgSO_4$, and filtered. The solvent was removed, and the resulting material was purified and isolated by preparative thin-layer chromatography (eluting with ethyl acetate). The solvents were removed and the product triturated with ethyl ether yielding 73 mg (0.26 mmole, 66% yield) of 1-(3-aminophenyl)-3-(4-pyridylmethyl)-pyrido[2,3-d]pyrimidine-2,4(1H,3H)-dione, as white crystals (mp 246° C.).

20B. Formula I, Where Y is $-C(O)-$

By following the procedures of Example 20A and substituting 1-(3-nitrophenyl)-3-(4-pyridylmethyl)-pyrido[2,3-d]pyrimidine-2,4(1H,3H)-dione with the following:

1-(2-nitrophenyl)-3-(4-pyridyl-2-ethyl)pyrido[2,3-d]pyrimidine-2,4(1H,3H)-dione,
1-(3-nitrophenyl)-3-(3-pyridylmethyl)pyrido[2,3-d]pyrimidine-2,4(1H,3H)-dione,
1-(4-nitrophenyl)-3-(3-pyridyl-2-ethyl)pyrido[2,3-d]pyrimidine-2,4(1H,3H)-dione,
1-(3-nitrophenyl)-3-(2-quinolinylmethyl)pyrido[2,3-d]pyrimidine-2,4(1H,3H)-dione,
1-(4-nitrophenyl)-3-(2-quinolinyl-2-ethyl)pyrido[2,3-d]pyrimidine-2,4(1H,3H)-dione,
1-(2-nitrophenyl)-3-[4-(2,6-dimethyl)pyridylmethyl]-pyrido[2,3-d]pyrimidine-2,4(1H,3H)-dione,
1-(4-nitrophenyl)-3-[4-(2,6-dimethyl)pyridyl-2-ethyl]-pyrido[2,3-d]pyrimidine-2,4(1H,3H)-dione,
1-(2-nitrophenyl)-3-(4-pyridonylmethyl)pyrido[2,3-d]pyrimidine-2,4(1H,3H)-dione,
1-(3-nitrophenyl)-3-[4-(2-pyridonyl)-2-ethyl]pyrido[2,3-d]pyrimidine-2,4(1H,3H)-dione,
1-(4-nitrophenyl)-3-[4-(2-pyridonyl-1-methyl)methyl]-pyrido[2,3-d]pyrimidine-2,4(1H,3H)-dione,
1-(2-nitrophenyl)-3-[5-(2-pyridonyl)methyl]pyrido[2,3-d]pyrimidine-2,4(1H,3H)-dione,
1-(3-nitrophenyl)-3-[5-(2-pyridonyl)-2-ethyl]pyrido[2,3-d]pyrimidine-2,4(1H,3H)-dione,
1-(4-nitrophenyl)-3-[5-(2-pyridonyl)-2-ethyl]pyrido[2,3-d]pyrimidine-2,4(1H,3H)-dione,
1-(3-nitrophenyl)-3-[5-(2-pyridonyl-1-methyl)-2-ethyl]-pyrido[2,3-d]pyrimidine-2,4(1H,3H)-dione,
1-(3-nitrophenyl)-3-[5-(2-pyridonyl-1-methyl)methyl]-pyrido[2,3-d]pyrimidine-2,4(1H,3H)-dione,
1-(2-nitrophenyl)-3-[4-(2-pyranonyl)methyl]pyrido[2,3-d]pyrimidine-2,4(1H,3H)-dione,
1-(3-nitrophenyl)-3-[4-(2-pyranonyl)-2-ethyl]-pyrido[2,3-d]pyrimidine-2,4(1H,3H)-dione, and
1-(4-nitrophenyl)-3-[4-(2-pyranonyl)-2-ethyl]-pyrido[2,3-d]pyrimidine-2,4(1H,3H)-dione;

there are obtained the following compounds:
1-(2-aminophenyl)-3-(4-pyridyl-2-ethyl)pyrido[2,3-d]pyrimidine-2,4(1H,3H)-dione,
1-(3-aminophenyl)-3-(3-pyridylmethyl)pyrido[2,3-d]pyrimidine-2,4(1H,3H)-dione,
1-(4-aminophenyl)-3-(3-pyridyl-2-ethyl)pyrido[2,3-d]pyrimidine-2,4(1H,3H)-dione,
1-(3-aminophenyl)-3-(2-quinolinylmethyl)pyrido[2,3-d]pyrimidine-2,4(1H,3H)-dione,
1-(4-aminophenyl)-3-(2-quinolinyl-2-ethyl)pyrido[2,3-d]pyrimidine-2,4(1H,3H)-dione,
1-(2-aminophenyl)-3-[4-(2,6-dimethyl)pyridylmethyl]-pyrido[2,3-d]pyrimidine-2,4(1H,3H)-dione,
1-(4-aminophenyl)-3-[4-(2,6-dimethyl)pyridyl-2-ethyl]-pyrido[2,3-d]pyrimidine-2,4(1H,3H)-dione,
1-(2-aminophenyl)-3-(4-pyridonylmethyl)pyrido[2,3-d]pyrimidine-2,4(1H,3H)-dione,
1-(3-aminophenyl)-3-[4-(2-pyridonyl)-2-ethyl]-pyrido[2,3-d]pyrimidine-2,4(1H,3H)-dione,
1-(4-aminophenyl)-3-[4-(2-pyridonyl-1-methyl)methyl]-pyrido[2,3-d]pyrimidine-2,4(1H,3H)-dione,
1-(2-aminophenyl)-3-[5-(2-pyridonyl)methyl]-pyrido[2,3-d]pyrimidine-2,4(1H,3H)-dione,
1-(3-aminophenyl)-3-[5-(2-pyridonyl)-2-ethyl]-pyrido[2,3-d]pyrimidine-2,4(1H,3H)-dione,
1-(4-aminophenyl)-3-[5-(2-pyridonyl)-2-ethyl]-pyrido[2,3-d]pyrimidine-2,4(1H,3H)-dione,
1-(3-aminophenyl)-3-[5-(2-pyridonyl-1-methyl)-2-ethyl]pyrido[2,3-d]pyrimidine-2,4(1H,3H)-dione,
1-(3-aminophenyl)-3-[5-(2-pyridonyl-1-methyl)methyl]-pyrido[2,3-d]pyrimidine-2,4(1H,3H)-dione,
1-(2-aminophenyl)-3-[4-(2-pyranonyl)methyl]-pyrido[2,3-d]pyrimidine-2,4(1H,3H)-dione,
1-(3-aminophenyl)-3-[4-(2-pyranonyl)-2-ethyl]-pyrido[2,3-d]pyrimidine-2,4(1H,3H)-dione, and
1-(4-aminophenyl)-3-[4-(2-pyranonyl)-2-ethyl]-pyrido[2,3-d]pyrimidine-2,4(1H,3H)-dione.

20C. Formula I, Where Y is $-CH_2-$

By following the procedures of Example 20A and substituting 1-(3-nitrophenyl)-3-(4-pyridylmethyl)-pyrido[2,3-d]pyrimidine-2,4(1H,3H)-dione with the following:

1-(2-nitrophenyl)-3-(phenyl-2-ethyl)pyrido[2,3-d]pyrimidine-2(1H,3H)-one,
1-(2-nitrophenyl)-3-(benzyl)pyrido[2,3-d]pyrimidine-2(1H,3H)-one,
1-(2-nitrophenyl)-3-(4-pyridyl-2-ethyl)pyrido[2,3-d]pyrimidine-2(1H,3H)-one,
1-(3-nitrophenyl)-3-(3-pyridylmethyl)pyrido[2,3-d]pyrimidine-2(1H,3H)-one,
1-(4-nitrophenyl)-3-(3-pyridyl-2-ethyl)pyrido[2,3-d]pyrimidine-2(1H,3H)-one,
1-(3-nitrophenyl)-3-(2-quinolinylmethyl)pyrido[2,3-d]pyrimidine-2(1H,3H)-one,
1-(4-nitrophenyl)-3-(2-quinolinyl-2-ethyl)pyrido[2,3-d]pyrimidine-2(1H,3H)-one,
1-(2-nitrophenyl)-3-[4-(2,6-dimethyl)pyridylmethyl]-pyrido[2,3-d]pyrimidine-2(1H,3H)-one,
1-(4-nitrophenyl)-3-[4-(2,6-dimethyl)pyridyl-2-ethyl]-pyrido[2,3-d]pyrimidine-2(1H,3H)-one,
1-(2-nitrophenyl)-3-(4-pyridonylmethyl)pyrido[2,3-d]pyrimidine-2(1H,3H)-one,
1-(3-nitrophenyl)-3-[4-(2-pyridonyl)-2-ethyl]pyrido[2,3-d]pyrimidine-2(1H,3H)-one,
1-(4-nitrophenyl)-3-[4-(2-pyridonyl-1-methyl)methyl]-pyrido[2,3-d]pyrimidine-2(1H,3H)-one,
1-(2-nitrophenyl)-3-[5-(2-pyridonyl)methyl]pyrido[2,3-d]pyrimidine-2(1H,3H)-one, 1-(3-nitrophenyl)-3-[5-(2-pyridonyl)-2-ethyl]pyrido[2,3-d]pyrimidine-2(1H,3H)-one,
1-(4-nitrophenyl)-3-[5-(2-pyridonyl)-2-ethyl]pyrido[2,3-d]pyrimidine-2(1H,3H)-one,
1-(3-nitrophenyl)-3-[5-(2-pyridonyl-1-methyl)-2-ethyl]-pyrido[2,3-d]pyrimidine-2(1H,3H)-one,
1-(3-nitrophenyl)-3-[5-(2-pyridonyl-1-methyl)methyl]-pyrido[2,3-d]pyrimidine-2(1H,3H)-one,
1-(2-nitrophenyl)-3-[4-(2-pyranonyl)methyl]pyrido[2,3-d]pyrimidine-2(1H,3H)-one,
1-(3-nitrophenyl)-3-[4-(2-pyranonyl)-2-ethyl]-pyrido[2,3-d]pyrimidine-2(1H,3H)-one, and
1-(4-nitrophenyl)-3-[4-(2-pyranonyl)-2-ethyl]-pyrido[2,3-d]pyrimidine-2(1H,3H)-one;

there are obtained the following compounds:
1-(2-aminophenyl)-3-(phenyl-2-ethyl)pyrido[2,3-d]pyrimidine-2(1H,3H)-one,
1-(2-aminophenyl)-3-(benzyl)pyrido[2,3-d]pyrimidine-2(1H,3H)-one,
1-(2-aminophenyl)-3-(4-pyridyl-2-ethyl)pyrido[2,3-d]pyrimidine-2(1H,3H)-one,
1-(2-aminophenyl)-3-(3-pyridylmethyl)pyrido[2,3-d]pyrimidine-2(1H,3H)-one,
1-(4-aminophenyl)-3-(3-pyridyl-2-ethyl)pyrido[2,3-d]pyrimidine-2(1H,3H)-one,
1-(3-aminophenyl)-3-(2-quinolinylmethyl)pyrido[2,3-d]pyrimidine-2(1H,3H)-one,
1-(4-aminophenyl)-3-(2-quinolinyl-2-ethyl)pyrido[2,3-d]pyrimidine-2(1H,3H)-one,
1-(2-aminophenyl)-3-[4-(2,6-dimethyl)pyridylmethyl]-pyrido[2,3-d]pyrimidine-2(1H,3H)-one,
1-(4-aminophenyl)-3-[4-(2,6-dimethyl)pyridyl-2-ethyl]-pyrido[2,3-d]pyrimidine-2(1H,3H)-one,
1-(2-aminophenyl)-3-(4-pyridonylmethyl)pyrido[2,3-d]pyrimidine-2(1H,3H)-one,
1-(3-aminophenyl)-3-[4-(2-pyridonyl))-2-ethyl]-pyrido[2,3-d]pyrimidine-2(1H,3H)-one,
1-(4-aminophenyl)-3-[4-(2-pyridonyl-1-methyl)methyl]-pyrido[2,3-d]pyrimidine-2(1H,3H)-one,
1-(2-aminophenyl)-3-[5-(2-pyridonyl)methyl]-pyrido[2,3-d]pyrimidine-2(1H,3H)-one,
1-(3-aminophenyl)-3-[5-(2-pyridonyl)-2-ethyl]-pyrido[2,3-d]pyrimidine-2(1H,3H)-one,
1-(4-aminophenyl)-3-[5-(2-pyridonyl)-2-ethyl]-pyrido[2,3-d]pyrimidine-2(1H,3H)-one,
1-(3-aminophenyl)-3-[5-(2-pyridonyl-1-methyl)-2-ethyl]pyrido[2,3-d]pyrimidine-2(1H,3H)-one,
1-(3-aminophenyl)-3-[5-(2-pyridonyl-1-methyl)methyl]-pyrido[2,3-d]pyrimidine-2(1H,3H)-one,
1-(2-aminophenyl)-3-[4-(2-pyranonyl)methyl]-pyrido[2,3-d]pyrimidine-2(1H,3H)-one,
1-(3-aminophenyl)-3-[4-(2-pyranonyl)-2-ethyl]-pyrido[2,3-d]pyrimidine-2(1H,3H)-one, and
1-(4-aminophenyl)-3-[4-(2-pyranonyl)-2-ethyl]-pyrido[2,3-d]pyrimidine-2(1H,3H)-one.

EXAMPLE 21

Preparation of 1-(3-Nitrophenyl)-3-(4-pyridyl-N-oxide-methyl)pyrido[2,3-d]pyrimidine-2,4(1H,3H)-dione 1-(3-Nitrophenyl)-3-(4-pyridylmethyl)pyrido[2,3-d]pyrimidine-2,4(1H,3H)-dione (250 mg, 0.67 mmoles), prepared, e.g., in Example 5, was dissolved in methylene chloride (100 ml) and cooled to 0° C. To this solution, 231 mg (0.67 mmole) solid m-chloroperoxybenzoic acid (m-CPBA) was added. The reaction mixture was stirred for 1 hour at 0° C. The reaction mixture was allowed to warm to room temperature and stirred for an additional 18 hours. A 10% solution of $Na_2SO_3$ (20 ml) was added to the reaction mixture. The mixture was stirred at room temperature for 1.5 hours. A white solid emulsion was formed in the reaction mixture. The solid was isolated by filtration washed with saturated $NaHCO_3$ (2×10 ml) and $H_2O$ (2×10 ml), and air dried yielding 220 mg (0.56 mmole, 84% yield) of 1-(3-nitrophenyl)-3-(4-pyridyl-N-oxide-methyl)pyrido[2,3-d]pyrimidine-2,4(1H,3H)-dione. Characteristic analytical data are: mp>270° C.; $H^1$ NMR (Me$_2$SO-d$_6$) δ 5.12 (s, 2H), 7.39 (q, 1H), 7.45 (d, J=7.0, 2H), 7.85 (t, 1H), 7.91 (dd, 1H), 8.16 (d, J=7.0, 2H), 8.36 (dd, 1H), 8.43 (t, 1H), 8.50 (dd, 1H) and 8.55 (dd, 1H).

EXAMPLE 22

Preparation of 1-(3-nitrophenyl)-3-(4-pyridylmethyl)pyrido[2,3-d]pyrimidine-2,4(1H,3H)-dione hydrochloride 1-(3-Nitrophenyl)-3-(4-pyridylmethyl)pyrido[2,3-d]pyrimidine-2,4(1H,3H)-dione (450 mg, 1.20 mmoles), prepared, e.g., in Example 5, was suspended in methanol (5 ml) and to this suspension, 5 ml of a 5% HCl/methanol solution was added. The suspension was stirred for 45 minutes during which a clear solution was formed. The solvent was removed and the residue was triturated with ethyl ether. A white precipitate was formed and isolated by filtration yielding 439 mg (1.06 mmole, 89% yield) of 1-(3-nitrophenyl)-3-(4-pyridylmethyl)pyrido[2,3-d]pyrimidine-2,4(1H,3H)-dione hydrochloride (mp 265°–270° C).

EXAMPLE 23

Determination of Potency and Selectivity of Inhibitors for PDE IV

Preparation of Human Platelet Phosphodiesterase (PDE III)

Platelet high-affinity cAMP PDE (PDE III) was obtained from human blood in accordance with previously described procedures described in Mol. Pharmacol., 20:302–309, Alvarez, R., Taylor, A., Fazarri, J. J., and Jacobs, J. R. (1981).

Blood was collected into evacuated tubes containing EDTA (7.7 mM, final concentration). PRP was obtained by centrifuging the blood in polycarbonate tubes at 200×g for 15 min at 4° C. A platelet pellet was resuspended in a volume of buffer A (0.137M NaCl, 12.3 mM Tris-HCl buffer, pH 7.7, containing 1 mM $MgCl_2$. The hypotonically-lysed platelet suspension was centrifuged at 48,000×g for 15 min and the supernatant was saved. The pellets were frozen on dry ice and briefly thawed at 22° C. The supernatant was combined with the pellet fraction and the resulting suspension was fraction was stored in 0.5 ml aliquots at −20° C. and used as the soluble PDE. Enzyme activity was adjusted to 10–20% hydrolysis after 10 minutes of incubation by dilution with 10mM cold Tris-HCl buffer, pH7.7.

Preparation of Human Lymphocyte Phosphodiesterase (PDE IV)

Human B cell line (43D) were cultured at 37° C. in 7% $CO_2$ in RPMI 1640 with L-glutamine and 10% Nu-Serum. Prior to the assay ~1.5×10⁸ cells were centrifuged at 1000 rpm for 10 minutes in a table top clinical centrifuge. The pellet was resuspended in 2–3 ml of 45 mM Tris-HCl buffer, pH 7.4. The suspension was homogenized and centrifuged at 12,000×g 4° C.

for 10 minutes. The supernatant was diluted to 28 ml with Tris-HCl buffer and used directly in the assay or stored at −20° C. The final concentration of DMSO in the PDE incubation medium was 1%. Nitraquazone was included in each assay (10 and 100 μM) as a reference standard.

Human Platelet cAMP Phosphodiesterase Assay

The phosphodiesterase incubation medium contained 10 mM Tris-HCl buffer, pH 7.7, 10 mM MgSO$_4$, 0.1–1 μM [$^3$H]-AMP (0.2 μCi) in a total volume of 1.0 ml. Following addition of the enzyme, the contents were mixed and incubated for 10 min at 30° C. The reaction was terminated by immersing the tubes in a boiling-water bath for 90 sec. After the tubes were cooled in an ice-water bath, 0.1 ml (100μg) of 5'-nucleotidase from snake venom (*Crotalus atrox*, Sigma V-7000) was added to each tube. The contents were mixed and incubated for 30 min at 30° C. The nucleotidase reaction was terminated by immersing the tubes in a boiling water bath for 60 sec. Labeled adenosine was isolated from alumina columns according to the method described in *Anal. Biochem.*, 52:505–516 (1973), Filburn, C. R., and Karn, J. Assays were performed in triplicate. Hydrolysis of cAMP ranged from 10–20%. Test compounds were dissolved in DMSO. The final concentration of DMSO in the phosphodiesterase assay was 1% when tested with compounds up to 0.1 mM. When tested at 1 mM the DMSO concentration was 10% and this activity was compared to control PDE activity in the presence of 10% DMSO.

Human Lymphocyte cAMP Phosphodiesterase Assay

The phosphodiesterase incubation medium contained 40 mM Tris-HCl buffer, pH 7.7, 0.1 mM MgSO$_4$, 3.75 mM mercaptoethanol, and 0.1–1 μM [$^3$H] cAMP (0.2 μCi) in a total volume of 1.0 ml. The reaction was performed and processed according to the procedure used (above) for human platelet PDE. The final concentration of DMSO was 1%.

Representative compounds of the present invention exhibit potency and selectivity as inhibitors of PDE IV when tested by the human platelet cAMP phosphodiesterase assay and the human lymphocyte cAMP phosphodiesterase assay.

EXAMPLE 24

Determination of Immunosuppressive Activity Utilizing Responses of Human Peripheral Blood Lymphocytes to Mitogen This procedure is a modification of a procedure initially described by Greaves, et al. ["Activation of human T and B lymphocytes by polyclonal mitogens," *Nature*, 248, 698–701 (1974)].

Human mononuclear cells (PBL) were separated from heparinized whole blood by density gradient centrifugation in Ficoll-Paque (Pharmacia). After washing, 5×10$^4$ cells/well are cultured in microtiter plates with minimal essential media supplemented with 1% human serum, gentamicin, sodium bicarbonate, 2-mercaptoethanol, glutamine, non-essential amino acids, and sodium pyruvate. The mitogen concanavalin A (Sigma) is used at a concentration of 2 μg/ml. Test materials are tested at concentrations between 10$^{-4}$ and 10$^{-10}$M, by addition to the culture at time 0. Cultures are set up in quadruplicate and incubated at 37° C. in a humidified atmosphere with 5% CO$_2$ for 48 hours. A pulse of 1.0 μCi/well of $^3$H-thymidine is added for the last 4 hours. Cells are collected on glass fiber filters with an automatic harvester and radioactivity is measured by standard scintillation procedures. The 50% inhibitory concentration ("IC$_{50}$") for mitogenic stimulation is determined graphically.

Representative compounds of the present invention showed immunosuppressive activity when tested by this method.

EXAMPLE 25

Determination of Immunosuppressive Activity Utilizing The Hemolytic Plaque Forming Cell Assay This procedure is a modification of "The agar plaque technique for recognizing antibody producing cells," a procedure initially described by Jerne, et al. [*Cell-bound Antibodies*, Amos and Kaprowski editors (Wistar Institute Press, Philadelphia, 1963) p. 109].

Groups of 5–6 adult C3H female mice were sensitized with 1.25×10$^8$ sheep red blood cells (SRBC) and simultaneously treated with an oral dosage form of the test material in an aqueous vehicle. Animals in a control group receive the same volume of vehicle. Four days after SRBC inoculation, spleens are dispersed in glass homogenizers. The number of nucleated cells (WBC) is determined and the spleen cell suspension is mixed with SRBC, guinea pig complement and agar solution at 0.5% concentration. Aliquots of the above mixture (0.1 ml) are dropped on four separate quadrants of a Petri dish and are covered with cover slips. After two hours incubation at 7° C., areas of hemolysis around plaque-forming cells (PFC) are counted with a dissecting microscope. Total WBC/spleen, PFC/spleen and PFC/10$^6$ WBC (PPM) are calculated for each mouse spleen. Geometric means of each treatment group are then compared with the vehicle-treated control group.

Representative compounds of the present invention showed immunosuppressive activity when tested by this method.

EXAMPLE 26

Determination of Anti-Inflammatory Activity Utilizing Arachidonic Acid-Induced Ear Edema in the Mouse This procedure is a modification of a procedure described by Young et al., *J. Invest. Derm.* 82:367–371 (1984).

Female Charles River ICR mice 23–27 grams are administered 0.2 ml of test material. The mice are later challenged with 20 μl of arachidonic acid applied topically to the ear. One hour after challenge, the weight of an 8 mm disc is determined. The mean increase in ear plug weight is calculated. Materials with anti-inflammatory activity inhibit the increase in ear plug weight.

Representative compounds of the present invention exhibited anti-inflammatory activity when tested by this method.

EXAMPLE 27

Determination of Anti-inflammatory Activity Utilizing Adjuvant-Induced Arthritis in the Rat This procedure is a modification of a procedure initially described by Pearson, C. M., *Proc. Soc. Exp. Biol. Med.*, 91:95–101 (1956).

Female Charles River albino rats weighing 160–180 g receive 0.1 ml of a suspension in paraffin oil of heat-killed *Mycobacterium butyricum* (10 mg/ml) by means of an intradermal injection into the proximal ¼ of the tail on day 0. Beginning on day 1, the test material is administered orally in an aqueous vehicle (0.5 ml/dose) once each day for 17 days. On day 18 the intensity of the swelling of the four foot pads and tail is determined utilizing a scoring system in which the swelling in the four paws was scored 0-4 for each paw and the tail swelling is scored 0-3, such that the total maximum score is 19.

Representative compounds of the present invention exhibited anti-inflammatory activity when tested by this method.

EXAMPLE 28

Determination of Activity Towards Autoimmune Disease Utilizing Survival of MRL/lpr Mice MRL/lpr mice develop a multisystemic disease characterized by glomerulonephritis, arthritis, arteritis, lymphoid hyperplasia. The length of survival of mice with this disease is approximately one-third that of non-disease developing MRL/n mice. These mice have a high incidence of autoantibodies and the disease process is considered autoimmune in nature as described by Theofilopoulos, et al., *Advances in Immunology*, 37:269–390 (1985).

Representative compounds of the present invention significantly extended the lifespan of the MRL/lpr mice.

EXAMPLE 29

Determination of Analgetic Activity Utilizing Phenylquinone-Induced Stretching in the Mouse This procedure is a modification of a procedure described by Hendershoot, et al. *J. Pharmacol. Exp. Ther.*, 12:237–240 (1959).

Groups of 8 Female CD-1 mice are administered test materials orally in an aqueous vehicle. At various times following administration of test materials, 0.25 ml of a 0.02% solution of phenylquinone is administered intraperitoneally. The number of stretches for each animal is enumerated over a ten minute period following the phenylquinone administration. Analgetic activity is determined by inhibition of the mean number of stretches.

Representative compounds of the present invention showed analgetic activity when tested by this method.

EXAMPLE 30

Capsule Formulation

This example illustrates the preparation of a representative pharmaceutical formulation for oral administration containing an active compound of Formula I, e.g., 1-(3-nitrophenyl)-3-(4-pyridylmethyl)pyrido[2,3-d]pyrimidine-2,4(1H,3H)-dione.

| Ingredients | Quantity (mg/capsule) |
| --- | --- |
| Active compound | 200 |
| lactose, spray-dried | 148 |
| magnesium stearate | 2 |

The above ingredients are mixed and introduced into a hard-shell gelatin capsule.

Other compounds of Formula I, such as those prepared in accordance with Examples 1–22 can be used as the active compound in the preparation of the orally administrable formulations of this example.

EXAMPLE 31

Oral Formulation

This example illustrates the preparation of a representative pharmaceutical formulation containing an active compound of Formula I, e.g., 1-(3-chlorophenyl)-3-(4-pyridylmethyl)pyrido[2,3-d]pyrimidine-2,4(1H,3H)-dione.

An suspension for oral administration is prepared having the following composition:

| Ingredients | Quantity |
| --- | --- |
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Other compounds of Formula I, such as those prepared in accordance with Examples 1–22 can be used as the active compound in the preparation of the orally administrable formulations of this example.

EXAMPLE 32

Tablet Formulation

This example illustrates the preparation of a representative pharmaceutical formulation containing an active compound of Formula I, e.g., 1-(3-nitrophenyl)-3-(4-pyridylmethyl)pyrido[2,3-d]pyrimidine-2,4(1H,3H)-dione.

A tablet for oral administration is prepared having the following composition:

| Ingredients | Quantity (mg/tablet) |
| --- | --- |
| Active compound | 400 |
| corn starch | 50 |
| lactose | 145 |
| magnesium stearate | 5 |

The above ingredients are mixed intimately and pressed into single scored tablets.

Other compounds of Formula I, such as those prepared in accordance with Examples 1–22 can be used as the active compound in the preparation of the tablet formulations of this example.

EXAMPLE 33

Injectable Formulation

This example illustrates the preparation of a representative pharmaceutical formulation containing an active compound of Formula I, e.g., 1-(3-chlorophenyl)-3-(4-pyridylmethyl)pyrido[2,3-d]pyrimidine-2,4(1H,3H)-dione.

An injectable preparation is prepared having the following composition:

| Ingredients | Quantity |
| --- | --- |
| Active compound | 0.2 g |
| water (distilled, sterile) | q.s. to 20.0 mL |

Other compounds of Formula I, such as those prepared in accordance with Examples 1-22 can be used as the active compound in the preparation of the injection administrable formulations of this example.

EXAMPLE 34

Suppository Formulation

This example illustrates the preparation of a representative pharmaceutical formulation containing an active compound of Formula I, e.g., 1-(3-nitrophenyl)-3-(4-pyridylmethyl)pyrido[2,3-d]pyrimidine-2,4(1H,3H)-dione.

A suppository totalling 2.5 grams is prepared having the following composition:

| Ingredients | Quantity |
|---|---|
| Active compound | 500 mg |
| witepsol H-15* | q.s. to 2.5 g |

(*triglycerides of saturated vegetable fatty acid; a product of Riches-Nelson, Inc., New York, N.Y.).

Other compounds of Formula I, such as those prepared in accordance with Examples 1-22 can be used as the active compound in the preparation of the suppository formulations of this example.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula:

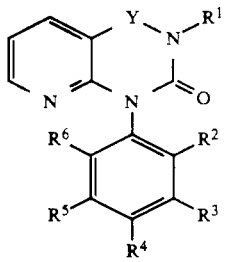

wherein:
Y is —CH$_2$— or —C(O)—;
R$^1$ is —(CH$_2$)$_n$—R$^7$, wherein:
R$^7$ is heteroaryl selected from the group consisting of pyridyl, quinolinyl, furanyl, and pyridonyl, and
n is 1 or 2,
R$^2$, R$^3$, R$^4$, R$^5$ and R$^6$ are hydrogen, or one is selected from the group consisting of lower alkyl, halo, carboxy, methoxycarbonyl, carbamoyl, methylcarbamoyl, di-methylcarbamoyl, methylcarbonyl, methylthio, methylsulfinyl, methylsulfonyl, hydroxymethyl, amino, trifluoromethyl, cyano or nitro;
or a pharmaceutically acceptable ester, ether, N-oxide or salt thereof.

2. The compound of claim 1 wherein R$^1$ is —(CH$_2$)—R$^7$.
3. The compound of claim 2 wherein n is one or two.
4. The compound of claim 3 wherein Y is —C(O)—.
5. The compound of claim 4 wherein R$^3$ is nitro.
6. The compound of claim 4 wherein R$^3$ is chloro.
7. The compound of claim 4 wherein R$^3$ is methoxycarbonyl.
8. The compound of claim 5 wherein n is one.
9. The compound of claim 8 wherein R$^7$ is pyridyl.
10. The compound of claim 9 wherein R$^7$ is 4-pyridyl.
11. The compound of claim 1, which is 1-(3-nitrophenyl)-3-(4-pyridylmethyl)pyrido[2,3-d]pyrimidine-2,4(1H,3H)-dione.
12. The compound of claim 1, which is 1-(3-nitrophenyl)-3-(4-pyridylmethyl)pyrido[2,3-d]pyrimidine-2,4(1H,3H)-dione hydrochloride.
13. The compound of claim 9 wherein R$^7$ is 3-pyridyl.
14. The compound of claim 1, which is 1-(3-nitrophenyl)-3-(3-pyridylmethyl)pyrido[2,3-d]pyrimidine-2,4(1H,3H)-dione.
15. The compound of claim 9 wherein R$^7$ is 2-pyridyl.
16. The compound of claim 1, which is 1-(3-nitrophenyl)-3-(2-pyridylmethyl)pyrido[2,3-d]pyrimidine-2,4(1H,3H)-dione
17. The compound of claim 8 wherein R$^7$ is quinolinyl.
18. The compound of claim 17 wherein R$^7$ is 2-quinolinyl.
19. The compound of claim 6 wherein n is one.
20. The compound of claim 19 wherein R$^7$ is pyridyl.
21. The compound of claim 20 wherein R. is 4-pyridyl.
22. The compound of claim 1, which is 1-(3-chlorophenyl)-3-(4-pyridylmethyl)pyrido[2,3-d]pyrimidine-2,4(1H,3H)-dione.
23. The compound of claim 20 wherein R$^7$ is 3-pyridyl.
24. The compound of claim 1, which is 1-(3-chlorophenyl)-3-(3-pyridylmethyl)pyrido[2,3-d]pyrimidine-3H)-dione.
25. The compound of claim 20 wherein R$^7$ is 2-pyridyl.
26. The compound of claim 19 wherein R$^7$ is quinolinyl.
27. The compound of claim 26 wherein R$^7$ is 2-quinolinyl.
28. The compound of claim 7 wherein n is one.
29. The compound of claim 28 wherein R$^7$ is pyridyl.
30. The compound of claim 29 wherein R$^7$ is 4-pyridyl
31. The compound of claim 1, which is 1-(3-methoxycarbonylphenyl)-3-(4-pyridylmethyl)pyrido[2,3-d]pyrimidine-2,4(1H,3H)-dione.
32. The compound of claim 29 wherein R$^7$ is 3-pyridyl.
33. The compound of claim 1, which is 1-(3-methoxycarbonylphenyl)-3-(3-pyridylmethyl)pyrido[2,3-d]pyrimidine-2,4(1H,3H)-dione.
34. The compound of claim 29 wherein R$^7$ is 2-pyridyl.
35. The compound of claim 28 wherein R$^7$ is quinolinyl.
36. The compound of claim 35 wherein R$^7$ is 2-quinolinyl.
37. The compound of claim 1, which is 1-(3-fluorophenyl)-3-(4-pyridylmethyl)pyrido[2,3-d]pyrimidine-3H)-dione.

38. The compound of claim 1, which is 1-(3-cyanophenyl)-3-(4-pyridylmethyl)pyrido[2,3-d]pyrimidine-2,4(1H,3H)-dione.

39. The compound of claim 1, which is 1-(3-methylthiophenyl)-3-(4-pyridylmethyl)pyrido[2,3-d]pyrimidine-3H)-dione.

40. The compound of claim 1, which is 1-phenyl-3-(4-pyridylmethyl)pyrido[2,3-d]pyrimidine-2,4(1H,3H)-dione.

41. The compound of claim 3 wherein Y is —CH$_2$—.

42. The compound of claim 41 wherein n is one.

43. The compound of claim 42 wherein R$^3$ is chloro.

44. The compound of claim 42 wherein R$^3$ is nitro.

45. The compound of claim 42 wherein R$^3$ is methoxycarbonyl.

46. The compound of claim 42 wherein R$^7$ is pyridyl.

47. The compound of claim 42 wherein R$^7$ is 4-pyridyl.

48. The compound of claim 1, which is 1-(3-chlorophenyl)-3-(4-pyridylmethyl)pyrido[2,3-d]pyrimidine-2(1H,3H)-one.

49. The compound of claim 42 wherein R$^7$ is 3-pyridyl.

50. The compound of claim 1, which is 1-(3-chlorophenyl)-3-(3-pyridylmethyl)pyrido[2,3-d]pyrimidine-2(1H,3H)-one.

51. A compound of the formula:

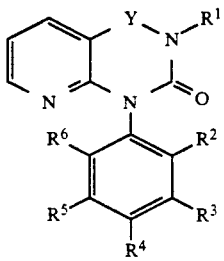

wherein:
Y is —CH$_2$— or —C(O)—;
R$^1$ is —(CH$_2$)$_n$—R$^7$, wherein:
R$^7$ is heteroaryl selected from the group consisting of pyridyl, quinolinyl, furanyl, and pyridonyl, and
n is 1 or 2,
R$^3$ is an electron withdrawing group selected from the group consisting of nitro, chloro, fluoro, trimethylfluoro, cyano, carboxy, methoxycarbonyl and methylcarbonyl; and
R$^2$, R$^4$, R$^5$ and R$^6$ are hydrogen;
or a pharmaceutically acceptable ester, ether, N-oxide or salt thereof.

52. A compound of the formula:

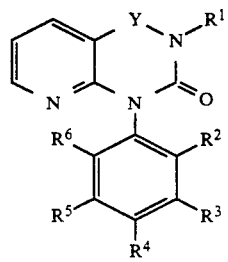

wherein:
Y is —CH$_2$— or —C(O)—;
R$^1$ is —(CH$_2$)$_n$—R$^7$, wherein:
R$^7$ is heteroaryl selected from the group consisting of pyridyl, quinolinyl, furanyl, and pyridonyl, and
n is 1 or 2,
R$^2$, R$^3$, R$^4$, and R$^5$ are independently selected from the group consisting of hydrogen, lower alkyl, nitro, chloro, fluoro, methoxycarbonyl or methylcarbonyl, provided at least one is hydrogen; and
R$^6$ is hydrogen;
or a pharmaceutically acceptable ester, ether or salt thereof.

53. A pharmaceutical composition comprising a pharmaceutically acceptable excipient and therapeutically effective amount of a compound according to claim 1.

* * * * *

UNITED STATES PATENT AND TRADEMARK OFFICE
CERTIFICATE OF CORRECTION

PATENT NO. : 5,264,437
DATED : 11/23/93
INVENTOR(S) : Wilhelm, et al.

It is certified that error appears in the above-identified patent and that said Letters Patent is hereby corrected as shown below:

Claim 24 at column 68, line 41 "3H)-dione." should read --2,4(1H,3H)-dione.--

Claim 37 at column 68, line 68 "3H)-dione." should read --2,4(1H,3H)-dione.--

Claim 39 at column 69, line 6 "dine-3H)-dione." should read --dine-2,4(1H,3H)-dione.--

Claim 51 at column 70, line 10 after "ether," delete --N-oxide--

Signed and Sealed this

Seventeenth Day of May, 1994

*Attest:*

BRUCE LEHMAN

*Attesting Officer*     *Commissioner of Patents and Trademarks*